US011918357B2

(12) United States Patent
Devgon et al.

(10) Patent No.: US 11,918,357 B2
(45) Date of Patent: Mar. 5, 2024

(54) DEVICES AND METHODS FOR PHLEBOTOMY THROUGH A CLOSED SYSTEM INTRAVENOUS CATHETER

(71) Applicant: Velano Vascular, Inc., San Francisco, CA (US)

(72) Inventors: Pitamber Devgon, Philadelphia, PA (US); Brian J. Funk, San Francisco, CA (US); Evan Vandenbrink, Burlingame, CA (US)

(73) Assignee: Velano Vascular, Inc., San Francisco, CA (US)

( * ) Notice: Subject to any disclaimer, the term of this patent is extended or adjusted under 35 U.S.C. 154(b) by 808 days.

(21) Appl. No.: 16/586,326

(22) Filed: Sep. 27, 2019

(65) Prior Publication Data
US 2020/0100716 A1 Apr. 2, 2020

Related U.S. Application Data

(60) Provisional application No. 62/842,918, filed on May 3, 2019, provisional application No. 62/738,200, filed on Sep. 28, 2018.

(51) Int. Cl.
*A61B 5/15* (2006.01)
(52) U.S. Cl.
CPC .... *A61B 5/15003* (2013.01); *A61B 5/150267* (2013.01); *A61B 5/150389* (2013.01); *A61B 5/150732* (2013.01)
(58) Field of Classification Search
CPC .......... A61B 5/15003; A61B 5/150267; A61B 5/150389; A61B 5/150732;
(Continued)

(56) References Cited

U.S. PATENT DOCUMENTS

| 4,245,635 A | * | 1/1981 | Kontos | A61M 39/06 604/167.03 |
| 4,468,224 A | | 8/1984 | Enzmann et al. | |

(Continued)

FOREIGN PATENT DOCUMENTS

| CN | 104902856 | * | 9/2015 | |
| EP | 2319575 A1 | * | 5/2011 | A61B 17/22 |

(Continued)

OTHER PUBLICATIONS

English-language machine translation of KR 20120003185, pp. 1-26, 2012 (Year: 2012).*

(Continued)

*Primary Examiner* — Yi-Shan Yang
(74) *Attorney, Agent, or Firm* — The Webb Law Firm

(57) ABSTRACT

An apparatus includes a catheter, an introducer, and an actuator. A distal end portion of the introducer has a lock configured to couple the introducer to a closed system intravenous line at least partially disposed in a body. The lock is configured to transition a seal of the closed system intravenous line from a closed state to an open state when coupled thereto. The actuator is at least partially disposed in the introducer and coupled to a proximal end portion of the catheter. The actuator is configured to move the catheter between a first position, in which the catheter is disposed within the introducer, and a second position, in which the catheter extends through the seal of the closed system intravenous line such that a distal end surface of the catheter is positioned distal to the closed system intravenous line.

16 Claims, 17 Drawing Sheets

(58) Field of Classification Search
CPC ........ A61B 5/150633; A61B 5/150641; A61B 5/150648; A61B 5/150656; A61B 5/150664; A61B 5/15074; A61B 5/153; A61B 5/15; A61B 5/150015; A61B 5/150022; A61B 5/15019; A61B 5/150206; A61B 5/150251; A61B 5/150274–297; A61B 5/150351; A61B 5/150354; A61B 5/150007; A61B 5/0538; A61B 5/1459; A61B 5/1473; A61B 5/14865; A61M 25/0097; A61M 25/06–0637; A61M 25/060637; A61M 39/00–06; A61M 2039/062; A61M 25/00–0693; A61M 2025/0004

See application file for complete search history.

(56) References Cited

U.S. PATENT DOCUMENTS

| | | |
|---|---|---|
| 4,578,063 A | 3/1986 | Inman et al. |
| 5,336,195 A | 8/1994 | Daneshvar |
| 5,465,938 A | 11/1995 | Werge et al. |
| 5,535,785 A | 7/1996 | Werge et al. |
| 5,556,381 A | 9/1996 | Ensminger et al. |
| 5,681,290 A | 10/1997 | Alexander |
| 5,693,032 A | 12/1997 | Bierman |
| 5,755,225 A | 5/1998 | Hutson |
| 5,775,671 A | 7/1998 | Cote, Sr. |
| 5,807,342 A | 9/1998 | Musgrave et al. |
| 5,810,781 A | 9/1998 | Bierman |
| 5,833,666 A | 11/1998 | Davis et al. |
| 6,086,564 A | 7/2000 | McLaughlin |
| 6,213,979 B1 | 4/2001 | Bierman |
| 6,283,945 B1 | 9/2001 | Bierman |
| 6,332,874 B1 | 12/2001 | Eliasen et al. |
| 6,361,523 B1 | 3/2002 | Bierman |
| 6,413,240 B1 | 7/2002 | Bierman et al. |
| 6,418,966 B2 | 7/2002 | Loo |
| 6,428,513 B1 | 8/2002 | Abrahamson |
| 6,537,254 B1 | 3/2003 | Schock et al. |
| 6,551,284 B1 | 4/2003 | Greenberg et al. |
| 6,585,229 B2 | 7/2003 | Cote, Sr. et al. |
| 6,663,600 B2 | 12/2003 | Bierman et al. |
| 6,892,998 B2 | 5/2005 | Newton |
| 6,929,625 B2 | 8/2005 | Bierman |
| 6,951,550 B2 | 10/2005 | Bierman |
| 7,014,169 B2 | 3/2006 | Newton et al. |
| 7,014,627 B2 | 3/2006 | Bierman |
| 7,018,362 B2 | 3/2006 | Bierman et al. |
| 7,198,616 B2 | 4/2007 | Mossanen-Shams et al. |
| 7,223,256 B2 | 5/2007 | Bierman |
| 7,247,150 B2 | 7/2007 | Bierman |
| 7,357,792 B2 | 4/2008 | Newton et al. |
| 7,396,348 B2 | 7/2008 | Newton et al. |
| 7,563,251 B2 | 7/2009 | Bierman et al. |
| 7,591,803 B2 | 9/2009 | Bierman |
| 7,594,910 B2 | 9/2009 | Butts et al. |
| 7,635,355 B2 | 12/2009 | Bierman |
| 7,722,571 B2 | 5/2010 | Bierman et al. |
| 7,785,295 B2 | 8/2010 | Bierman |
| 7,789,864 B2 | 9/2010 | Cote, Sr. et al. |
| 7,879,013 B2 | 2/2011 | Smith et al. |
| 7,887,519 B2 | 2/2011 | Cote, Sr. et al. |
| 7,981,087 B2 | 7/2011 | Gesler, III |
| 8,016,793 B2 | 9/2011 | Wright et al. |
| 8,025,643 B2 | 9/2011 | Bierman |
| 8,029,476 B2 | 10/2011 | Rosenberg et al. |
| 8,052,648 B2 | 11/2011 | Dikeman et al. |
| 8,052,649 B2 | 11/2011 | Wright |
| 8,083,723 B2 | 12/2011 | Glenn |
| 8,095,223 B2 | 1/2012 | Cleary et al. |
| 8,100,869 B2 | 1/2012 | Vangsness et al. |
| 8,105,289 B2 | 1/2012 | Bierman et al. |
| 8,105,290 B2 | 1/2012 | Wright et al. |
| 8,114,054 B2 | 2/2012 | Bierman et al. |
| 8,137,323 B2 | 3/2012 | Rosenberg et al. |
| 8,177,756 B2 | 5/2012 | Wright |
| 8,241,253 B2 | 8/2012 | Bracken |
| 8,246,583 B2 | 8/2012 | Bierman |
| 8,337,461 B2 | 12/2012 | Burkholz |
| 8,394,066 B2 | 3/2013 | Rosenberg et al. |
| 8,398,599 B2 | 3/2013 | Bierman |
| 8,425,476 B2 | 4/2013 | Glenn |
| 8,506,533 B2 | 8/2013 | Carlyon et al. |
| 8,585,655 B2 | 11/2013 | Bierman |
| 8,622,972 B2 | 1/2014 | Nystrom et al. |
| 8,636,698 B2 | 1/2014 | Bierman et al. |
| 8,657,791 B2 | 2/2014 | Bierman et al. |
| 8,795,237 B2 | 8/2014 | Vitaris et al. |
| 8,876,784 B2 | 11/2014 | Cote, Sr. et al. |
| 8,915,885 B2 | 12/2014 | Smith et al. |
| 8,915,891 B2 | 12/2014 | Bornhoft |
| 8,932,263 B2 | 1/2015 | Rosenberg et al. |
| 8,968,261 B2 | 3/2015 | Kimball et al. |
| 8,979,805 B1 | 3/2015 | Khalaj |
| 9,056,186 B2 | 6/2015 | Wright et al. |
| 9,061,122 B2 | 6/2015 | Bierman et al. |
| 9,138,572 B2 | 9/2015 | Zeytoonian et al. |
| 9,314,596 B2 | 4/2016 | Rosenberg et al. |
| 9,333,323 B2 | 5/2016 | Racz et al. |
| 9,408,569 B2 | 8/2016 | Andreae et al. |
| 9,433,754 B2 | 9/2016 | Mogg |
| 9,452,278 B2 | 9/2016 | Davis et al. |
| 9,480,821 B2 | 11/2016 | Ciccone et al. |
| 9,486,613 B2 | 11/2016 | Dickert et al. |
| 9,526,869 B2 | 12/2016 | Beran |
| 9,545,502 B2 | 1/2017 | Maseda et al. |
| 9,550,043 B2 | 1/2017 | Rosenberg et al. |
| 9,550,044 B2 | 1/2017 | Maseda et al. |
| 9,604,047 B2 | 3/2017 | Newton et al. |
| 9,743,877 B2 | 8/2017 | Pazart et al. |
| 9,744,344 B1 | 8/2017 | Devgon et al. |
| 9,782,567 B2 | 10/2017 | Rosenberg et al. |
| 9,855,386 B2 | 1/2018 | Close et al. |
| 9,872,644 B2 | 1/2018 | Chelak et al. |
| 10,076,272 B2 | 9/2018 | Devgon et al. |
| 10,105,085 B2 | 10/2018 | Andreae et al. |
| 10,300,247 B2 | 5/2019 | Devgon et al. |
| 10,357,636 B2 | 7/2019 | Sonderegger et al. |
| 10,376,684 B2 | 8/2019 | Chelak et al. |
| 10,426,929 B2 | 10/2019 | Burkholz et al. |
| 10,744,314 B2 | 8/2020 | Siopes et al. |
| D889,589 S | 10/2020 | Illsley |
| 10,835,730 B2 | 11/2020 | Chelak et al. |
| 10,953,219 B2 | 3/2021 | Chelak et al. |
| 10,987,041 B2 | 4/2021 | Maseda et al. |
| 11,013,902 B2 | 5/2021 | Chelak et al. |
| 11,090,461 B2 | 8/2021 | Ehrenreich et al. |
| 11,224,720 B2 | 1/2022 | Brunetti et al. |
| 2005/0131351 A1 | 6/2005 | Bierman |
| 2006/0084922 A1 | 4/2006 | Botha |
| 2006/0217669 A1 | 9/2006 | Botha |
| 2006/0270994 A1 | 11/2006 | Bierman |
| 2007/0066958 A1 | 3/2007 | Wright |
| 2007/0142782 A2 | 6/2007 | Bierman |
| 2007/0149930 A1 | 6/2007 | Bierman |
| 2008/0125718 A1 | 5/2008 | Tsuchiya et al. |
| 2008/0200880 A1 | 8/2008 | Kyvik et al. |
| 2008/0221550 A1* | 9/2008 | Lee ............... A61M 25/10 604/93.01 |
| 2008/0319387 A1 | 12/2008 | Amisar et al. |
| 2009/0149814 A1 | 6/2009 | Bailey et al. |
| 2009/0209922 A1 | 8/2009 | Boisjoly |
| 2010/0030164 A1 | 2/2010 | Kimball et al. |
| 2010/0100049 A1 | 4/2010 | Godfrey |
| 2010/0179481 A1 | 7/2010 | Bierman et al. |
| 2010/0179563 A1 | 7/2010 | Skakoon et al. |
| 2010/0249725 A1 | 9/2010 | Cote, Sr. et al. |
| 2010/0298777 A1 | 11/2010 | Nishtala |
| 2011/0106057 A1 | 5/2011 | Hamboly |
| 2011/0213310 A1 | 9/2011 | Bierman |
| 2011/0282291 A1 | 11/2011 | Ciccone |
| 2012/0016312 A1 | 1/2012 | Brown et al. |
| 2012/0041377 A1 | 2/2012 | Haak |

(56) References Cited

U.S. PATENT DOCUMENTS

| | | |
|---|---|---|
| 2012/0059328 A1 | 3/2012 | Dikeman et al. |
| 2012/0136314 A1 | 5/2012 | Ciccone et al. |
| 2012/0197205 A1 | 8/2012 | Peters |
| 2012/0220955 A1 | 8/2012 | Maseda et al. |
| 2012/0232490 A1 | 9/2012 | Andino |
| 2012/0271240 A1 | 10/2012 | Andino et al. |
| 2012/0277627 A1 | 11/2012 | Devgon |
| 2013/0053785 A1 | 2/2013 | Parvatiyar et al. |
| 2013/0138045 A1 | 5/2013 | Bierman |
| 2014/0061408 A1 | 3/2014 | Heinecke et al. |
| 2014/0114211 A1 | 4/2014 | Hadvary et al. |
| 2014/0200517 A1 | 7/2014 | Humphries et al. |
| 2014/0343531 A1 | 11/2014 | Larkin |
| 2014/0364766 A1 | 12/2014 | Devgon et al. |
| 2015/0112270 A1 | 4/2015 | Smith et al. |
| 2015/0119845 A1 | 4/2015 | Collins et al. |
| 2015/0141962 A1 | 5/2015 | Collins et al. |
| 2015/0217088 A1 | 8/2015 | Zyzelewski et al. |
| 2015/0224286 A1 | 8/2015 | Teh et al. |
| 2015/0367102 A1 | 12/2015 | Andino et al. |
| 2016/0015932 A1 | 1/2016 | Catudal |
| 2016/0073937 A1 | 3/2016 | Burkholz et al. |
| 2016/0184554 A1 | 6/2016 | Rosenberg et al. |
| 2016/0354580 A1 | 12/2016 | Teoh et al. |
| 2016/0367789 A1 | 12/2016 | Beran |
| 2017/0043130 A1 | 2/2017 | Jones et al. |
| 2017/0151417 A1 | 6/2017 | Takemura et al. |
| 2017/0216564 A1 * | 8/2017 | Ehrenreich ........ A61B 5/15003 |
| 2017/0274182 A1 | 9/2017 | O'Bryan et al. |
| 2017/0368312 A1 | 12/2017 | Rosenberg et al. |
| 2018/0001059 A1 | 1/2018 | Rosenberg et al. |
| 2018/0028800 A1 | 2/2018 | Devgon et al. |
| 2018/0126072 A1 | 5/2018 | Hall et al. |
| 2018/0161543 A1 | 6/2018 | Burkholz |
| 2018/0177445 A1 | 6/2018 | Rogers et al. |
| 2018/0206770 A1 | 7/2018 | Wight et al. |
| 2018/0289921 A1 | 10/2018 | Burkholz |
| 2018/0289922 A1 | 10/2018 | Burkholz |
| 2018/0339132 A1 | 11/2018 | Brunetti |
| 2018/0344983 A1 | 12/2018 | Funk et al. |
| 2019/0021640 A1 | 1/2019 | Burkholz et al. |
| 2019/0044825 A1 | 2/2019 | Vijayakumar et al. |
| 2019/0070400 A1 | 3/2019 | Chelak et al. |
| 2019/0160275 A1 | 5/2019 | Funk et al. |
| 2019/0201668 A1 | 7/2019 | Funk et al. |
| 2019/0275302 A1 | 9/2019 | Devgon et al. |
| 2020/0023166 A1 | 1/2020 | Burkholz et al. |
| 2020/0078565 A1 | 3/2020 | Scherich et al. |
| 2020/0406008 A1 | 12/2020 | Funk et al. |
| 2021/0022655 A1 | 1/2021 | Devgon |
| 2021/0052851 A1 | 2/2021 | Devgon et al. |
| 2021/0196167 A1 | 7/2021 | Vandenbrink et al. |
| 2021/0196940 A1 | 7/2021 | Damarati |
| 2021/0220548 A1 | 7/2021 | Kimball |

FOREIGN PATENT DOCUMENTS

| | | | |
|---|---|---|---|
| KR | 20120003185 | * | 1/2012 |
| WO | 2004082752 A1 | | 9/2004 |
| WO | 2007003874 A1 | | 1/2007 |
| WO | 2014019192 A1 | | 2/2014 |
| WO | 2014019200 A1 | | 2/2014 |
| WO | 2016081008 A1 | | 5/2016 |
| WO | WO-2016185949 A1 * | 11/2016 | ........ A61M 25/0017 |
| WO | 2017117997 A1 | | 7/2017 |

OTHER PUBLICATIONS

English-language machine translation of WO-2016185949-A1, pp. 1-22, 2016 (Year: 2016).*

Machine Translation of CN 104902856, Patent Translate, pp. 1-11, printed on Mar. 20, 2023 (Year: 2015).*

* cited by examiner

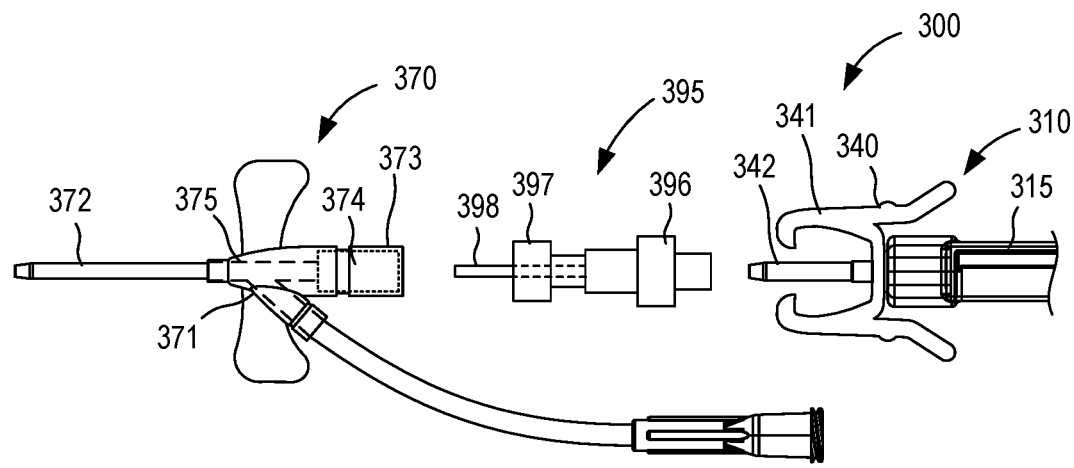
FIG. 8
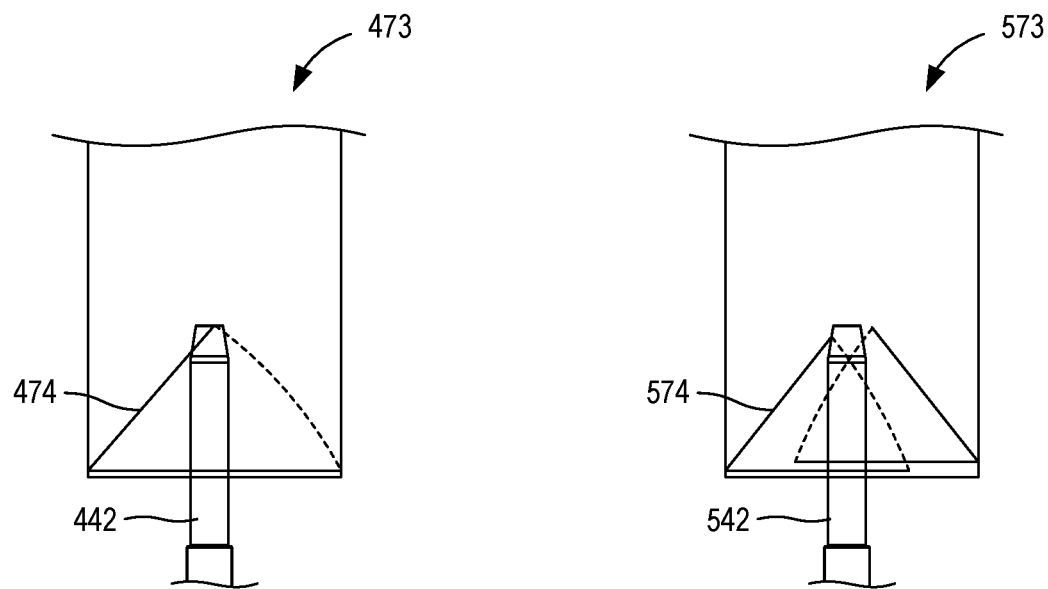
FIG. 9
FIG. 10

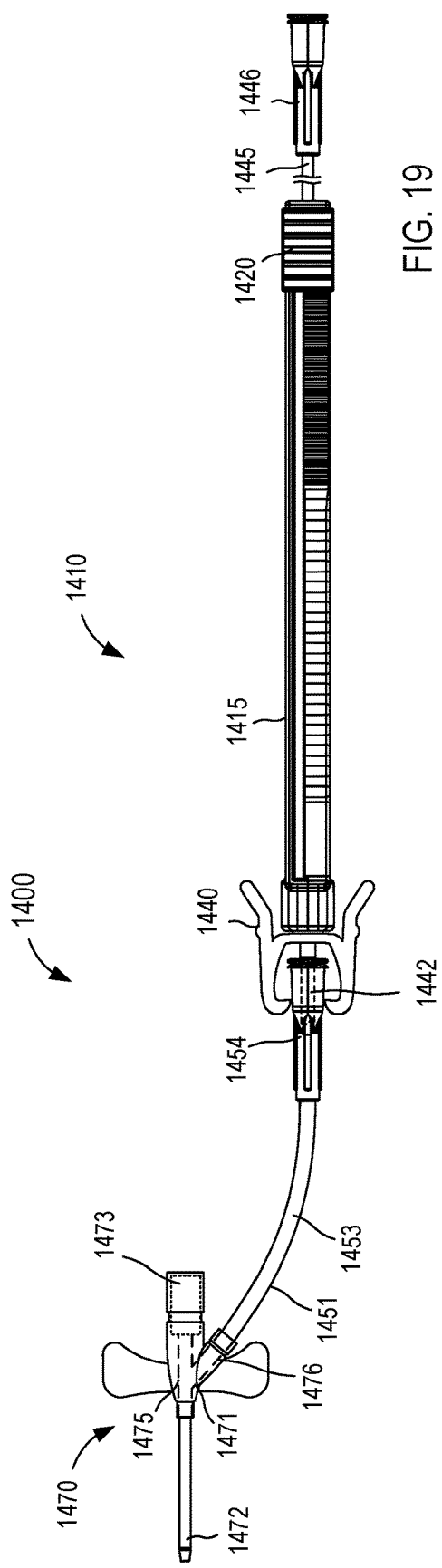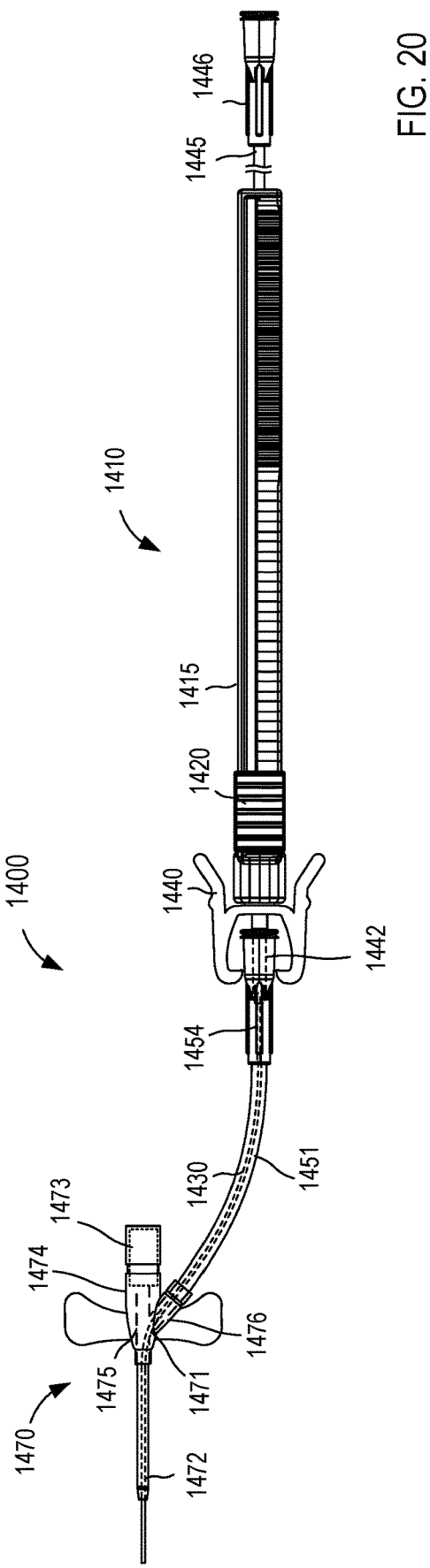

10

```
┌─────────────────────────────────────────────────────────────┐
│ Couple an introducer of a fluid transfer device to a        │
│ proximal port of a hub of a closed system intravenous line  │
│ after a catheter of the closed system intravenous line has  │
│ been positioned within a body of a patient                  │
│                          11                                 │
└─────────────────────────────────────────────────────────────┘
                              │
                              ▼
┌─────────────────────────────────────────────────────────────┐
│ Transition a seal included in the proximal port of the hub  │
│ from a closed state to an open state as a result of the     │
│ coupling of the introducer to the proximal port of the hub  │
│                          12                                 │
└─────────────────────────────────────────────────────────────┘
                              │
                              ▼
┌─────────────────────────────────────────────────────────────┐
│ Transition an actuator of the fluid transfer device from a  │
│ first state to a second state                               │
│                          13                                 │
└─────────────────────────────────────────────────────────────┘
                              │
                              ▼
┌─────────────────────────────────────────────────────────────┐
│ Advance a catheter of the fluid transfer device from a      │
│ first position in which the catheter is disposed within the │
│ introducer to a second position in which the catheter       │
│ extends through the seal such that a distal end surface of  │
│ the catheter is distal to the catheter of the closed system │
│ intravenous line                                            │
│                          14                                 │
└─────────────────────────────────────────────────────────────┘
```

FIG. 29

DEVICES AND METHODS FOR PHLEBOTOMY THROUGH A CLOSED SYSTEM INTRAVENOUS CATHETER

CROSS-REFERENCE TO RELATED APPLICATIONS

This application claims priority to and the benefit of U.S. Provisional Patent Application Ser. No. 62/738,200 entitled, "Devices and Methods for Phlebotomy Through a Closed System Intravenous Catheter," filed Sep. 28, 2018, the disclosure of which is incorporated herein by reference in its entirety.

This application also claims priority to and the benefit of U.S. Provisional Patent Application Ser. No. 62/842,918 entitled, "Devices and Methods for Phlebotomy Through a Closed System Intravenous Catheter," filed May 3, 2019, the disclosure of which is incorporated herein by reference in its entirety.

BACKGROUND

The embodiments described herein relate generally to fluid transfer medical devices. More particularly, the embodiments described herein relate to devices and methods for transferring fluid to or from a patient through a placed peripheral intravenous catheter.

The typical hospitalized patient encounters a needle every time a doctor orders a lab test. The standard procedure for blood extraction involves using a metal needle ("butterfly needle") to "stick" patients' veins in their arms or hands. Blood drawing is a manual, labor-intensive process, with the average patient requiring hours of direct skilled labor during a typical hospital stay. This needle stick is not only painful and a major source of patient dissatisfaction, but the nurses or specialized blood drawing personnel (phlebotomists) often have difficulty finding the vein in approximately 10-25% of patients (referred to as Difficult Intravenous Access ("DVA") patients or more commonly as "tough stick" patients), resulting in multiple, painful "stick" attempts. This results in significantly higher material and labor costs (needles and tubing must be disposed of after every attempt) and increased patient pain and bruising.

The current process for drawing blood is inefficient, taking on average 7-10 minutes, and more than 21 minutes for 10% of patients. If superficial veins are not readily apparent, blood can be forced into the vein by massaging the arm from wrist to elbow, tapping the site with the index and middle finger, applying a warm, damp washcloth to the site for 5 minutes, or by lowering the extremity over the bedside to allow the veins to fill. Each of these methods is time consuming and therefore costly.

Peripheral IV catheters (PIVs) are inserted into most patients while they are hospitalized and can be maintained in the patient for an extended period. PIVs, however, are generally used for infusing fluids and medications and are not designed for blood extraction procedures. The failure rates for aspiration can reach 40-75% when PIVs have been left inserted for more than a day. Blood extracted from PIVs is often hemolyzed, defined as the rupture of red blood cells and the release of their contents into surrounding fluid, resulting in a discarded sample and a need to repeat the blood collection. In addition, blood extracted from PIVs is often diluted or contaminated with saline solution or other infusates if, for example, proper waste methodologies were not followed or were only partially followed.

Several barriers can contribute to the shortcomings of extracting blood through a PIV. Some such barriers can be, for example, a narrowing or collapse of the PIV catheter during aspiration; a buildup of debris (e.g., fibrin/platelet clots) occluding a portion of the catheter or a portion of the vein or vessel in which the catheter is inserted (particularly with longer indwelling times); a "suction cup" effect, in which the negative pressure created by aspiration through the catheter and the possible curved path of a vein results in the tip of the catheter adhering to the wall of the vein; negative pressure increases in the vein sufficient to rupture the vein wall (i.e., "blowing the vein"); reduction of blood flow passing the PIV tip because a portion of the PIV is occluding a portion of the vein or vessel; poor or zero flow of blood in the vein or vessel due to vessel spasm or a vessel wall becoming edematous due to mechanical and/or chemical irritation from the presence of the PIV and/or infusates; and/or the like.

Some known devices have been developed to enable blood aspiration through an indwelling (i.e., placed) PIV. Some PIVs, however, are arranged as a "closed system," which may present challenges for blood draw devices to access the vein through the PIV. For example, some known PIVs include an IV hub or body, which is maintained outside the body and is attached to a relatively soft IV catheter, which is at least partially inserted into the body. Moreover, some closed systems include a device having a rigid needle or trocar that extends through the PIV catheter as it is inserted into the body. Once the catheter is in place in the vein, the rigid needle or trocar is removed and the port through which it extended re-seals. In such devices, fluids and/or medications can be delivered to the patient through a second port of the PIV. The second port of such closed system PIVs, however, is generally not configured for use with some known devices and/or in some known methods that address at least some of the shortcomings associated with blood aspiration through an indwelling PIV.

Thus, a need exists for systems and methods for phlebotomy through a "closed system" peripheral intravenous catheter and/or other similar devices.

SUMMARY

Devices and methods for transferring fluid to or from a patient through a placed peripheral intravenous catheter are described herein. In some embodiments, an apparatus includes a catheter, an introducer, and an actuator. The catheter has a proximal end portion and a distal end portion and defines a lumen therethrough. The introducer has a proximal end portion and a distal end portion and defines an inner volume that is configured to movably receive the catheter. The distal end portion of the introducer has a lock that is configured to couple the introducer to a closed system intravenous line at least partially disposed in a body of a patient. The lock is configured to transition a seal of the closed system intravenous line from a closed state to an open state when the lock is coupled to the closed system intravenous line. The actuator is at least partially disposed in the introducer and is coupled to the proximal end portion of the catheter. The actuator is configured to move the catheter between a first position, in which the catheter is disposed within the introducer, and a second position, in which the catheter extends through the seal of the closed system intravenous line such that a distal end surface of the catheter is positioned distal to the closed system intravenous line when the introducer is coupled to the closed system intravenous line.

BRIEF DESCRIPTION OF THE DRAWINGS

FIG. 8 is a top view illustration of a portion of the fluid transfer device, a closed system access device ("PIV"), and an adapter configured to couple the fluid transfer device to the PIV, according to an embodiment.

FIG. 9-14 are schematic illustrations of a portion of a closed system access device receiving a portion of a fluid transfer device, each according to a different embodiment.

FIGS. 19 and 20 are top view illustrations of a fluid transfer device coupled to a side port of a closed system access device according to an embodiment and shown in a first configuration and a second configuration, respectively.

FIG. 29 is a flowchart illustrating a method of using a fluid transfer device with a closed system access device according to an embodiment.

DETAILED DESCRIPTION

Figure 1:
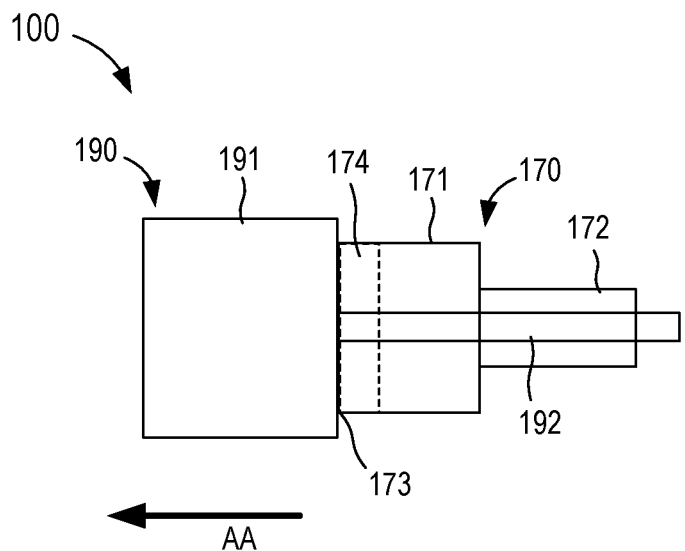
FIG. 1 is a schematic illustration of a closed system access device in a first configuration according to an embodiment.

The embodiments described herein illustrate systems, devices, and methods for aspirating bodily fluid from a patient via an indwelling vascular access device such as a peripheral intravenous line (M). More particularly, the vascular access devices described herein can be similar to or the same as known "closed system" or "bloodless start" access devices. Some such "closed system" access devices include a relatively soft and/or flexible catheter that is configured to be disposed in a lumen (e.g., vein and/or vessel) of a patient. The relatively soft catheter provides the desired amount of flexibility to allow the catheter to bend and/or flex with the anatomy, thereby reducing damage to anatomical structures and increasing patient comfort.

The catheters of such devices, however, may lack the desired amount of rigidity for venipuncture and as such, the access devices are typically combined, coupled, and/or integrated with an insertion device such as a rigid needle, trocar, etc. The insertion device extends through the vascular access device (including the catheter) and provides support to the catheter as the device is inserted into the body. Once the catheter is in a desired position within a vein or other suitable conduit within the body, the insertion device can be retracted and/or removed from the vascular access device, thereby leaving the relatively flexible catheter in the vein. Some such vascular access devices include, for example, a proximal port through which the rigid needle or trocar is inserted. The proximal port of the vascular access devices, in turn, includes a seal, valve, and/or other suitable control device that selectively allows the needle or trocar to place the seal, valve, and/or control device in an open state and/or configuration. Conversely, when the needle or trocar is removed from the proximal port (e.g., after insertion of the catheter into the body of the patient), the seal, valve, and/or control device transitions to a closed state and/or configuration, thereby at least temporarily sealing (e.g., fluidically sealing) or closing the proximal port.

In the embodiments and/or systems described herein, a fluid transfer device can be coupled to, for example, the proximal port of a "closed system" access device after the catheter thereof has been positioned in the vein and the needle (or trocar) of the insertion device has been removed. The devices can be arranged such that the coupling of the fluid transfer device to the access device transitions the seal to an open configuration, thereby allowing the fluid transfer device to withdraw a volume of bodily fluid from the patient, as described in further detail herein.

In some embodiments, an apparatus includes a catheter, an introducer, and an actuator. The catheter has a proximal end portion and a distal end portion and defines a lumen therethrough. The introducer has a proximal end portion and a distal end portion and defines an inner volume that is configured to movably receive the catheter. The distal end portion of the introducer has a lock that is configured to couple the introducer to a closed system intravenous line at least partially disposed in a body of a patient. The lock is configured to transition a seal of the closed system intravenous line from a closed state to an open state when the lock is coupled to the closed system intravenous line. The actuator is at least partially disposed in the introducer and is coupled to the proximal end portion of the catheter. The actuator is configured to move the catheter between a first position, in which the catheter is disposed within the introducer, and a second position, in which the catheter extends through the seal of the closed system intravenous line such that a distal end surface of the catheter is positioned distal to the closed system intravenous line when the introducer is coupled to the closed system intravenous line.

In some embodiments, an apparatus includes a catheter (e.g., a first catheter) and a hub. The first catheter is configured to be disposed within a portion of the body. The hub has a proximal end portion and a distal end portion and defines a central lumen therethrough. The distal end portion of the hub is coupled to the first catheter such that a lumen of the first catheter is in fluid communication with the central lumen of the hub. The distal end portion of the hub has a first port that defines a seal member. The seal is configured to be transitioned from an open state to a closed state after the first catheter is disposed within the portion of the body. The hub has a second port that is coupled to the hub between the proximal end portion and the distal end portion and that is in fluid communication with the central lumen. The hub has a guide defining at least a portion of the central lumen that is configured to engage a second catheter inserted through the second port to guide the second catheter through the central lumen of the hub and into the lumen of the first catheter.

In some embodiments, a method includes coupling an introducer of a fluid transfer device to a proximal port of a hub of a closed system intravenous line after a catheter of the closed system intravenous line has been positioned within a body of a patient. A seal included in the proximal port of the hub is transitioned from a closed state to an open state as a result of the coupling of the introducer to the proximal port of the hub. The seal defines an opening when in the open state that is in fluid communication with a central lumen of the hub. An actuator of the fluid transfer device is transitioned from a first state to a second state and a catheter of the fluid transfer device is advanced from a first position in which the catheter is disposed within the introducer to a second position in which the catheter extends through the seal such that a distal end surface of the catheter is distal to the catheter of the closed system intravenous line.

In some embodiments, an apparatus includes a catheter, an introducer, and an actuator. The catheter has a proximal end portion and a distal end portion and defines a lumen therethrough. The introducer has a proximal end portion and a distal end portion and defines an inner volume configured to movably receive the catheter. The distal end portion of the introducer has a lock configured to couple the introducer to an indwelling peripheral intravenous line. A portion of the lock is configured to transition a seal of the indwelling peripheral intravenous line from a closed state to an open state when the lock is coupled to the indwelling peripheral intravenous line. The actuator is at least partially disposed in the introducer and is coupled to the proximal end portion of the catheter. The actuator is configured to be moved relative to the introducer to move the catheter between a first position, in which the catheter is disposed within the introducer, and a second position, in which a distal end portion of the catheter is distal to the introducer seal of the indwelling peripheral intravenous line such that at least a portion of the catheter extends through the indwelling peripheral intravenous line when the introducer is coupled to the peripheral intravenous line.

As used in this specification, the singular forms "a," "an," and "the" include plural referents unless the context clearly dictates otherwise. Thus, for example, the term "a member" is intended to mean a single member or a combination of members, "a material" is intended to mean one or more materials, or a combination thereof.

As used herein, the words "proximal" and "distal" refer to the direction closer to and away from, respectively, a user who would place the device into contact with a patient. Thus, for example, the end of a device first touching the body of the patient would be the distal end, while the opposite end of the device (e.g., the end of the device being manipulated by the user) would be the proximal end of the device.

In some instances, the words "proximal" or "distal" can be used when describing relative terms and do not necessarily refer to universally fixed positions or directions. For example, a distal end portion of a PIV catheter can be inserted into a vein of a patient's forearm while a proximal end portion of the PIV catheter can be substantially outside of the body. Veins, however, carry a flow of oxygen-poor blood from distal portions of the body back to the heart and, as a result, PIV catheters are generally inserted into a vein such that a distal tip of the PIV catheter is disposed within the vein in a position proximal to the insertion point (e.g., extending relative to the vein in a proximal direction). Thus, a distal position relative to the PIV catheter can refer to, for example, a proximal position relative to the vein (e.g., closer to the heart).

As used herein, the term "stiffness" relates to an object's resistance to deflection, deformation, and/or displacement by an applied force. Stiffness can be characterized in terms of the amount of force applied to the object and the resulting distance through which a first portion of the object deflects, deforms, and/or displaces with respect to a second portion of the object. When characterizing the stiffness of an object, the deflected distance may be measured as the deflection of a portion of the object different from the portion of the object to which the force is directly applied. Said another way, in some objects, the point of deflection is distinct from the point where force is applied.

Stiffness is an extensive property of the object being described, and thus is dependent upon the material from which the object is formed as well as certain physical characteristics of the object (e.g., shape and boundary conditions). For example, the stiffness of an object can be increased or decreased by selectively including in the object a material having a desired modulus of elasticity, flexural modulus, and/or hardness. The modulus of elasticity is an intensive property of (i.e., is intrinsic to) the constituent material and describes an object's tendency to elastically (i.e., non-permanently) deform in response to an applied force. A material having a high modulus of elasticity will not deflect as much as a material having a low modulus of elasticity in the presence of an equally applied stress. Thus, the stiffness of the object can be increased, for example, by introducing into the object and/or constructing the object of a material having a high modulus of elasticity.

Similarly, a material's hardness is an intensive property of the constituent material and describes the measure of how resistant the material is to various kinds of permanent shape change when a force is applied. In discussing the hardness and the subsequent effect on the stiffness of a catheter, the Shore durometer scale is generally used. There are several scales for durometers with two commonly used in describing plastics, polymers, elastomers, and/or rubbers, namely, type A and type D, where type A is generally used for softer materials and type D is generally used for harder materials. The Shore durometer of a material is denoted by a number between 0 and 100, with higher numbers indicating a harder material, followed by the type of scale. For instance, a first material can be measured as having a Shore durometer of 40 Shore A and a second material can be measured as having a Shore durometer of 20 Shore D. Therefore, according to the Shore durometer scale, the second material is harder and thus, more stiff than the first material.

As used herein, the terms "about" and "approximately" generally mean plus or minus 10% of the value stated. For example, about 0.5 would include 0.45 and 0.55, about 10 would include 9 to 11, about 1000 would include 900 to 1100, etc. The term "substantially" when used in connection with values, shapes, and/or geometric structures or relationships is intended to convey that the value, shape, structure, and/or relationship so defined is nominally the value, shape, structure, and/or relationship. As one example, a member that is described as being "substantially linear" is intended to convey that, although linearity of the member is desirable, some non-linearity can occur in a "substantially linear" member. Such non-linearity can result from manufacturing tolerances, or other practical considerations (such as, for example, a pressure, and/or force applied to the member). Thus, a geometric construction modified by the term "substantially" may include such geometric properties within a tolerance of plus or minus 5% of the stated geometric construction. For example, a "substantially linear" an axis or centerline of the member may be within plus or minus 5% of being linear. As another example, two values that are described as being "substantially equal" is intended to convey that, while equality is desirable, some inequality may occur in when equating two "substantially equal" values. Thus, two values are "substantially equal" when an amount of inequality therebetween is below an acceptable tolerance (e.g., plus or minus 5%).

The embodiments described herein and/or portions thereof can be formed or constructed of one or more biocompatible materials. In some embodiments, the biocompatible materials can be selected based on one or more properties of the constituent material such as, for example, stiffness, toughness, durometer, bioreactivity, etc. Examples of suitable biocompatible materials include metals, glasses, ceramics, or polymers. Examples of suitable metals include pharmaceutical grade stainless steel, gold, titanium, nickel, iron, platinum, tin, chromium, copper, and/or alloys thereof. A polymer material may be biodegradable or non-biodegradable. Examples of suitable biodegradable polymers include polylactides, polyglycolides, polylactide-co-glycolides (PLGA), polyanhydrides, polyorthoesters, polyetheresters, polycaprolactones, polyesteramides, poly(butyric acid), poly(valeric acid), polyurethanes, and/or blends and copolymers thereof. Examples of non-biodegradable polymers include nylons, polyesters, polycarbonates, polyacrylates, polymers of ethylene-vinyl acetates and other acyl substituted cellulose acetates, non-degradable polyurethanes, polystyrenes, polyvinyl chloride, polyvinyl fluoride, poly(vinyl imidazole), chlorosulphonate polyolefins, polyethylene oxide, and/or blends and copolymers thereof.

The embodiments herein are generally described as being used, for example, to facilitate the aspiration of a volume of bodily fluid (e.g., blood) from a patient. It should be understood, however, that the embodiments and/or devices are not limited to such uses and/or procedures. For example, in some instances, the embodiments and/or devices can facilitate the aspiration of bodily fluid including but not limited to, blood, cerebrospinal fluid, urine, bile, lymph, saliva, synovial fluid, serous fluid, pleural fluid, amniotic fluid, mucus, vitreous, air, and the like, or any combination thereof. In other instances, the embodiments and/or devices can be used to facilitate the delivery of one or more fluids from a fluid source to the patient. In still other instances, the embodiments and/or devices can be used to facilitate any suitable procedure or the like involving catheterization of a target region in the body. Moreover, the embodiments and/or devices are not limited to transferring fluids to or from a patient and can be used, for example, to facilitate the process of gaining access to a target region in the body for any suitable purpose. While at least some of the devices are described herein as being used with and/or coupled to a PIV in order to transfer fluid to or from a patient, it should be understood that such use is presented by way of example only and not limitation. Furthermore, it should be understood that reference to "a patient" need not be limited to a human patient. For example, any of the devices described herein can be used in any suitable procedure performed on an animal (e.g., by a veterinarian and/or the like).

Figure 2:
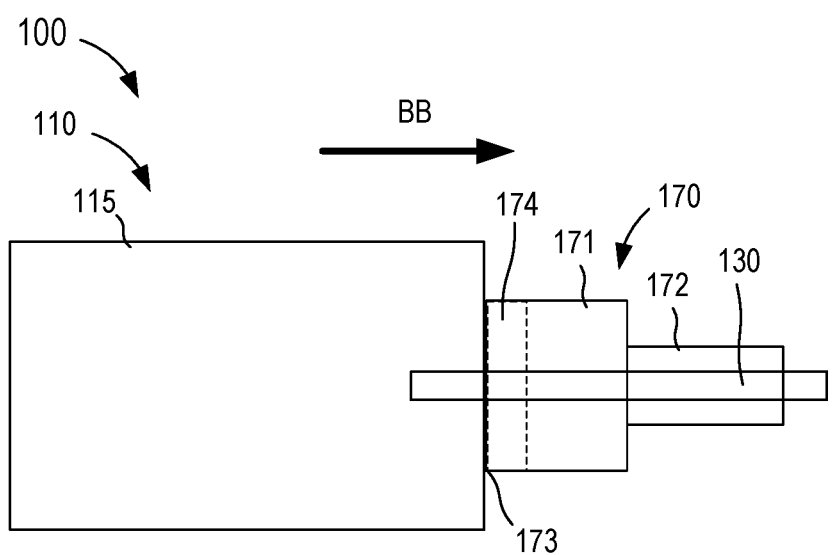
FIG. 2 is a schematic illustration of a fluid transfer device coupled to the closed system access device according to an embodiment.

FIGS. 1 and 2 are schematic illustrations of a closed system access device 100 according to an embodiment. The closed system access device 100 includes an access device 170 that can be coupled to an insertion device 190 (shown in FIG. 1) and/or a fluid transfer device 110 (shown in FIG. 2). As shown in FIG. 1, the access device 170 and the insertion device 190 can collectively form a "closed system" access device 100. The closed system access device 100 can be substantially similar to, for example, known closed system access devices. In some embodiments, the access device 170 and the insertion device 190 can be pre-assembled and sterilized during one or more manufacturing processes and provided to an end user as an integrated closed system (i.e., the closed system access device 100).

In this example, the access device 170 can be any suitable device configured to be at least partially inserted or disposed within a portion of the body. For example, the access device 170 can be a known peripheral intravenous line (PIV) or the like configured to be percutaneously inserted into a portion of the body. In some instances, the access device 170 (e.g., PIV) can be at least partially disposed within a vein of a patient via a venipuncture event or the like, as described in further detail herein.

The access device 170 includes a hub 171 and a catheter 172. The hub 171 can be any suitable device, mechanism, and/or member configured to allow access to a lumen of the catheter 172. In some embodiments, the hub 171 of the access device 170 can include a proximal port 173 or the like, which includes a seal 174 configured to selectively allow access to the catheter 172. Moreover, the hub 171 of the access device can include one or more additional ports arranged in any suitable configuration that can be used to transfer fluids to or from the patient (e.g., a port other than the proximal port 173, not shown in FIG. 1).

The seal 174 disposed in and/or coupled to the hub 171 can be any suitable shape, size, and/or configuration. In some embodiments, the seal 174 can be a pierceable member, a self-sealing and/or self-healing member, a valve, a membrane, a split septum, and/or any other suitable member. In some embodiments, the seal 174 can be and/or can form at least a part of a needle-free connector. For example, the proximal port 173 of the hub 171 can be a luer lock (e.g., a male or female luer lock) or the like within which the seal 174 is disposed. In such embodiments, when a corresponding luer lock or other coupling mechanism of a device is coupled to the proximal port 173, a portion of the corresponding luer lock or other coupling mechanism can be configured to engage the seal 174 to transition the seal 174 from the substantially sealed or closed state and/or configuration to the open state and/or configuration. In some embodiments, the proximal port 173 and/or the seal 174 can form a needle-free connector similar to any suitable commercially available needle-free connector The catheter 172 of the access device 170 is physically and fluidically coupled to the hub 171. The catheter 172 is formed from a relatively soft material or combination of materials configured to allow the catheter 172 to bend, flex, and/or otherwise reconfigure (e.g., elastically or non-permanently). In some embodiments, such an arrangement can allow the catheter 172 to be disposed in a portion of a patient (e.g., a vein of the patient) for an extended period of time while reducing a likelihood of injury to the patient that may otherwise result from an indwelling rigid device. As stated above, however, the relatively soft and/or flexible catheter 172 is typically unsuitable for percutaneous insertion into a patient without additional support.

Accordingly, the access device 170 is pre-assembled with the insertion device 190 (thereby collectively forming the closed system access device). As shown in FIG. 1, the insertion device 190 includes a body 191 and an insertion member 192 such as a rigid needle, trocar, or the like. The body 191 of the insertion device 190 can be coupled to the access device 170 (e.g., to the proximal port 173) such that the insertion member 192 extends through the hub 171 and the catheter 172. The coupling of the access device 170 and the insertion device 190 is such that the seal 174 of the access device 170 is placed in an open state and/or configuration by the insertion member 192 extending therethrough. In other words, when the insertion device 190 is coupled to the access device 170, the insertion member 192 extends through the seal 174 and/or otherwise places the seal 174 in the open state and/or configuration. As described in further detail herein, when the insertion device 190 is removed from the access device 170, the seal 174 can be configured to transition from the open state to a closed or sealed state.

The closed system access device collectively formed by the access device 170 and the insertion device 190 can be substantially similar to known closed system access devices such as, for example, closed system IVs or the like. As such, a user can manipulate the closed system access device to perform a venipuncture event in which the insertion member 192 pierces the skin of the patient and a wall of a vein. With the insertion member 192 at least partially disposed in the catheter 172 of the access device 170, inserting the insertion member 192 into the vein of the patient similarly inserts at least a portion of the catheter 172 into the vein. Once a desired portion of the catheter 172 is positioned in the vein, the insertion device 190 can be retracted and/or removed from the access device 170 (indicated by the arrow AA in FIG. 1), leaving the relatively flexible catheter 172 in the vein. When the insertion device 190 is removed from the access device 170, the seal 174 disposed in the hub 171 of the access device 170 can transition from the open state to the closed state, thereby sealing a portion of the hub 171 (e.g., the proximal port 173). With the access device 170 placed in the patient and with the seal 174 in the closed or sealed state, fluids can be transferred to or from the patient via one or more additional or other ports or the like (e.g., a port other than the proximal port 173, not shown in FIG. 1). Thus, the access device 170 and the insertion device 190 can collectively form a closed system IV, which can be substantially similar to some known closed system IVs.

FIG. 2 illustrates a fluid transfer device 110 that is configured to couple to the access device 170 once the access device 170 is placed in the patient and the insertion device 190 is removed. The fluid transfer device 110 can be any suitable device configured to transfer fluid to or from the patient via the placed or indwelling access device 170. For example, the fluid transfer device 110 can be substantially similar to any of those described herein with reference to specific embodiments.

As shown, the fluid transfer device 110 can include at least an introducer 115 and a catheter 130. The introducer 115 can be any suitable shape, size, and/or configuration. In some embodiments, the introducer 115 can include a proximal end portion configured to couple to the hub 171 of the access device 170 and to transition the seal 174 of the hub 171 from the closed or sealed state to the open state. For example, in some embodiments, the proximal end portion of the introducer 115 can include a lock, coupler, engagement member, and/or the like that can engage the seal 174 when the introducer 115 is coupled to the hub 171 of the access device 170. More particularly, in some embodiments, the proximal end portion of the introducer 115 can include a lock configured as, for example, a male or female luer lock (e.g., a slip luer or a locking luer). In other embodiments, the proximal end portion of the introducer 115 can include a lock similar to any of those described herein with reference to specific embodiments.

The catheter 130 can be any suitable shape, size, and/or configuration. In some embodiments, the catheter 130 can be transitioned and/or moved from a first state, configuration, and/or position, in which the catheter 130 is disposed within the introducer 115, to a second state, configuration, and/or position, in which at least a portion of the catheter 130 extends distal to the introducer 115. More specifically, when the fluid transfer device 110 is coupled to the access device 170 and the seal 174 is placed in its open state and/or configuration, the catheter 130 of the fluid transfer device 110 can be transitioned and/or advanced to its second state, configuration, and/or position, as indicated by the arrow BB in FIG. 2. As such, at least a portion of the catheter 130 can be advanced distal to the introducer 115 and can extend through the seal 174, the hub 171, and the catheter 172 of the access device 170. For example, in some embodiments, the catheter 130 can be advanced to its second state, configuration, and/or position such that a distal end portion of the catheter 130 of the fluid transfer device 110 is distal to a distal end portion of the catheter 172 of the access device 170 and thus, disposed in the vein of the patient. In other embodiments, the catheter 130 of the fluid transfer device 110 need not extend beyond the catheter 172 of the access device 170.

In some embodiments, the fluid transfer device 110 can be coupled to the access device 170 in a substantially similar manner as the insertion device 190. Such an arrangement can allow a portion of the fluid transfer device 110 to selectively engage a portion of the hub 171 of the access device 170 to transition the seal 174 from its closed state to its open state. The transitioning of the seal 174 to the open state and/or configuration, in turn, can allow the catheter 130 of the fluid transfer device 110 to be advanced through the access device 170 (i.e., the hub 171 and the catheter 172) already placed within the vein of the patient. Thus, the fluid transfer device 110 can be used with, for example, some known closed system access devices to transfer fluid to or from a patient via at least a portion of the closed system access device (e.g., the access device 170) pre-placed within the patient.

Figure 3:
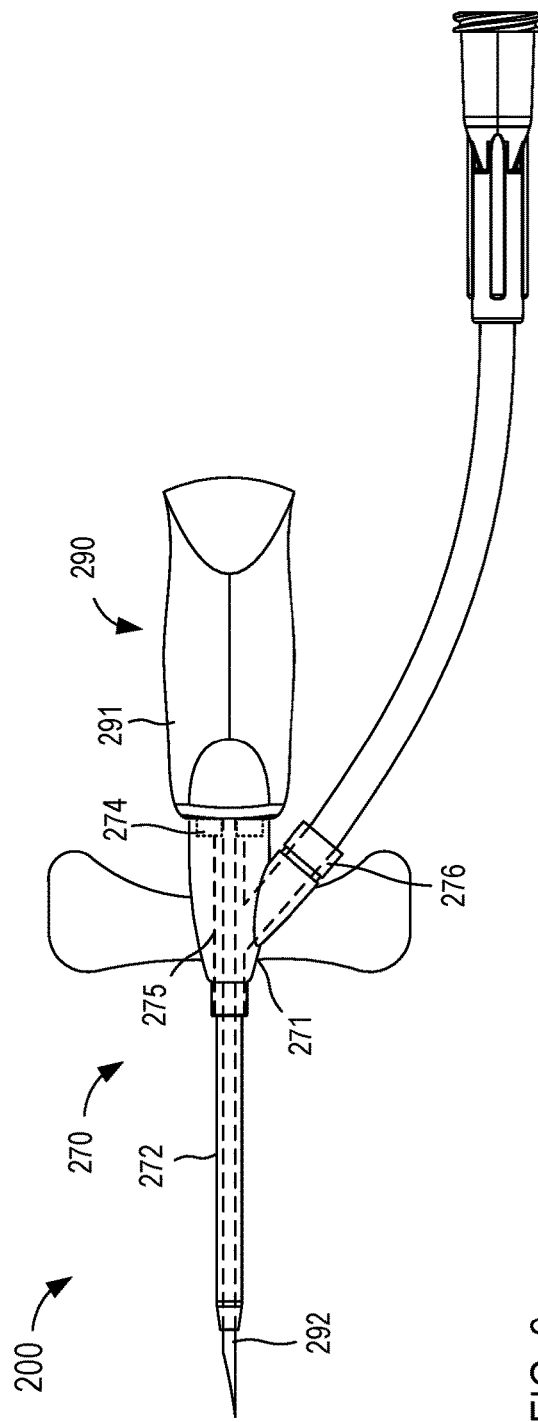
FIGS. 3 and 4 are schematic illustrations of a closed system access device ("PIV") in a first configuration and a second configuration, respectively, according to an embodiment.
Figure 4:
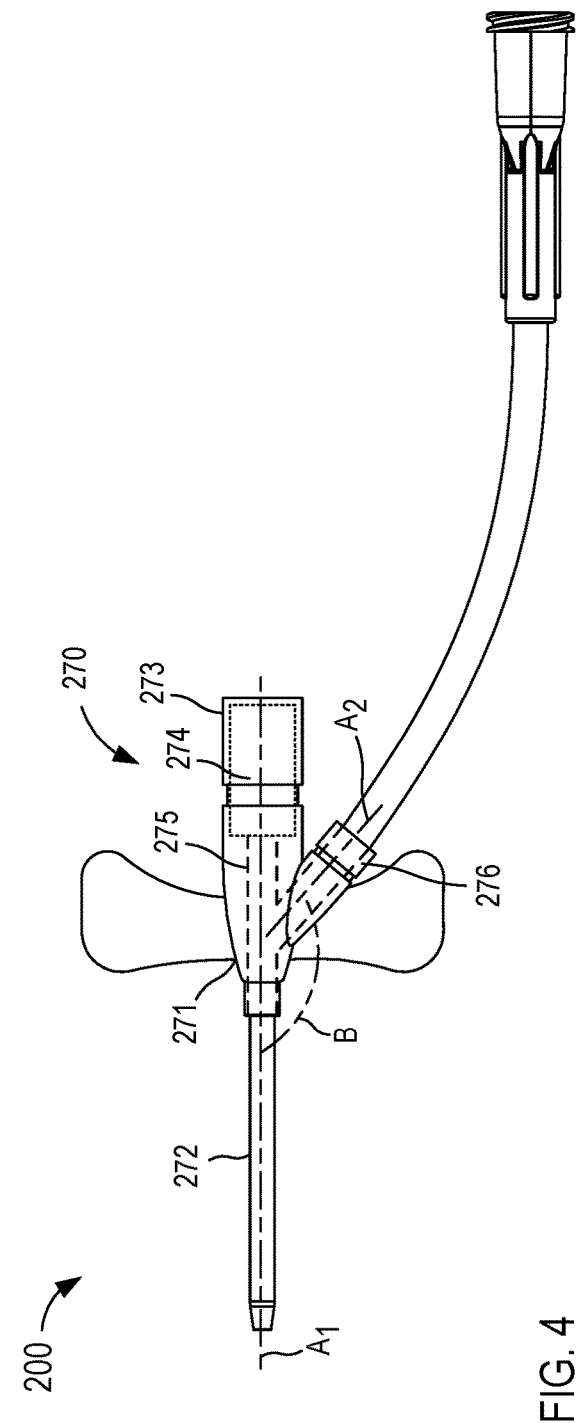

FIGS. 3 and 4 are schematic illustrations of a closed system access device 200 in a first configuration and a second configuration, according to an embodiment. The closed system access device 200 includes an access device 270 that can be coupled to and/or integrated with an insertion device 290 (FIG. 3). As shown in FIG. 3, the access device 270 and the insertion device 290 can collectively form a "closed system" access device 200. The closed system access device 200 can be substantially similar to, for example, known closed system access devices and/or the closed system access device 100 described above with reference to FIGS. 1 and 2. In some embodiments, the access device 270 and the insertion device 290 can be pre-assembled and sterilized during one or more manufacturing processes and provided to an end user as an integrated closed system (i.e., the closed system access device 200).

In this example, the access device 270 can be any suitable device configured to be at least partially inserted or disposed within a portion of the body. For example, the access device 270 can be a known peripheral intravenous line (PIV) or the like configured to be percutaneously inserted into a portion of the body. In some instances, the access device 270 (e.g., PIV) can be at least partially disposed within a vein of a patient via a venipuncture event or the like, as described in further detail herein.

The access device 270 includes a hub 271 and a catheter 272. The hub 271 can be any suitable device, mechanism, and/or member configured to allow access to a lumen of the catheter 272. In some embodiments, the hub 271 of the access device 270 can include a proximal port 273 or the like (see e.g., FIG. 4) and a side port 276 or the like. The hub 271 can define a lumen 275 extending along and/or in the direction of an axis $A_1$ between the catheter 272 and the proximal port 273 (FIG. 4). The proximal port 273 includes a seal 274 configured to selectively allow access to a lumen 275 defined by the hub 271. In other words, when the seal 274 is in an open configuration or state, the lumen 275 of the hub 271 can be accessed via the proximal port 273 and when the seal 274 is in a closed configuration and/or state, the access to the lumen 275 of the hub 271 via the proximal port 273 is blocked and/or prevented.

The seal 274 disposed in the proximal port 273 of the hub 271 can be any suitable shape, size, and/or configuration. In some embodiments, the seal 274 can be pierceable member, a self-sealing and/or self-healing member, a valve, a split septum, a membrane, a needle-free connector or valve, and/or any other suitable member. In some embodiments, the seal 274 can be similar to and/or substantially the same as the seal 174 described above with reference to FIG. 1. In some embodiments, the seal 274 can be configured to form a substantially fluid tight seal when in a closed state or configuration that substantially prevents a flow of fluid through the proximal port 273 (e.g., in either direction). In addition, when the insertion device 290 is coupled to the access device 270, the seal 274 can be configured to form a substantially fluid tight seal between, for example, an inner surface of the hub 271 (and/or an inner surface of the seal 274) and an outer surface of a portion of the insertion device 290, as described in further detail herein.

In some embodiments, the seal 274 can be configured to maintain a fluid tight seal under any suitable pressure conditions. For example, in some instances, after placement of the catheter 272 and removal of the insertion device 290, a high-pressure flow of fluid can be transferred to the patient via the side port 276 of the access device 270 (e.g., during power infusion and/or any other fluid delivery such as low-power or low-pressure fluid delivery, high-power or high-pressure fluid delivery, and/or the like). In some such instances, the seal 274 can be configured to maintain a substantially fluid tight seal and/or can otherwise remain in a substantially sealed or closed state or configuration when a pressure within the lumen 275 of the hub 271 (e.g., a positive pressure) reaches 100 pounds per square inch (psi), 200 psi, 300 psi, 400 psi, or more. In some instances, the seal 274 can be configured to maintain a substantially fluid tight seal and/or can otherwise remain in a substantially sealed or closed state or configuration when a fluid is transferred to or from the patient (e.g., via the side port 276). In some instances, the seal 274 can be configured to maintain a substantially fluid tight seal and/or can otherwise remain in a substantially sealed or closed state or configuration during power infusion of a fluid at or near an industry standard pressure of about 325 psi.

As shown in FIGS. 3 and 4, the side port 276 is in fluid communication with the lumen 275 of the hub 271. In general, the side port 276 can be used to transfer fluids to or from the patient after the catheter 272 is placed in a desired position within a portion of the body (e.g., a vein). The side port 276 can disposed in any suitable orientation relative to the hub 271. For example, as shown in FIG. 4, the side port 276 can be coupled to and/or can extend from a side of the hub 271 such that an axis $A_2$ defined by the side port 276 is disposed at and/or otherwise forms a desired angle B with the axis $A_1$ defined by the lumen 275 (e.g., a non-perpendicular angle such as an obtuse angle). While the side port 276 is particularly shown in FIGS. 3 and 4, in other embodiments, the side port 276 can be arranged in any suitable configuration.

The catheter 272 of the access device 270 is coupled to the hub 271. The catheter 272 defines a lumen that is in fluid communication with the lumen 275. As shown in FIG. 4, the lumen of the catheter 272 and the lumen 275 can share the same axis $A_1$ (e.g., the lumen of the catheter 272 and the lumen 275 of the hub 271 are coaxial). The catheter 272 is formed from a relatively soft material or combination of materials configured to allow the catheter 272 to bend, flex, and/or otherwise reconfigure (e.g., elastically or non-permanently). In some embodiments, such an arrangement can allow the catheter 272 to be disposed in a portion of a patient (e.g., a vein of the patient) for an extended period of time while reducing a likelihood of injury to the patient that may otherwise result from an indwelling rigid device. As stated above, however, the relatively soft and/or flexible catheter 272 is typically unsuitable for percutaneous insertion into a patient without additional support.

Accordingly, the access device 270 is pre-assembled with the insertion device 290 (thereby collectively forming the closed system access device 200). As shown in FIG. 3, the insertion device 290 includes a body 291 and an insertion member 292 such as a rigid needle, trocar, or the like. The body 291 of the insertion device 290 can be any suitable shape, size, and/or configuration. In this embodiment, the body 291 of the insertion device can be coupled to the proximal port 273 of the access device 270 such that the insertion member 292 extends through the lumen 275 defined by the hub 271 and through the catheter 272. The coupling of the access device 270 and the insertion device 290 is such that the seal 274 of the access device 270 is placed in an open state and/or configuration by the insertion member 292 extending therethrough. In other words, when the insertion device 290 is coupled to the access device 270, the insertion member 292 extends through the seal 274, thereby placing the seal 274 in the open state and/or configuration (see e.g., FIG. 3). As described above, the seal 274 can be configured to form a substantially fluid tight seal between an inner surface of the hub 271 and an outer surface of the insertion member 292 operable to prevent a flow of fluid therebetween. As described in further detail herein, when the insertion device 290 is removed from the access device 270, the seal 274 can be configured to transition from the open state to a closed or sealed state.

The closed system access device 200 collectively formed by the access device 270 and the insertion device 290 can be substantially similar to known closed system access devices such as, for example, closed system IVs or the like. As such, a user can manipulate the closed system access device to perform a venipuncture event in which the insertion member 292 pierces the skin of the patient and a wall of a vein. In some embodiments, the insertion member 292 can be, for example, a hollow needle or the like that is in fluid communication with a reservoir defined by and/or contained within the body 291 of the insertion device 290 (not shown). In such embodiments, an initial flow of bodily fluid (commonly known as "flashback") can flow through the insertion member 292 and into the reservoir defined by and/or contained within the body 291 of the insertion device 290. In other embodiments, the insertion device 290 need not be configured to collect a flashback flow of bodily fluid resulting from a venipuncture event.

With the insertion member 292 at least partially disposed in the catheter 272 of the access device 270, inserting the insertion member 292 into the vein of the patient similarly inserts at least a portion of the catheter 272 into the vein. Once a desired portion of the catheter 272 is positioned in the vein, the insertion device 290 can be retracted and/or removed from the access device 270 (see e.g., FIG. 4), leaving the relatively flexible catheter 272 in the vein. When the insertion device 290 is removed from the access device 270, the seal 274 disposed in proximal port 273 of the hub 271 can transition from the open state, in which the insertion member 292 extended therethrough, to the closed state, in which the proximal port 273 is fluidically sealed. After placing the access device 270 in the patient and with the seal 274 in the closed or sealed state, fluids can be transferred to or from the patient via the side port 276. Moreover, the seal 274 can be configured to maintain a substantially fluid tight seal throughout a range of pressures (e.g., from a relatively low pressure associated with a pressure within the vein to a relative high pressure associated with high pressure fluid delivery such as 325 psi or more). Thus, the access device 270 and the insertion device 290 can collectively form the closed system access device 200, which can be substantially similar in form and/or function to some known closed system IVs.

As described above with reference to FIGS. 1 and 2, in some embodiments, a fluid transfer device can be used with the closed system access device 200 to, for example, transfer a bodily fluid from the patient to a fluid collection device, container, reservoir, etc. Such a fluid transfer device can have any suitable configuration and/or arrangement. For example, in some embodiments, such a fluid transfer device can be substantially similar to any of those described in U.S. Pat. No. 10,076,272 entitled, "Systems and Methods for Phlebotomy Through a Peripheral IV Catheter," filed Aug. 26, 2014 (referred to as the '272 patent); U.S. Pat. No. 10,300,247 entitled, "Devices and Methods for Fluid Transfer Through a Placed Peripheral Intravenous Catheter," filed Feb. 3, 2016 (referred to as the '247 patent); and/or U.S. Pat. No. 9,744,344 entitled, "Devices and Methods for Catheter Placement Within a Vein," filed Jun. 30, 2016 (referred to as the '344 patent), the disclosures of which are incorporated herein by reference in their entireties.

Figure 5:
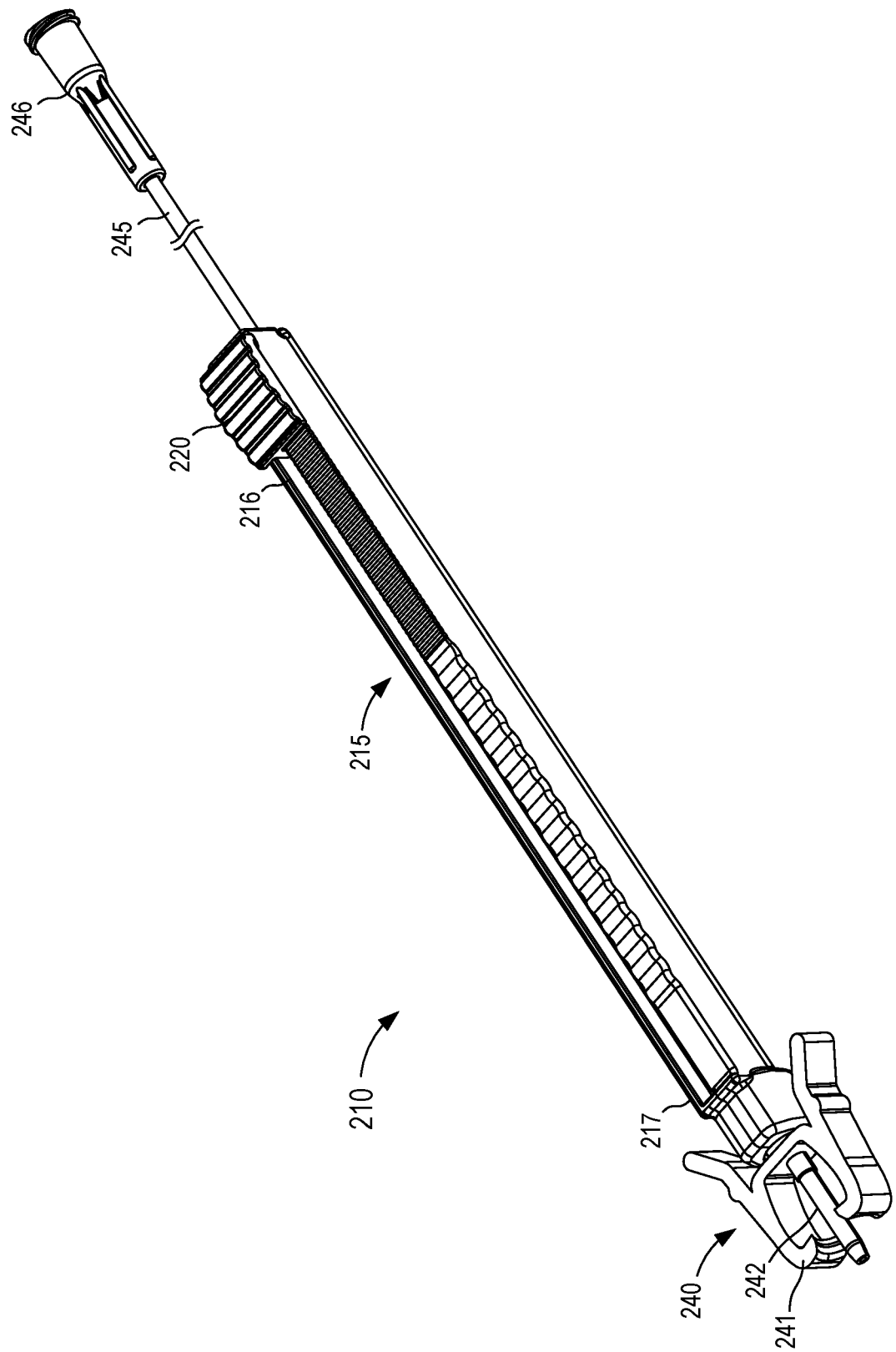
FIG. 5 is a perspective view of a fluid transfer device according to an embodiment.

By way of example, FIG. 5 is a perspective view of a fluid transfer device 210 according to an embodiment. As described in further detail herein, the fluid transfer device 210 can be used with the closed system access device 200 to transfer bodily fluid from the patient to one or more fluid collection devices, containers, reservoirs, etc. More particularly, in some instances, the access device 270 can be inserted into a patient such that the catheter 272 is at least partially disposed within a vein. In such instances, the fluid transfer device 210 can be used with (e.g., coupled to) the access device 270 and manipulated to withdraw a volume of blood from the vein of the patient into one or more fluid collection devices, reservoirs, containers, etc.

Figure 6:
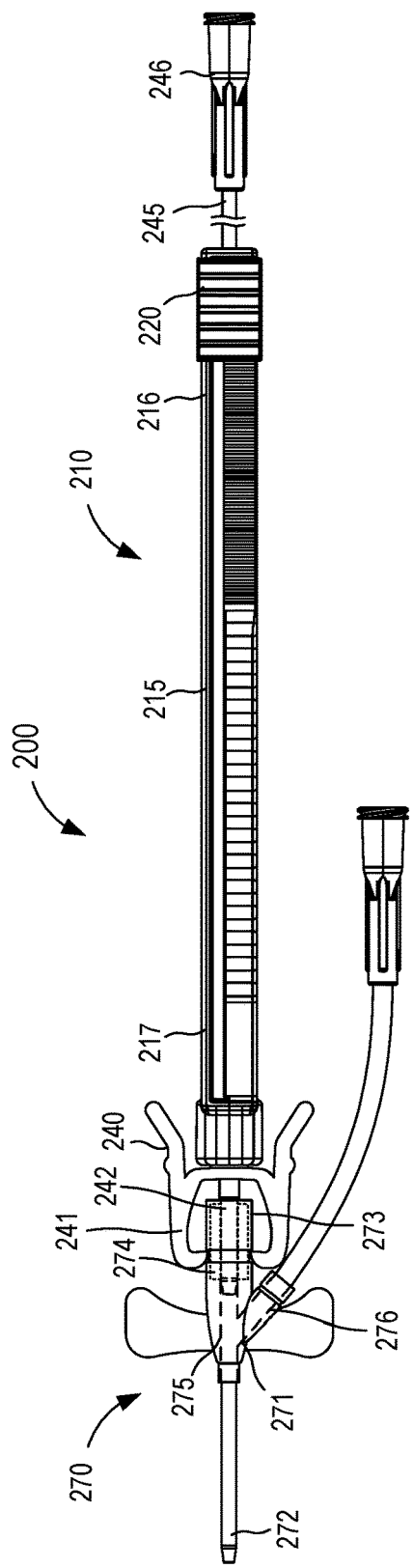
FIGS. 6 and 7 are top view illustrations of the fluid transfer device or FIG. 5 coupled to the PIV of FIG. 3 and disposed in a first configuration and a second configuration, respectively.
Figure 7:
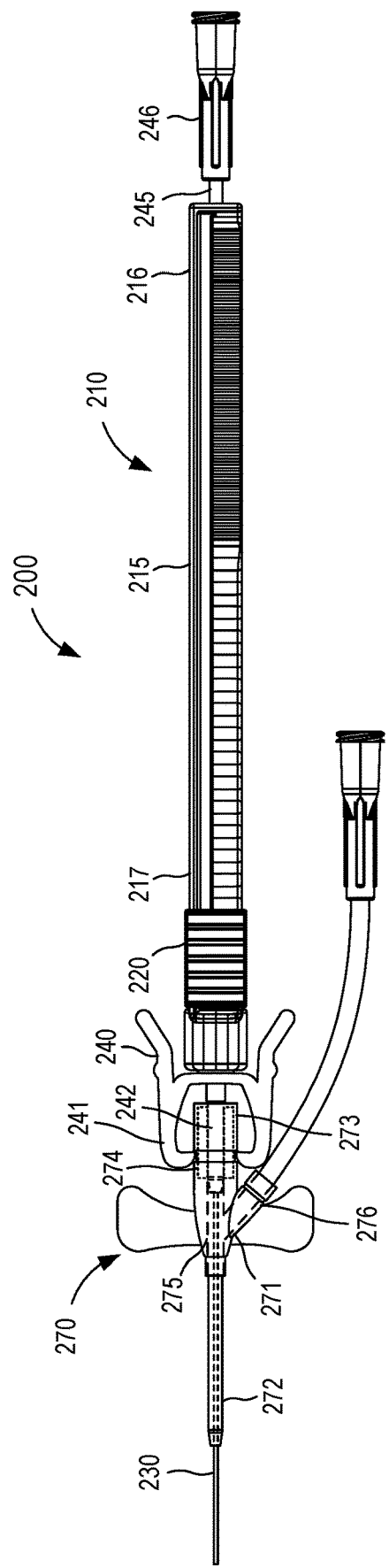

As shown in FIGS. 5-7, the fluid transfer device 210 includes at least an introducer 215, an actuator 220, and a catheter 230. In some embodiments, the transfer device 210 can be similar to and/or substantially the same as any of those described in the '247 patent, the disclosure of which is incorporated above. As such, some aspects of the transfer device 210 are not described in detail herein and should be considered substantially similar to such aspects of the transfer devices described in the '247 patent unless explicitly expressed otherwise.

The introducer 215 of the transfer device 210 can be any suitable configuration. For example, in some embodiments, the introducer 215 can be an elongate member having a substantially circular or semi-circular cross-sectional shape. Although not shown, the introducer 215 defines an inner volume within which at least a portion of the catheter 230 and at least a portion of the actuator 220 are movably disposed. As described in further detail herein, prior to use, the catheter 230 can be in a first position, configuration, and/or state in which the catheter 230 is disposed or substantially disposed within the inner volume of the introducer 215. Such an arrangement can, for example, protect the catheter 230 from being physically damaged prior to use and/or protect the catheter 230 from being contaminated by a nonsterile environment. In use, the catheter 230 can be transitioned to a second position, configuration, and/or state in which at least a portion of the catheter 230 is distal to and outside of the introducer 215.

The introducer 215 includes a proximal end portion 216 and a distal end portion 217. The proximal end portion 216 can include an opening or port (not shown) configured to movably receive a portion of the catheter 230 and/or an outlet or secondary catheter 245. The distal end portion 217 of the introducer 215 includes and/or is coupled to a lock 240 configured to physically and fluidically couple the introducer 215 to, for example, the access device 270 (e.g., a PIV or the like), as described in further detail herein.

The catheter 230 of the transfer device 210 is movably disposed within the inner volume defined by the introducer 215 and is coupled to the actuator 220. In some embodiments, the catheter 230 can be moved (e.g., via movement of the actuator 220) between a first position and a second position to transition the transfer device 210 between the first configuration and the second configuration, respectively. More specifically, at least a portion of the catheter 230 is disposed within the inner volume and/or the lock 240 when the catheter 230 is in the first position (FIGS. 5 and 6) and at least a portion of the catheter 230 extends beyond the introducer 215 and lock 240 to place a distal end of the catheter 230 in a position within the access device 270 or a position distal to the access device 270 when the catheter 230 is in the second position (FIG. 7), as described in further detail herein.

The catheter 230 can be any suitable shape, size, and/or configuration. In some embodiments, the catheter 230 can be substantially similar to the catheters described in detail in the '247 patent. In some embodiments, at least a portion of the catheter 230 can have an outer diameter (e.g., between a 16-gauge and a 26-gauge) that is substantially similar to or slightly smaller than an inner diameter defined by a portion of the lock 240. In this manner, an inner surface of the portion of the lock 240 can guide the catheter 230 as the catheter 230 is moved between the first position and the second position. In some embodiments, such an arrangement can limit and/or can substantially prevent bending, deforming, and/or kinking of the catheter 230 as the catheter 230 is moved between the first position and the second position. In some embodiments, the catheter 230 can have a length that is sufficient to place a distal surface of the catheter 230 in a desired position relative to a distal surface of the access device 270 (e.g., the catheter 272 of the access device 270) when the catheter 230 is in the second position, as described in further detail herein.

The actuator 220 of the transfer device 210 can be any suitable shape, size, and/or configuration. In some embodiments, the actuator 220 can be substantially similar to the actuators described in detail in the '247 patent. For example, the actuator 220 can include a first portion movably disposed within the inner volume and a second portion movably disposed outside of the inner volume of the introducer 215. Although not shown in FIGS. 5-7, the first portion of the actuator 220 (e.g., the portion disposed in the introducer 215) is coupled to the proximal end portion of the catheter 230. The first portion of the actuator 220 can also be coupled to an outlet or secondary catheter 245 such that the catheter 230 and the outlet or secondary catheter 245 are in fluid communication. As described in detail in the '247 patent, the outlet or secondary catheter 245 is configured to extend through the opening and/or port defined by the proximal end portion of the introducer 215. In this manner, a proximal end portion of the catheter 230 and/or the outlet or secondary catheter 245 can be coupled to a fluid reservoir, fluid source, syringe, and/or the like via a coupler 246, which in turn, places the catheter 230 in fluid communication therewith.

As described above, the second portion of the actuator 220 is disposed outside of the introducer 215 and can be engaged by a user to move the actuator 220 relative to the introducer 215. Moving the actuator 220 relative to the introducer 215, in turn, can move the catheter 230 coupled to the first portion of the actuator 220 between the first position and the second position.

The lock 240 included in and/or coupled to the distal end portion 217 of the introducer 215 can be any suitable shape, size, or configuration. In some embodiments, the lock 240 is substantially similar to those described in detail in the '247 patent. As such, the lock 240 can selectively engage and/or contact the access device 270 to couple the introducer 215 thereto, as described in the '247 patent. In the embodiment shown in FIGS. 5-7, the lock 240 includes a set of arms 241 and a proboscis 242. The set of arms 241 can be configured to engage an outer surface of the proximal port 273 of the access device 270 when the lock 240 is coupled thereto. Although described as including the set of arms 241 that are used to couple to the proximal port 273 of the access device 270, in other embodiments, the lock 240 can include and/or can form any suitable coupler or the like configured to couple or attach the transfer device 210 to the access device 270. For example, in some embodiments, a lock of the transfer device 210 can be similar to and/or substantially the same as any of the locks described in the '247 patent. In other embodiments, the lock 240 can include and/or can be configured as a threaded coupler, a slidable collar, one or more engagement members, a male or female luer lock (e.g., a slip luer or a locking luer), and/or any other suitable coupler.

As shown in FIG. 6, the proboscis 242 of the lock 240 extends from the lock 240 in a distal direction (e.g., away from the introducer 215). The proboscis 242 can be configured such that the proboscis 242 is inserted into the proximal port 273 of the access device 270 when the lock 240 is coupled thereto. More specifically, when the lock 240 couples to the proximal port 273, the proboscis 242 can be inserted into the proximal port 273 and in contact with and/or at least partially through the seal 274 disposed in the proximal port 273. That is to say, the proboscis 242 can have a size, shape, and/or arrangement that enables the proboscis 242 to transition the seal 274 from the substantially closed or sealed configuration or state to the open configuration or state when the lock 240 is coupled to the access device 270.

As shown in FIG. 6, in some embodiments, the proboscis 242 can have a length that is sufficient to extend through the entire seal 274 such that a distal end of the proboscis 242 is distal to the seal 274 and disposed within the lumen 275 of the access device 270. In other embodiments, the proboscis 242 need not extend through the entire seal 274. In such embodiments, the proboscis 242 can be partially inserted into the seal 274 a sufficient amount to transition the seal 274 from the closed or seal state to the open state or substantially the open state. In still other embodiments, a distal surface of the proboscis 242 can be configured to engage and/or contact a surface of the seal 274 as the proboscis 242 is inserted into the proximal port 273. In such embodiments, the proboscis 242 can be configured to move, deform, deflect, reconfigure, and/or otherwise transition the seal 274 from the sealed or closed state or configuration to the open state or configuration as the proboscis is advanced to a desired position.

More particularly, in some embodiments, the seal 274 can be configured as and/or can be similar to a needle-free valve or connector that can be reconfigured in response to contact with the proboscis 242 (or any suitable portion of a corresponding locking device). For example, the proboscis 242 may be inserted into the proximal port 273 such that a distal surface of the proboscis 242 contacts a surface of the seal 274. As the lock 240 is secured to the proximal port 273, the proboscis 242 can exert a force on a portion of the seal 274 and/or can otherwise engage the portion of the seal 274, which in turn, can bend, flex, deform, deflect, reconfigure, and/or otherwise transition the seal 274 from the sealed or closed state to the open state. In other words, in some embodiments, coupling the lock 240 of the transfer device 200 to the proximal port 273 can transition the seal 274 to the open state in a manner substantially similar to the seal or valve of some known needle-free connectors when coupled to a corresponding luer lock. Moreover, when the seal 274 is in the open state, a fluid flow path can be defined that places a lumen defined by the proboscis 242 in fluid communication with the lumen 275 of the hub 271.

As shown in FIG. 7, once the lock 240 has coupled the transfer device 210 to the access device 270, the transfer device 210 can be transitioned from a first state to a second state to, for example, transfer a volume of bodily fluid from the patient. For example, as described above, a user (e.g., a doctor, nurse, physician, surgeon, technician, phlebotomist, etc.) can manipulate the closed system access device 200 (e.g., the access device 270 coupled to the insertion device 290, as shown in FIG. 3) to perform venipuncture. As such, the insertion member 292 (e.g., a needle) can puncture the skin of a patient at a cleaned and/or substantially sterilized insertion site to position at least a portion of the insertion member 292 and the catheter 272 in a vein of the patient. Once the catheter 272 is disposed in the vein, the insertion device 290 can be withdrawn from the access device 270 (see e.g., FIG. 4), leaving the relatively flexible catheter 272 in the vein.

With the catheter 272 in a desired position within the vein, a user can manipulate the transfer device 210 to couple the transfer device 210 to the access device 270. As described above, in some embodiments, the lock 240 can be coupled to the proximal port 273 of the access device 270 to couple the transfer device 210 thereto. As shown in FIG. 6, when the lock 240 is coupled to the proximal port 273, the set of arms 241 (or any other suitable coupler or coupling portion of the lock 240) can engage an outer surface of the proximal port 273 to at least temporarily secure the lock 240 to the proximal port 273. In addition, the proboscis 242 of the lock 240 can extend through the proximal port 273 and the seal 274 (or at least a portion thereof), thereby transitioning the seal 274 from the closed state and/or configuration to the open state and/or configuration (or at least a semi-open state and/or configuration). In some embodiments, the seal 274 can be configured to form a substantially fluid tight seal between an inner surface of the access device 270 (or an inner surface of the seal 274) and an outer surface of the proboscis 242. That is to say, the seal 274 seals, closes, and/or occludes the proximal port 273 around the proboscis 242 to limit and/or substantially prevent a flow of fluid outside of the proboscis 242 from flowing through the proximal port 273.

After coupling the transfer device 210 to the access device 270, the user can manipulate the transfer device 210 to transition it from the first configuration and/or state to the second configuration and/or state. For example, in some embodiments, the user can exert a force on the actuator 220 to move the actuator 220 relative to the introducer 215 from a first position (e.g., at or near the proximal end portion 216 of the introducer 215, as shown in FIG. 6) to a second position (e.g., at or near the distal end portion 217 of the introducer 215, as shown in FIG. 7). As described in detail in the '247 patent, the catheter 230 is configured to move or transition with the actuator 220 as the actuator 220 is moved or transitioned from the first position to the second position. More particularly, when the actuator 220 is in a first actuator position (FIG. 6), the catheter 230 can be disposed within the introducer 215 and/or a portion of the lock 240 and proximal to the access device 270. When the actuator 220 is in a second actuator position (FIG. 7), the catheter 230 extends through the proboscis 242, the lumen 275 of the access device 270, and the catheter 272 to place a distal end portion of the catheter 230 of the transfer device 210 in a distal position relative to the distal end portion of the catheter 272 of the access device 270. In other words, the catheter 230 of the transfer device 230 can be advanced and/or transitioned in a manner similar to or substantially the same as the manner described in the '247 patent. Moreover, in some embodiments, the catheter 230 of the transfer device 210 can be placed at a desired position relative to the catheter 272 of the access device, as described in detail in the '344 patent.

Before or after transitioning the catheter 230, the user can couple a fluid reservoir (not shown) to the coupler 246. For example, in some instances, the catheter 230 can be transitioned and/or placed in its second position, configuration, and/or state prior to coupling the fluid reservoir (not shown) to the coupler 246. In some embodiments, coupling the fluid reservoir to the coupler 246 can place the catheter 230 in fluid communication with the fluid reservoir, which in turn can allow bodily fluid to flow from the patient, through the catheter 230 and the secondary or outlet catheter 245 and into the fluid reservoir. In some embodiments, the bodily fluid can flow from the patient to the fluid reservoir in response to a negative pressure produced and/or introduced by coupling the fluid reservoir to the coupler 246 (e.g., the fluid reservoir is evacuated and/or is manipulated to create a negative pressure as with a syringe). Thus, the transfer device 210 can be used to transfer a volume of bodily fluid from the patient to the fluid reservoir coupled thereto. Moreover, the arrangement of the lock 240 can enable the transfer device 210 to be used with a closed system access device (e.g., the access device 270) after the access device (e.g., the access device 270) has been inserted into the patient and the insertion device (e.g., the insertion device 290) has been removed.

While the transfer device 210 is described above with reference to FIGS. 6 and 7 as being coupled to the proximal port 273 of the access device 270, in other embodiments, any suitable coupler, adapter, extension, port, etc. can be coupled between a transfer device and an access device. For example, FIG. 8 illustrates an access device 370, a fluid transfer device 310 (referred to herein as "transfer device"), and an adapter 395, according to an embodiment. The access device 370 can be included in and/or can form a part of a closed system access device 300 (the insertion device is not shown in FIG. 8) that can be substantially similar to the closed system access device 200, described above with reference to FIGS. 3-7. Accordingly, the access device 370 is not described in further detail herein. Similarly, the transfer device 310 can be substantially similar to the transfer device 210, described above with reference to FIGS. 5-7. Thus, the transfer device 310 and/or portions or aspects thereof are not described in further detail herein.

The adapter 395 can be any suitable shape, size, and/or configuration. In some embodiments, the adapter 395 can be similar to some commercially available adapters, connectors, couplers, extension sets, and/or the like. For example, in some embodiments, the adapter 395 can be substantially similar in at least form and/or function to some commercially available adapters suitable for use with needle-free connectors. In other embodiments, the adapter 395 need not be similar to known or commercially available adapters, connectors, couplers, extension sets, etc.

As shown in FIG. 8, the adapter 395 has a proximal end portion 396 and a distal end portion 397. The proximal end portion 396 is configured to be coupled to a lock 340 of the transfer device 310. For example, in some embodiments, the lock 340 of the transfer device 310 can include a set of arms 341 (similar to the set of arms 241) configured to selectively engage an outer surface of the proximal end portion 396 of the adapter 395 to couple the adapter 395 thereto. In addition, a proboscis 342 of the lock 340 (similar to the proboscis 242) can be inserted into the proximal end portion 396 of the adapter 395, as described in further detail herein.

The distal end portion 397 of the adapter 395 is configured to be coupled to a hub 371 of the access device 370 and more specifically, to a proximal port 373 included in and/or formed by the hub 371. As shown in FIG. 8, the distal end portion 397 of the adapter 395 includes an engagement member 398 configured to selectively engage a portion of the access device 370 when the adapter 395 is coupled to the proximal port 373. In some embodiments, the engagement member 398 can be, for example, a relatively rigid or stiff tube such as a metal hypotube, a hard plastic hypotube, an annular or hollow rod, and/or the like. In some embodiments, the engagement member 398 can be substantially hollow and can define a lumen or opening having a size sufficient to receive a catheter of the transfer device 310 therethrough. In some embodiments, the engagement member 398 can have a size and/or shape that is similar to and/or substantially the same as the proboscis 342 of the lock 340. In other embodiments, the engagement member 398 can have any suitable size and/or shape.

As described above, the distal end portion 397 of the adapter 395 is configured to couple to the proximal port 373 of the access device 370. In some embodiments, the distal end portion 397 can include a coupler or the like configured to couple to the proximal port 373. For example, in some embodiments, the distal end portion 397 can include a threaded coupler (e.g., similar to a Luer Lok™), a slidable collar, one or more engagement members, a set of arms (e.g., similar to the set of arms 341 of the lock 340), and/or any other suitable coupler. Moreover, when the distal end portion 397 of the adapter 395 is coupled to the proximal port 373 of the access device 370, the engagement member 398 can extend through the proximal port 373 and at least partially through a seal 374 included in and/or otherwise disposed in the proximal port 373 (e.g., similar to or the same as the seal 274 described above with reference to FIGS. 3-7). As described above with reference to the proboscis 242 of the lock 240, the engagement member 398 can be configured to engage the seal 374 to transition the seal 374 from a substantially sealed or closed state or configuration to a substantially open state or configuration. In some embodiments, the engagement member 398 can extend substantially through the seal 374 to be at least partially disposed within a lumen 375 of the hub 371. In other embodiments, the engagement member 398 need not extend through the entire seal 374.

As described above, the adapter 395 can be used to couple the transfer device 310 to the access device 370, which can then be used to transfer bodily fluid to a fluid reservoir. For example, a user (e.g., a doctor, nurse, physician, surgeon, technician, phlebotomist, etc.) can manipulate the closed system access device 300 (e.g., the access device 370 coupled to an insertion device, not shown in FIG. 8) to perform venipuncture. As such, an insertion member (e.g., a needle) can puncture the skin of a patient at a cleaned and/or substantially sterilized insertion site to position at least a portion of a catheter 372 of the access device 370 in a vein of the patient. Once the catheter 372 is disposed in the vein, the insertion device can be withdrawn from the access device 370, leaving the relatively flexible catheter 372 in the vein.

With the catheter 372 in a desired position within the vein, a user can manipulate the adapter 395 to couple the distal end portion 397 of the adapter 395 to the proximal port 373 of the access device 370. As described above, the engagement member 398 of the adapter 395 can extend through the proximal port 373 and the seal 374 (or at least a portion thereof), thereby transitioning the seal 374 from the closed state and/or configuration to the open state and/or configuration (or at least a semi-open state and/or configuration). As described above, the seal 374 can be configured to seal the proximal port 373 around the engagement member 398 to limit and/or substantially prevent a flow of fluid outside of the engagement member 398 from flowing through the proximal port 373.

Before or after coupling the adapter 395 to the access device 370, the user can manipulate the transfer device 310 to couple the lock 340 of the transfer device 310 to the proximal end portion 396 of the adapter 395. As described above, the set of arms 341 of the lock 340 can selectively engage an outer surface of the adapter 395 to at least temporarily secure or attach the adapter 395 to the transfer device 310. In addition, the proboscis 342 of the lock 340 can be at least partially inserted into the proximal end portion 396 of the adapter 395 when the adapter 395 is coupled to the lock 340 such that the proboscis 342 is placed in fluid communication with the substantially hollow engagement member 398.

After coupling the transfer device 310 to the adapter 395 and the adapter 395 to the access device 370, the user can manipulate the transfer device 310 to transition it from the first configuration and/or state to the second configuration and/or state, as described in detail above with reference to the transfer device 310 shown in FIGS. 5-7. Accordingly, the catheter (not shown) of the transfer device 310 can be moved or transitioned from a first position, in which the catheter can be disposed within an introducer 315 and/or a portion of the lock 340 and proximal to the adapter 395, to a second position, in which the catheter extends through the proboscis 342 of the lock 340, the adapter 395 (including the engagement member 398), the lumen 375 of the access device 370, and the catheter 372 of the access device 370 to place a distal end portion of the catheter of the transfer device 310 in a distal position relative to the distal end portion of the catheter 372 of the access device 370. Moreover, before or after transitioning the catheter, the user can couple a fluid reservoir (not shown) to transfer device 310. As such, when the catheter of the transfer device 310 is in the second state, configuration, and/or position, a flow of bodily fluid can be transferred from the patient, through the transfer device 310, and into the fluid reservoir, as described in detail above with reference to the transfer device 210.

Although not shown in FIG. 8, in some embodiments, the catheter of the transfer device 310 can be configured such that a length of the catheter is sufficient to allow the catheter to be advanced through the adapter 395 and the access device 370. In some embodiments, the adapter 395 can have a relatively short length between the proximal end portion 396 and the distal end portion 397 to ensure that a length of the catheter of the transfer device 310 is sufficient to be placed in a desired position once transitioned to its second state, configuration, and/or position.

While the adapter 395 is specifically illustrated in FIG. 8, it should be understood that the adapter 395 is presented by way of example only and not limitation. For example, in some embodiments, the adapter 395 can have a size, shape, and/or configuration based at least in part on an access device to which the adapter 395 is to be coupled. In such embodiments, the adapter 395 can be sized and/or shaped to be compatible with any suitable access device 370 (e.g., any suitable commercially available access device), thereby making the transfer device 310 compatible with such access devices without altering and/or modifying one or more portions thereof (e.g., the lock 340 or any other portion). For example, in some embodiments, the proximal end portion 396 and/or the distal end portion 397 can include a coupler that can be similar to and/or substantially the same as known male or female luer locks or connectors. In such embodiments, the lock 340 of the transfer device 310 can be configured to couple to the luer lock disposed at the proximal end portion 396 of the adapter 395 as described in detail in the '574 publication incorporated by reference above.

In other embodiments, the transfer device 310 can include a removable or interchangeable lock or coupler that can be removed and/or replaced to accommodate and/or couple to an adapter and/or access device. For example, in some the transfer device 310 can include a male or female luer lock that can be configured to couple to the corresponding luer lock disposed at the proximal end portion 396 of the adapter 395. In some embodiments, including a luer lock or other known coupler or connector at the proximal end portion 396 and/or the distal end portion 397 of the adapter 395 can allow the adapter 395 to couple to one or more devices in a known or predictable manner without a need to modify the devices (e.g., the access device 370, the transfer device 310, and/or any other suitable device).

While the engagement member 398 is described above as being a relatively rigid hypotube or hollow rod configured to at least partially extend through the seal 374, in other embodiments, the engagement member 398 can be similar to or substantially the same as a portion of a luer lock configured to engage or contact, for example, a needle-free valve or connector to transition the needle-free valve or connector from the sealed or closed state to the open state. In other embodiments, the engagement member 398 can be substantially similar in at least form and/or function to the proboscis 342. In still other embodiments, the engagement member 398 (and/or the proboscis 342) can be configured as a blunt cannula and/or the like.

While the access devices 170, 270, and 370 have been particularly described above, in other embodiments, an access device can have any suitable shape, size, and/or configuration and can include any suitable port configured to couple to and/or otherwise accept a lock of a transfer device. For example, FIGS. 9-14 each illustrate a proximal port of an access device included in a "closed system," according to various embodiments. More specifically, FIG. 9 illustrates a proximal port 473 included in and/or formed by a hub of an access device. In some embodiments, the proximal port 473 can be configured to receive a portion of a transfer device and/or adapter, for example, after a catheter of the access device has been placed in a vein of a patient and an insertion device has been removed from the access device, as described above with reference to the access devices 170, 270, and/or 370.

In the example shown in FIG. 9, the proximal port 473 can be configured to receive a proboscis 442 of a lock that is part of and/or included in a transfer device (e.g., as described above with reference to the access device 270 and the transfer device 210). In other embodiments, however, the proximal port 473 can be configured to receive a portion of an adapter (e.g., the adapter 395) and/or a portion of any suitable device. In still other embodiments, the proximal port 473 can be configured to receive a portion of a luer lock and/or any other suitable locking and/or coupling mechanism. The proximal port 473 includes a seal 474 that can be transitioned from a closed configuration and/or state to an open configuration and/or state (or a substantially open configuration and/or state). In the embodiment shown in FIG. 9, the seal 474 can be, for example, a single latch, flap, membrane, diaphragm, etc. that can be pushed and/or otherwise transitioned from a substantially closed state or configuration to a substantially open state or configuration when the proboscis 442 is inserted into the proximal port 473. As such, when a predetermined and/or desirable amount or portion of the proboscis 442 has been inserted into the proximal port 473, a distal end portion or surface of the proboscis 442 can extend beyond the seal 473 (e.g., latch, flap, etc.) and/or can otherwise be positioned such that a catheter of the transfer device can be advanced through the proboscis 442 and past the seal 474 (e.g., substantially without kinking, bending, and/or otherwise getting caught on the seal 474).

Conversely, prior to the proboscis 442 being inserted into the proximal port 473 and/or after the proboscis 442 has been removed from the proximal port 473, the seal 474 can be disposed in a substantially closed or substantially fluidically sealed state or configuration. For example, in some embodiments, the seal 474 can be biased and/or can include a bias member that can bias the seal 474 in the sealed or closed state and/or configuration. In other embodiments, a positive pressure within a lumen of the access device can place the seal 474 in the sealed and/or closed state or configuration. Although not shown in FIG. 9, in some embodiments, the seal 474 can be configured to engage and/or contact an inner surface of the proximal port 473 (e.g., a seal or valve seat or the like) when in the sealed and/or closed state or configuration. As such, when the seal 474 is in the sealed or closed state and/or configuration, the seal 474 can be configured to seal the proximal port 473 to limit and/or substantially prevent a flow of fluid therethrough (e.g., the seal 474 is in a substantially fluidically sealed state and/or configuration).

FIG. 10 illustrates a proximal port 573 of an access device included in a "closed system," according to another embodiment. The proximal port 573 and/or at least a portion thereof can be substantially similar in at least form and/or function to the proximal port 473 described above with reference to FIG. 9. As such, the proximal port 573 includes a seal 574 that can be transitioned from a closed configuration and/or state to an open configuration and/or state (or a substantially open configuration and/or state). In the example shown in FIG. 10, however, the seal 574 included and/or disposed in the proximal port 573 can be, for example, a set of latches, flaps, membranes, diaphragms, etc. that can be pushed and/or otherwise transitioned from a substantially closed state or configuration to a substantially open state or configuration when a proboscis 542 of a transfer device is inserted into the proximal port 573. For example, in some embodiments, the seal 574 can include and/or can be formed by two, three, four, five, six, or more latches, flaps, membranes, diaphragms, etc.

As shown, when a predetermined and/or desirable amount or portion of the proboscis 542 has been inserted into the proximal port 573, a distal end portion or surface of the proboscis 542 can extend beyond the seal 574 and/or can otherwise at least partially separate the latches, flaps, etc. of the seal 574 to form an opening therebetween such that a catheter of the transfer device can be advanced through the proboscis 542 and past the seal 574 (e.g., substantially without kinking, bending, and/or otherwise getting caught on the seal 574). As described above with reference to the seal 474, prior to the proboscis 542 being inserted into the proximal port 573 and/or after the proboscis 542 has been removed from the proximal port 573, the seal 574 can be disposed in a substantially closed or sealed state or configuration, in which the multiple latches, flaps, etc. form a substantially fluid tight seal therebetween.

Figure 11:
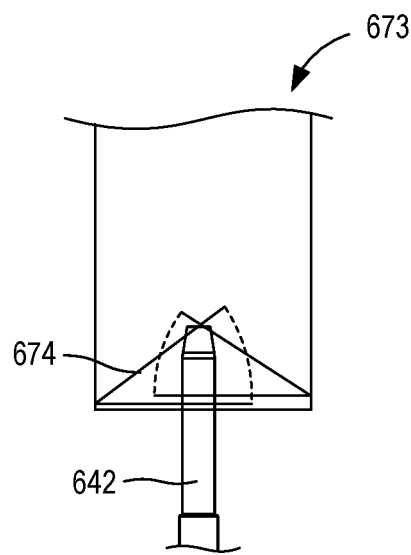

FIG. 11 illustrates a proximal port 673 of an access device included in a "closed system," according to another embodiment. The proximal port 673 and/or at least a portion thereof can be substantially similar in at least form and/or function to the proximal port 473 and/or the proximal port 573 described above with reference to FIG. 9 and FIG. 10, respectively. As such, the proximal port 673 includes a seal 674 that can be transitioned from a closed configuration and/or state to an open configuration and/or state (or a substantially open configuration and/or state). While the seal 574 is shown in FIG. 10 as including multiple seals (e.g., latches, flaps, etc.) that are separated, pushed, and/or otherwise transitioned from the substantially closed state or configuration to the substantially open state or configuration when a predetermined and/or desirable amount or portion of the proboscis 642 has been inserted into the proximal port 673 to form an opening therebetween, in the example shown in FIG. 11, the seal 674 includes multiple seals (e.g., latches, flaps, etc.) that remain in a semi-overlapping or semi-closed state.

In this embodiment, one or more of the seals (e.g., latches, flaps, etc.) can define a notch, cutout, contour, and/or the like that is exposed when the seal 674 is placed in the open configuration. Accordingly, while the latches, flaps, etc. of the seal 674 are still at least partially overlapping when the proboscis 642 transitions the seal 674 to the open state and/or configuration, a catheter of the transfer device can be advanced through the proboscis 642 and through the exposed notch, cutout, contour, and/or the like. As described above with reference to the seal 474, prior to the proboscis 642 being inserted into the proximal port 673 and/or after the proboscis 642 has been removed from the proximal port 673, the seal 674 can be disposed in a substantially closed or sealed state or configuration, in which the multiple latches, flaps, etc. form a substantially fluid tight seal therebetween (e.g., the notch, cutout, contour, and/or the like is substantially obstructed, occluded, blocked, covered, etc.).

Figure 12:
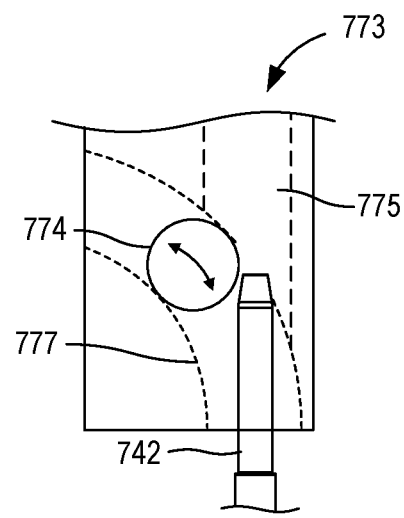

FIG. 12 illustrates a proximal port 773 of an access device included in a "closed system," according to another embodiment. The proximal port 773 and/or at least a portion thereof can be substantially similar in at least form and/or function to the proximal ports 473, 573, and/or 673 described above with reference to FIGS. 9, 10, and 11, respectively. As such, the proximal port 773 includes a seal 774 that can be transitioned from a closed configuration and/or state to an open configuration and/or state (or a substantially open configuration and/or state) in response to a portion of a proboscis 742 of a transfer device being inserted into the proximal port 773 (as described above).

While the seals 474, 574, and 674 are described above as being in the form of one or more latches, flaps, membranes, diaphragms, in other embodiments, the seal can be any suitable configuration. For example, in the embodiment shown in FIG. 12, the seal 774 is a ball seal or the like including a ball (e.g., seal 774) configured to move along a predetermined and/or defined path 777. As such, when a predetermined and/or desirable amount or portion of the proboscis 742 has been inserted into the proximal port 773, a distal end portion or surface of the proboscis 742 can contact the ball seal 774 and can move the ball seal 774 within and/or along the defined path 777 from a first position in which the ball seal 774 seals the proximal port 773 to a second position in which the ball seal 774 is in an open state or configuration. As shown in FIG. 12, for example, the ball seal 774 can be moved and/or transitioned to a position and/or configuration in which the proboscis 742 can gain access to a lumen 775 defined by the proximal port 773 (e.g., a lumen in fluid communication with a catheter or the like of the access device). As such, a catheter of the transfer device can be advanced through the proboscis 742, past the seal 774, and through the lumen 775. As described above with reference to the seals 474, 574, and/or 674, prior to the proboscis 742 being inserted into the proximal port 773 and/or after the proboscis 742 has been removed from the proximal port 773, the seal 774 can be disposed in a substantially closed or sealed state or configuration, in which the ball seal 774 occludes, obstructs, and/or blocks at least one of the lumen 775 and/or the proximal port 773.

Figure 13:
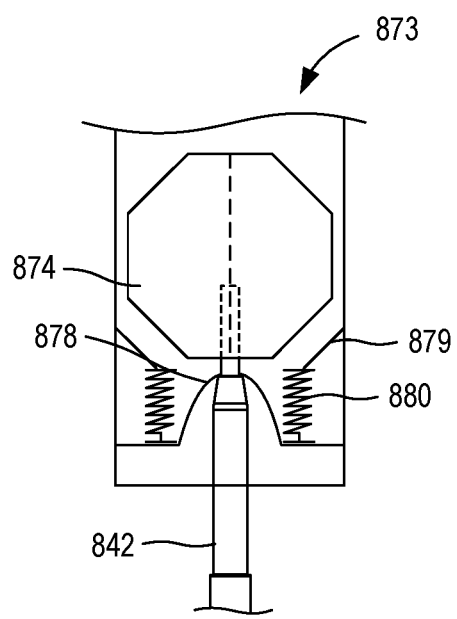

FIG. 13 illustrates a proximal port 873 of an access device included in a "closed system," according to another embodiment. The proximal port 873 and/or at least a portion thereof can be substantially similar in at least form and/or function to the proximal ports 473, 573, 673, and/or 773 described above with reference to FIGS. 9, 10, 11, and 12, respectively. As such, the proximal port 873 includes a seal 874 that can be transitioned from a closed configuration and/or state to an open configuration and/or state (or a substantially open configuration and/or state) in response to a portion of a proboscis 842 of a transfer device being inserted into the proximal port 873 (as described above).

In the embodiment shown in FIG. 13, the seal 874 can be a seal member, grommet, plug, occlusion member, split septum, plunger, etc. that forms and/or defines a pre-formed slit or the like that can be transitioned between a closed state and/or configuration and an open state and/or configuration. More specifically, the proximal port 873 includes a receiving portion or member 878 that receives the proboscis 842 as the proboscis 842 is inserted into the proximal port 873. In some instances, when the proboscis 842 is inserted into the proximal port 873, the proboscis 842 can contact the receiving portion or member 878, which in turn, is moved with the proboscis 842 as it is inserted into the proximal port 873. As shown, the receiving port or member 878 also includes an engagement member such as a rod, hypotube, and/or the like that can be inserted into the pre-formed slit to open the slit, thereby transitioning the seal 874 from a closed configuration to an open configuration in which a catheter of the transfer device can be advanced through the proboscis 842, through the hypotube or the like of the receiving portion and/or member 878, through the now-opened slit defined by the seal 874, and through the access device.

As described above with reference to the seals 474, 574, 674, and/or 774, prior to the proboscis 842 being inserted into the proximal port 873 and/or after the proboscis 842 has been removed from the proximal port 873, the seal 874 can be disposed in a substantially closed or sealed state or configuration, in which the hypotube or the like of the receiving portion and/or member 878 is withdrawn and/or otherwise outside of the pre-formed slit of the seal 874. For example, as shown in FIG. 13, the proximal port 873 can include one or more springs 880, bias members, energy storage members, and/or the like that can place the receiving portion and/or member 878 in a biased position (when not otherwise moved by the proboscis 842), in which the hypotube or the like is disengaged or withdrawn from the slit defined by the seal 874. Moreover, in some embodiments, the seal 874 can be placed in contact with a contact or seal surface 879 when in the closed or sealed state in response to a positive pressure within the access device, defining a substantially fluid tight seal therebetween. Accordingly, the proximal port 873 can be in the sealed or closed state and/or configuration when the proboscis 842 is not inserted therethrough.

Figure 14:
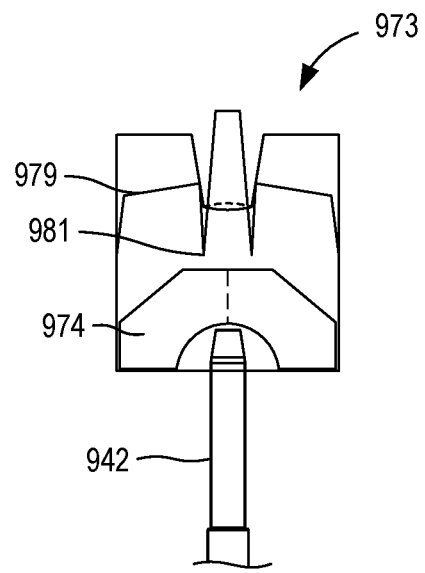

FIG. 14 illustrates a proximal port 973 of an access device included in a "closed system," according to another embodiment. The proximal port 973 and/or at least a portion thereof can be substantially similar in at least form and/or function to the proximal ports 473, 573, 673, 773, and/or 873 described above with reference to FIGS. 9, 10, 11, 12, and 13, respectively. As such, the proximal port 973 includes a seal 974 that can be transitioned from a closed configuration and/or state to an open configuration and/or state (or a substantially open configuration and/or state) in response to a portion of a proboscis 942 of a transfer device being inserted into the proximal port 973 (as described above).

In the embodiment shown in FIG. 14, the seal 974 can be a seal member, grommet, plug, occlusion member, split septum, plunger, etc. that forms and/or defines a pre-formed slit or the like that can be transitioned between a closed state and/or configuration and an open state and/or configuration, as described above with reference to the seal 874. In some embodiments, the arrangement of the proximal port 973 can be such that when the proboscis 942 is inserted into the proximal port 973, the proboscis 942 can contact the seal 974 and can displace and/or deform the seal 974, in response to the contact. As shown, the proximal port 973 can include a contact or seal surface 979, which the seal 974 is placed in contact with in response to being engaged by the proboscis 942. Moreover, the contact or seal surface 979 can form a hollow or annular ridge 981, tube, pillar, protrusion, column, etc. about which the seal 974 deforms when placed in contact with the contact or seal surface 979. For example, in some embodiments, the seal 974 can be displaced and can be deformed when placed in contact with the contact and/or seal surface 979 such that the hollow or annular ridge 981 or the like is inserted through the slit formed by the seal 974. In other words, the proboscis 942 can displace the seal 974 such that the seal 974 deforms about or around the annular ridge 981 or the like. Thus, when the seal 974 is deformed about or around the annular ridge 981 or the like, a catheter of the transfer device can be advanced through the proboscis 942, through an opening defined by the annular ridge 981 or the like, and through the access device.

As described above with reference to the seals 474, 574, 674, 774, and/or 874, prior to the proboscis 942 being inserted into the proximal port 973 and/or after the proboscis 942 has been removed from the proximal port 973, the seal 974 can be disposed in a substantially closed or sealed state or configuration, in which the slit defined by the seal 974 is in a substantially closed state. That is to say, the seal 974 can be in an undeformed and/or otherwise sealed state when the proboscis 942 is not inserted into the proximal port.

While the proximal ports 473, 573, 673, 773, 873, and/or 973 are specifically described above with reference to FIGS. 9-14, it should be understood that these embodiments have been presented by way of example only and not limitation. For example, while the proximal ports 473, 573, 673, 773, 873, and/or 973 are described above as receiving a portion of the proboscis 442, 542, 642, 742, 842, and/or 942, respectively, in other embodiments, a proximal port (e.g., similar to or substantially the same as any of those described above) can be coupled to and/or can receive any suitable device, adapter, component, etc., which may or may not have a proboscis similar to those described above with reference to FIGS. 9-14. For example, in some embodiments, a proximal port can be configured to receive a portion of an adapter, as described above with reference to FIG. 8. In other embodiments, a proximal port can receive any suitable portion of a device that can be at least partially inserted into the proximal port to transition the seal disposed therein from a substantially sealed or closed state to an open state to allow a catheter to be advanced therethrough. Accordingly, while FIGS. 9-14 show the proboscis 442, 542, 642, 742, 842, and 942, respectively, it should be understood that these have been presented by way of example only and not limitation.

Although the seals 474, 574, 674, 774, 874, and/or 974 are particularly described above, it should be understood that a proximal port can include a seal having any suitable configuration and/or a seal formed of any combination of components. For example, in some embodiments, the proximal port 474 shown in FIG. 9 can include the seal 474 (as described above), which can be and/or can form a first portion of a multi-portion, multi-part, or multi-phase seal. Such a seal can include the first portion and one or more additional portions (e.g., formed by and/or formed of one or more components, seal, valves, etc.). For example, in some embodiments, a seal can include a first portion configured as the seal 474 shown in FIG. 9 and can include a second portion configured as, for example, a silicone or rubber split septum seal or valve (e.g., similar to and/or substantially the same as the seal 974). In some embodiments, the second portion (e.g., the split septum) can be an outer portion or member and the first portion can be an inner portion or member. In such embodiments, a user can advance a proboscis and/or any other suitable portion of a device through the first portion and the second portion of the seal to transition the seal from a substantially sealed or closed state or configuration to a substantially open state or configuration. In some embodiments, the use of a multi-portion, multi-part, and/or multi-phase seal can result in, for example, a higher pressure rating associated with the seal. That is to say, in some instances, a multi-portion seal can be configured to maintain a substantially fluid tight seal when exposed to a pressure that may otherwise be sufficient to transition a single-portion or single part seal (e.g., the seal 474) from the substantially sealed or closed state to the open state.

Figure 15:
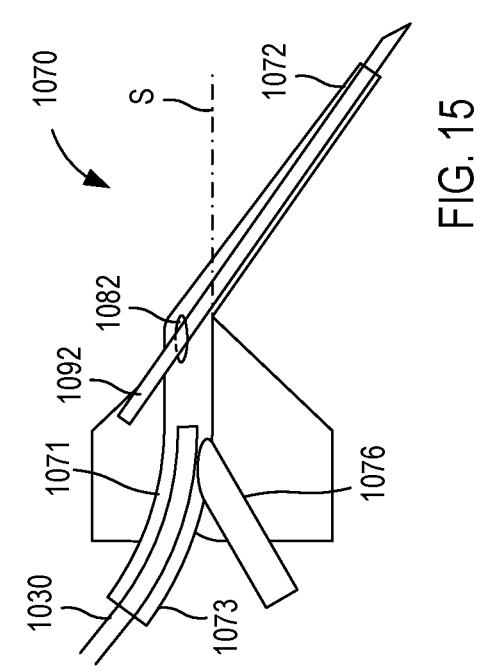

While the proximal port 273 of the access device 270 is shown, for example, in FIGS. 3 and 4 as being substantially coaxial with the catheter 272, in other embodiments, an access device such as those described herein can be formed such that a proximal port is disposed at an angle relative to a catheter of the access device and/or otherwise is non-coaxial with the catheter. For example, FIG. 15 illustrates an access device 1070 according to an embodiment. The access device 1070 can be any suitable shape, size, and/or configuration. In some embodiments, the access device 1070 and/or at least a portion thereof can be substantially similar in at least form and/or function to any of the access devices described herein.

As shown, the access device 1070 includes a hub 1071 and a catheter 1072. For example, in some embodiments, the hub 1071 of the access device 1070 can have a proximal portion 1073 and a side port 1076. The side port 1076 can be substantially similar to, for example, the side port 276 described above and thus, not described in further detail herein. In some embodiments, the hub 1071 can have a substantially curved shape such that the proximal port 1073 is disposed at a predetermined and/or desired angle relative to an insertion site of the patient. In some embodiments, the predetermined and/or desired angle can be between about 0° and about 30° and/or any fraction of a degree thereof. For example, in some embodiments, the predetermined and/or desired angle can be about 1°, about 2°, about 3°, about 4°, about 5°, about 6°, about 7°, about 8°, about 9°, about 10°, about 11°, about 12°, about 13°, about 14°, or about 15°. In other embodiments, the predetermined and/or desired angle can be between about 15° and about 25°. In still other embodiment, the predetermined and/or desired angle can be greater than 30°. In some embodiments, the hub 1071 can form a relatively smooth and/or gradual curve (e.g., can have a relatively large radius of curvature) to dispose the proximal port 1073 at the desired angle.

As described above, the catheter 1072 of the access device 1070 is configured to be inserted through the skin of a patient (e.g., at a desired insertion site, indicated by the line S in FIG. 15) and at least partially disposed within a target conduit within the body (e.g., a vein). In some embodiments, the access device 1070 can be at least temporarily coupled to an insertion device (not shown) having an insertion member 1092 configured to pierce the skin of the patient at the insertion site S and then configured to be removed from the access device 1070, as described above with reference to the closed system access devices 100 and/or 200. As described above, the insertion member 1092 can be a relatively rigid member configured to pierce or puncture the skin of the patient (e.g., a needle, trocar, and/or the like). In the embodiment shown in FIG. 15, the access device 1070 can define an opening 1082 or port that can be configured to receive the insertion member 1092. The arrangement and/or placement of the opening 1082 or port can be such that the insertion member 1092 extends through a relatively straight path through a portion of the access device 1070. Thus, the insertion member 1092 can be used during the placement of the catheter 1072 in a vein of a patient and then can be removed from the access device 1070, as described in detail above. In some embodiments, the opening 1082 and/or port can be configured to seal or close when the in response to the removal of the insertion member 1092.

In some instances, it may be desirable to withdraw a volume of bodily fluid from the patient via the access device 1070. In some such instances, after the catheter 1072 is placed in a desired position within a vein of the patient, a user may couple a fluid transfer device to the proximal port 1073 of the access device 1070, as described in detail above with reference to, for example, the access device 270 and the fluid transfer device 210. The coupling of the fluid transfer device to the proximal port 1073 can, for example, transition a seal, valve, etc. disposed in the proximal port 1073 from a closed or sealed state and/or configuration to an open state and/or configuration (as described in detail above). Thus, after coupling the fluid transfer device to the proximal port 1073, the user can manipulate the fluid transfer device to advance a catheter 1030 through the proximal port 1073 of the access device 1070, as shown in FIG. 15. In some embodiments, the catheter 1030 can be sufficiently flexible to bend, flex, and/or otherwise non-permanently reconfigure as the catheter 1030 is advanced through the relatively curved and/or tortuous lumen defined by the access device 1070. Accordingly, the access device 1070 can function in a substantially similar manner to any of those described above.

Figure 16:
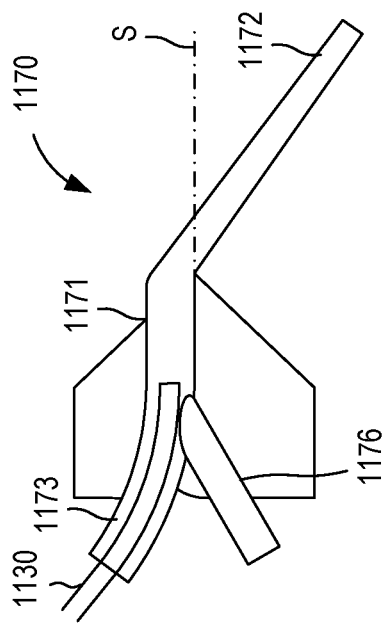
FIGS. 15-17 are each a schematic illustration of a closed system access device according to various embodiments.

FIG. 16 illustrates an access device 1170 according to another embodiment. The access device 1170 can be any suitable shape, size, and/or configuration. In some embodiments, the access device 1170 and/or at least a portion thereof can be substantially similar in at least form and/or function to any of the access devices described herein. As shown, the access device 1170 includes a hub 1171 and a catheter 1172. The hub 1171 of the access device 1170 can have a proximal portion 1173 and a side port 1176. The side port 1176 can be substantially similar to, for example, the side port 276 described above and thus, not described in further detail herein. In some embodiments, the hub 1171 can have a substantially curved shape such that a proximal port 1173 is disposed at a predetermined and/or desired angle relative to an insertion site of the patient, as described above with reference to the access device 1070. As described above, the catheter 1172 of the access device 1170 is configured to be inserted through the skin of a patient (e.g., at a desired insertion site, indicated by the line S in FIG. 16) and at least partially disposed within a target conduit within the body (e.g., a vein).

In some embodiments, the access device 1170 can be at least temporarily coupled to an insertion device (not shown) having an insertion member (not shown) configured to pierce the skin of the patient at the insertion site S and then configured to be removed from the access device 1170, as described above with reference to the closed system access devices 100 and/or 200. As described above, the insertion member can be configured to pierce or puncture the skin of the patient (e.g., a needle, trocar, and/or the like). While the access device 1170 is described above and shown in FIG. 15 as defining the opening 1082 or port configured to receive the insertion member, in other embodiments, an access device need not define an opening or port configured to receive a portion of an insertion device (e.g., an insertion member).

For example, in some embodiments, an insertion member (e.g., needle) can have a sufficient flexibility to pass through a relatively curved or tortuous lumen defined by the access device 1170. In other embodiments, the access device 1170 can be sufficiently compact to allow a relatively rigid insertion member (e.g., needle) to pass therethrough (e.g., the access device 1170 can define a relatively straight lumen through the device through which the insertion member can pass). In still other embodiments, the access device 1170 can be formed from a relatively soft and/or flexible material that can deform and/or otherwise reconfigure in response to the presence of the insertion member. For example, the access device 1170 can have and/or can form a relatively curved shape and can define a relatively curved and/or tortuous lumen therethrough. During one or more manufacturing process, an insertion device (e.g., such as those described herein) can be coupled to access device 1170 and a relatively rigid insertion member (e.g., a needle or trocar) can be inserted through the lumen of the access device 1170. In some instances, as the insertion member is inserted through the lumen, the access device 1170 and/or at least a portion thereof can bend, flex, deflect, deform, and/or otherwise reconfigure to a state and/or arrangement in which the lumen of the access device 1170 is substantially straight, thereby allowing the relatively rigid insertion member to be advanced therethrough.

In use, after the insertion member has pierced the insertion site S and placed the catheter 1172 of the access device 1170 in desired position within the patient (e.g., a desired position within a vein of the patient), the insertion device can be removed from the access device 1170, as described in detail above. In some instances, the removal of the insertion device can allow the access device 1170 to bend, flex, deflect, deform, and/or otherwise reconfigure in a substantially opposite manner as that described with reference to inserting the insertion member during manufacturing. Thus, when the catheter 1172 is in a desired position within the vein of the patient and the insertion device is removed from the access device 1170, the proximal port 1173 can be disposed at the predetermined and/or desired angle relative to the insertion site S.

In some instances, it may be desirable to withdraw a volume of bodily fluid from the patient via the access device 1170. In some such instances, after the catheter 1172 is placed in a desired position within a vein of the patient, a user may couple a fluid transfer device to the proximal port 1173 of the access device 1170, as described in detail above with reference to, for example, the access device 270 and the fluid transfer device 210. The coupling of the fluid transfer device to the proximal port 1173 can, for example, transition a seal, valve, etc. disposed in the proximal port 1173 from a closed or sealed state and/or configuration to an open state and/or configuration (as described in detail above). Thus, after coupling the fluid transfer device to the proximal port 1173, the user can manipulate the fluid transfer device to advance a catheter 1130 through the proximal port 1173 of the access device 1170, as shown in FIG. 16. In some embodiments, the catheter 1130 can be sufficiently flexible to bend, flex, and/or otherwise non-permanently reconfigure as the catheter 1130 is advanced through the relatively curved and/or tortuous lumen defined by the access device 1170. Accordingly, the access device 1170 can function in a substantially similar manner to any of those described above.

In some embodiments, forming the access device 1170 from a relatively flexible material (such as any of the biocompatible materials described above and/or blends or copolymers thereof) can facilitate and/or simplify one or more manufacturing processes. For example, in some embodiments, forming the access device 1170 from a relatively flexible material can allow the access device 1170 to be manufactured as a monolithic or unitarily formed piece (e.g., formed from or formed by a single work-piece and/or a substantially contiguous material).

In some embodiments, forming the access device 1170 from a relatively flexible material can allow for the use of a single core pin during manufacturing, which is used to form and/or define a lumen during, for example, molding of the access device. In such embodiments, the material can be biased such that the material forms the relatively curved configuration after molding and upon removal of the core pin. In other embodiments, the access device 1170 can be molded and/or otherwise formed, the core pin can be removed, and the relatively flexible material can be worked and/or reconfigured to form the desired shape and/or configuration of the access device 1170 without obstructing or occluding the lumen formed therethrough.

Figure 17:
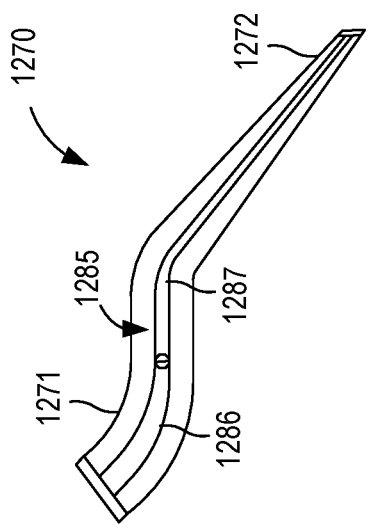

While described as being formed using a single core pin (e.g., during one or more molding processes or the like), in other embodiments, an access device can be formed and/or manufactured using a multi-piece core pin. For example, FIG. 17 illustrates an access device 1270 being formed by a multi-piece core pin 1285 according to an embodiment. As shown, the access device 1270 includes at least a hub 1271 and a catheter 1272 and can be configured to be substantially similar in at least form and/or function to any of the access devices described herein (e.g., can be included in and/or can form a part of a closed system access device). As described above with reference to the access device 1170, the core pin 1285 can be used to form and/or define a lumen of the access device 1270 during, for example, one or more molding processes. In the embodiment shown in FIG. 17, the core pin 1285 includes a first member 1286 and a second member 1287 that couple, mate, abut, and/or otherwise are collectively positioned to form the core pin 1285. In some instances, the use of a multi-piece core pin can facilitate removal of the core pin 1285 from the access device 1270. For example, in some embodiments, the first member 1286 can be accessed at or near the hub 1271 of the access device 1270 and removed therethrough, while the second member 1287 can be accessed at or near the catheter 1272 of the access device 1270 and removed therethrough. In some embodiments, such an arrangement can allow for reduced and/or simplified working and/or reconfiguring of the access device 1270 after removal of the core pin 1285 compared to, for example, an amount of working and/or reconfiguring associated with the use of a single or one-piece core pin.

Figure 18:
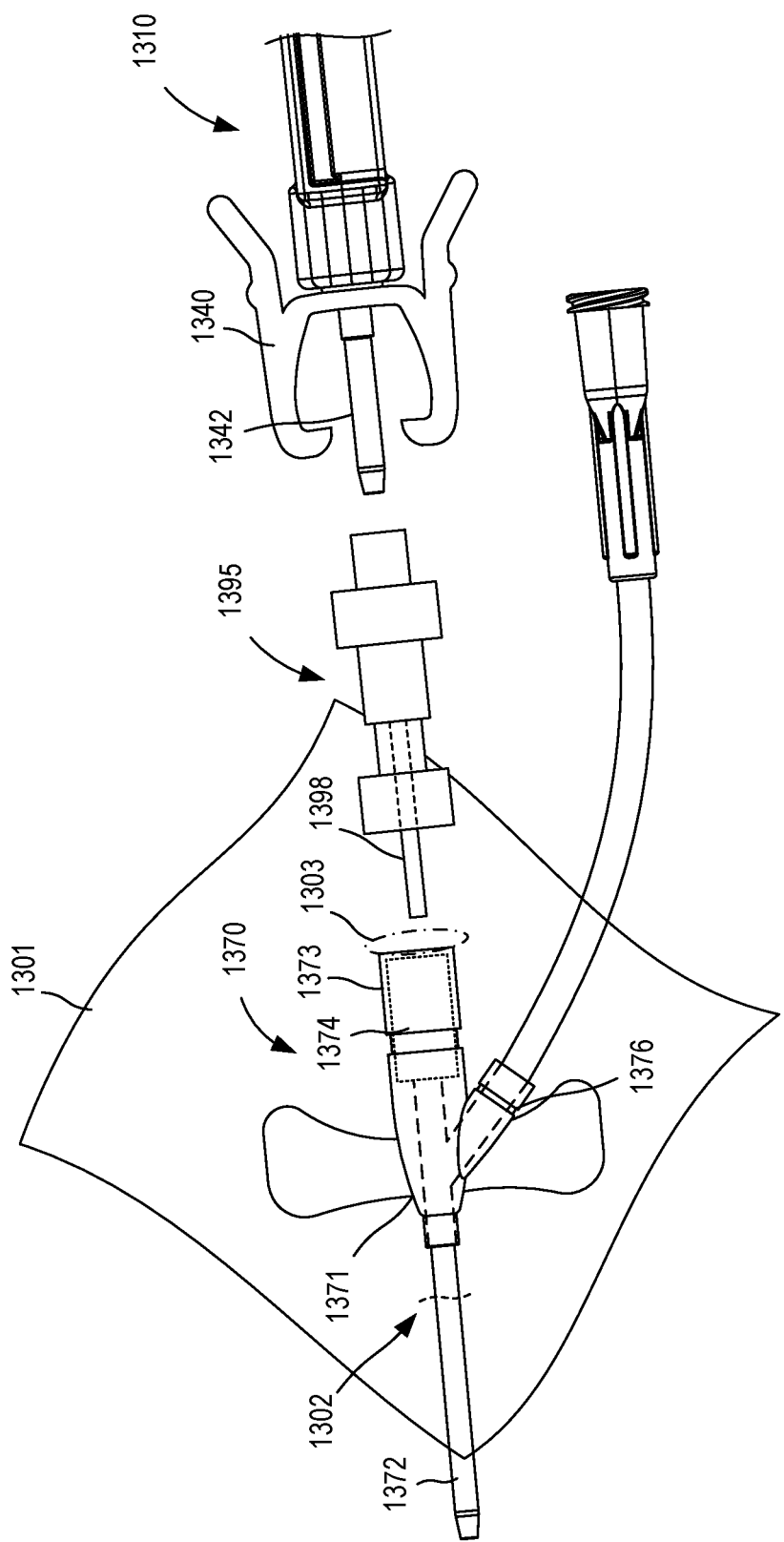
FIG. 18 is a schematic illustration of a dressing coupled to and/or otherwise in use with a closed system access device according to an embodiment.

Although not shown in FIGS. 1-17, any of the embodiments described herein can be used with any suitable dressing configured to secure an access device to the skin of a patient and to reduce and/or limit contamination of the insertion site. For example, FIG. 18 illustrates a dressing 1301 coupled to and/or otherwise in use with a closed system access device 1370 according to an embodiment. The access device 1370 can be any suitable shape, size, and/or configuration. For example, the access device 1370 shown in FIG. 18 includes a hub 1371 having a proximal port 1373 disposed at and/or coupled to a proximal end portion of the hub 1371, and a catheter 1372 disposed at and/or coupled to a distal end portion of the hub 1371. The proximal port 1373 can be coupled to and/or can engage any suitable device, as described in detail above. The catheter 1372 can be inserted through an insertion site 1302 of the patient to place the catheter 1372 within a vessel or vein. In some embodiments, the access device 1370 can be substantially similar to any of the access devices 170, 270, and/or 370 described in detail above. Accordingly, the access device 1370 is not described in further detail herein.

The dressing 1301 can be any suitable dressing configured to secure the access device 1370 to the skin of a patient and to reduce and/or limit contamination of the insertion site 1302. In some embodiments, the dressing 1301 can be any industry standard transparent dressing such as, for example, Tegaderm or the like. As such, the dressing 1301 can be a relatively thin sheet of film that can be, for example, flexible, resilient, deformable, and/or waterproof or otherwise semipermeable. Moreover, the film forming at least a portion of the dressing 1301 can have a surface that is maintained in a substantially sterile environment and/or packaging prior to use and that is configured to be placed in contact with the skin of the patient to cover and/or dress the insertion site 1302. At least a portion of the surface can include and/or can be coupled to an adhesive configured to adhere the dressing 1301 to the skin of the patient to cover the insertion site 1302.

As shown in FIG. 18, in some instances, the dressing 1301 can be applied to and/or can cover at least a portion of the access device 1370 when the dressing 1301 is coupled or adhered to the skin of the patient. In some embodiments, the dressing 1301 can be applied to and/or can cover the hub 1371 of the access device 1370 including, for example, the proximal port 1373 while allowing a flexible tubing coupled to a side port 1376 of the hub 1371 to extend beyond and/or outside of the dressing 1301 (see FIG. 18). As such, the dressing 1301 can cover the hub 1371 of the access device 1370 and the insertion site 1302 of the patient to maintain the hub 1371 and/or insertion site 1302 in a substantially sterile environment and/or to otherwise reduce and/or limit a potential contamination of the insertion site 1302, which can lead to infection of the patient.

As described above, the dressing 1301 can be applied to the hub 1371 of the access device 1370 such that the proximal port 1373 is covered by the dressing 1301. In some known instances, such an arrangement can block access to the proximal port 1373 by a device disposed outside of the dressing 1301. In some embodiments, however, at least a portion of the dressing 1301 can be formed of a pierceable, deformable, and/or reconfigurable material (referred to for simplicity as "pierceable material") that can selectively allow access to the proximal port 1373 of the access device 1370. In some embodiments, substantially the entire dressing 1301 can be formed of the pierceable material. In other embodiments, a region of the dressing 1301 can be formed of the pierceable material. For example, as shown in FIG. 18, the dressing 1301 can include at least a region 1303 formed of the pierceable material that is aligned with and/or otherwise covering at least a portion of the proximal port 1373. While the region 1303 is described as being formed of a pierceable material, in some embodiments, the region 1303 can include, for example, a pre-slit septum and/or the like.

In some embodiments, the arrangement of the region 1303 of the dressing 1301 relative to the proximal port 1373 can allow a device to access the proximal port 1373 of the access device 1370 without removing the dressing 1301 from the skin of the patient. For example, as shown in FIG. 18, an adapter 1395 can be manipulated to pierce the pierceable material of the region 1303 and/or to advance through a pre-slit septum included in and/or formed by the region 1303. In some embodiments, the adapter 1395 can be substantially similar to the adapter 395 and can include, for example, an engagement member 1398 that can be inserted into the proximal port 1373 in response to the adapter 1395 being coupled to the proximal port 1373.

In this embodiment, coupling the adapter 1395 to the proximal port 1373 of the access device 1370 can be such that the engagement member 1398 pierces and/or otherwise extends through the region 1303 of the dressing 1301 and into the proximal port 1373. As the engagement member 1398 is inserted into the proximal port 1373, at least a portion of the engagement member 1398 can extend through and/or can otherwise engage a seal 1374 disposed in the proximal port 1373 (e.g., a seal, valve, needle-free connection, and/or any other sealing member such as those described above), which in turn, can transition the seal 1374 from a substantially sealed or closed state to an open state to place the adapter 1395 in fluid communication with the hub 1371, as detail above with reference to the adapter 395 and the access device 370. Accordingly, the configuration of the dressing 1301 in FIG. 18 can allow the adapter 1395 to couple to the proximal port 1373 of the access device 1370 in substantially the same manner as described above with reference to the adapter 395 and access device 370 shown in FIG. 8. Moreover, in some embodiments, at least a portion of the dressing 1301 can be disposed between an inner surface of the adapter 1395 and an outer surface of the proximal port 1373 when the adapter 1395 is coupled to the proximal port 1373. In some instances, this portion of the dressing 1301 can form and/or can otherwise act as a gasket or seal between proximal port 1373 and the adapter 1395, thereby allowing the dressing 1301 to maintain a sealed environment around the insertion site 1302 and at least a portion of the access device 1370.

As described above with reference to FIG. 8, in some embodiments, prior to or after coupling the adapter 1395 to the access device 1370, a transfer device 1310 can be coupled to the proximal end portion of the adapter 1395. The transfer device 1310 can be any suitable shape, size, and/or configuration. In some embodiments, for example, the transfer device 1310 can be similar to and/or substantially the same as the transfer devices 210 and/or 310. In some embodiments, the transfer device 1310 can be similar to and/or substantially the same as any of the transfer devices described in the '272 patent, the '247 patent, and/or the '344 patent. Accordingly, the transfer device 1310 can include a lock 1340 (e.g., a lock similar to the lock 240 described above, a slip luer lock, a locking luer lock, and/or any other suitable lock or coupler) configured to couple to the proximal end portion of the adapter 1395.

In some embodiments, the proximal end portion of the adapter 1395 can include, for example, a needle-free connector or valve, a split septum, and/or any suitable seal member that can be transitioned from a sealed or closed state to an open state in response to being contacted by and/or engaged with a portion of the lock 1340 (as described above with reference to the devices 200 and/or 300). Thus, when the adapter 1395 is coupled to the proximal port 1373 of the access device 1370 and the transfer device 1310 is coupled to the proximal end portion of the adapter 1395, a lumen, channel, conduit, passageway, etc. can be defined that can allow a catheter of the transfer device 1310 (not shown in FIG. 18) to be advanced through at least a portion of the access device 1370.

While the adapter 1395 is shown in FIG. 18 and particularly described above, in other embodiments, the adapter 1395 can be any suitable shape, size, and/or configuration. In some embodiments, for example, the adapter 1395 can be a needle-free connector, a male or female luer lock, and/or an adapter similar to or the same as some commercially available needle-free connectors. In other embodiments, the adapter 1395 can be a blunt cannula with or without a coupler, lock, or luer disposed at the proximal end portion and/or the distal end portion.

While the adapter 1395 is described above as being coupled to and/or at least partially inserted through a portion of the dressing 1301 (e.g., the region 1303), in other embodiments, the adapter 1395 can be at least partially formed with the dressing 1301 during one or more manufacturing processes. For example, in some embodiments, the adapter 1395 can be a luer lock, split septum connector, needle-free connector and/or the like that can be integrally formed with the dressing 1301. By way of example, the dressing 1301 can define an opening configured to receive a portion of the adapter 1395 during manufacturing. In some embodiments, the adapter 1395 can include a flange or other suitable surface that can be placed in contact with a surface of the dressing 1301 that surrounds and/or at least partially defines the opening. The surface of the dressing 1301 can be coupled to the flange or other suitable surface of the adapter 1395 during one or more manufacturing processes via, for example, an adhesive, ultrasonic welding, and/or any other suitable coupling method. As such, the integrated dressing 1301 and adapter 1395 can be sterilized, packaged, sold, and/or used as an integrated device having a dressing portion and an adapter portion.

In such embodiments, after the catheter 1372 of the access device 1370 has been placed in the vessel or vein, the adapter portion of the integrated device can be coupled, for example, to the proximal port 1373 of the access device 1370. In addition, the dressing portion of the integrated device can be applied over the insertion site 1302 and at least a portion of the access device 1370, as described above with reference to the dressing 1301. Once in a desired position relative to the insertion site 1302 and the access device 1370, the dressing portion of the integrated device can be coupled to and/or adhered to the skin of the patient such that the insertion site 1302 and at least a portion of the access device 1370 (e.g., a portion including at least the hub 1371 and a portion of the catheter 1372 disposed outside of the body of the patient) are covered by the dressing portion of the integrated device. In some embodiments, such an arrangement can reduce an amount of bending, flexing, stretching, and/or deforming of a dressing or dressing portion which may otherwise result from non-integrated configurations. Moreover, in such an arrangement, a transfer device (e.g., the transfer device 1310) can be coupled to the adapter portion of the integrated device without having to pierce and/or otherwise extend through the dressing portion of the integrated device can obviate a need to pierce a portion of the dressing In some embodiments, the access device 1370 can be at least partially formed with the dressing 1301 during one or more manufacturing processes, in a manner similar to that of the adapter 1395. For example, in some embodiments, a portion of the dressing 1301 can be bonded, fixed, adhered, welded, and/or otherwise coupled to a portion of the hub 1371 during manufacturing. In such embodiments, the dressing 1301 and the access device 1370 can collectively form an integrated device. Moreover, the arrangement of the integrated device can be such that the dressing 1301 covers the insertion site 1302, a portion of the catheter 1372 disposed outside of the body, and a portion of the hub 1371, as shown in FIG. 18. The integrated device formed by the dressing 1301 and the access device 1370 can differ from the configuration shown in FIG. 18, however, in that the dressing 1301 can be coupled and/or fixed to the hub 1371 of the access device 1370 such that the proximal port 1373 is disposed outside of or at least partially outside of the dressing 1301 (e.g., on top of or otherwise not covered by). In other embodiments, the dressing 1301 can be coupled and/or fixed to the hub 1371 such that the proximal port 1373 and the side port 1376 are each disposed outside of the dressing 1301. As such, the dressing 1301 can secure the access device 1370 to the skin of the patient and can protect the insertion site 1302 while allowing the adapter 1395 and/or the transfer device 1310 to couple to and/or access the proximal port 1373 without having to pierce or otherwise extend through a portion of the dressing 1301.

While the adapter 1395 is described above as piercing and/or otherwise being inserted through a portion of the dressing 1301 (e.g., the region 1303 formed of the pierceable material and/or defining a pre-slit septum or the like), in other embodiments, the transfer device 1310 can be coupled to the proximal port 1373 of the access device 1370 without the adapter 1395. For example, in some embodiments, the transfer device 1310 can be coupled to the proximal port 1373 of the access device 1370 in a manner substantially similar to the coupling of the transfer device 210 to the access device 270 described above with reference to FIGS. 6 and 7. In the embodiment shown in FIG. 18, however, a proboscis 1342 of the lock 1340 can be inserted through a portion of the dressing 1301 (e.g., the region 1303) prior to being inserted into the proximal port 1373.

While some of the closed system access devices are described herein as configured to be coupled to a fluid transfer device via a proximal port (e.g., the proximal port 273 of the access device 270), in other embodiments, a closed system access device can be coupled to a fluid transfer device via a side port of the access device. For example, FIGS. 19 and 20 illustrate a closed system access device 1470 and a fluid transfer device 1410 that is configured to be coupled to the closed system access device 1470 via a side port 1476 thereof. As described above with reference to other access devices disclosed herein (e.g., access devices 170, 270, 370, etc.) the closed system access device 1470 (also referred to herein as "access device") can be any suitable device configured to be at least partially inserted or disposed within a portion of the body. For example, the access device 1470 can be a known peripheral intravenous line (PIV) or the like configured to be percutaneously inserted into a portion of the body. In some instances, the access device 1470 (e.g., PIV) can be at least partially disposed within a vein of a patient via a venipuncture event or the like, as described in further detail herein.

The access device 1470 or at least a portion thereof can be substantially similar in structure and/or function to the access devices 170, 270, 370, 1070, 1170, 1270, and/or 1370 described herein. The access device 1470 includes a hub 1471 and a catheter 1472. The hub 1471 of the access device 1470 defines a lumen 1475 and includes a proximal port 1473 and a side port 1476. Portions of the access device 1470 similar to corresponding portions of any of the access devices described herein with reference to other embodiments are not described in further detail herein.

The side port 1476 can be substantially similar to, for example, the side port 276, 1076, 1176, described above. The side port 1476 is in fluid communication with the lumen 1475 of the hub 1471. In some embodiments, the access device 1470 can be configured to receive a catheter advanced by a fluid transfer device coupled via the side port 1476 of the access device 1470. In some embodiments the side port 1476 can be coupled to tubing 1451 and can be in fluid communication with a lumen 1453 defined by the tubing 1451. The tubing 1451 can be of any predetermined length to be compatible with the catheter 1430 of suitable length. In some embodiments, the tubing 1451 can be configured to include a proximal coupler 1454 that can be configured as a threaded coupler, a slidable collar, one or more engagement members, a male or female luer lock (e.g., a slip luer or a locking luer), and/or any other suitable coupler, as shown in FIGS. 19 and 20. In some embodiments the tubing 1451 or the proximal coupler 1454 of the tubing 1451 can include a seal member (not shown in FIGS. 19 and 20). The seal member can be a plug, occlusion member, split septum, plunger, needle-free connector, etc. that can be transitioned between a closed state and/or configuration and an open state and/or configuration, as described above with reference to the seal 874. In some embodiments, the seal member (e.g., a needle-free valve or connector) can be integrated into the proximal coupler 1454. In other embodiments, the seal member can be a separate, independent, and/or otherwise non-integrated adapter or the like. In still other embodiments, the proximal coupler 1454 of the tubing need not include a seal or any other suitable fluid control device.

FIG. 19 illustrates the access device 1470 with the proximal coupler 1454 of the tubing 1451 engaged with a fluid transfer device 1410 (e.g., a proboscis 1442 of the fluid transfer device 1410). The fluid transfer device 1410 can be any suitable device configured to transfer fluid to or from the patient via the placed or indwelling access device 1470. In some instances, the fluid transfer device 1410 can be configured to couple to the access device 1470 once the access device 1470 is placed in the patient and the insertion device (not shown) is removed, as described above with reference to the access device 270. For example, the fluid transfer device 1410 can be substantially similar to any of the fluid transfer devices described herein with reference to specific embodiments, such as the fluid transfer devices 110, 210, and/or 310. As such, some aspects of the transfer device 1410 are not described in detail herein and should be considered substantially similar to such aspects of the transfer devices 110, 210, and/or 310 described herein, unless explicitly expressed otherwise.

The fluid transfer device 1410 can include at least an introducer 1415, an actuator 1420, a lock 1440, a proboscis 1442, and a catheter 1430. The introducer 1415 can be any suitable shape, size, and/or configuration. In some embodiments, the introducer 1415 can include a proximal end portion configured to be operably coupled to the hub 1471 of the access device 1470 (e.g., via a proximal port 1473 or the side port 1476 of the access device 1470). For example, in some embodiments, the proximal end portion of the introducer 1415 can include a lock, coupler, engagement member, and/or the like (e.g., the lock 1440) that can engage the proximal coupler 1454 to couple the introducer 1415 to the hub 1471 of the access device 1470 via the side port 1476 and the tubing 1451. More particularly, in some embodiments, the distal end portion of the introducer 1415 can include the lock 1440, which can be configured as, for example, a male or female luer lock (e.g., a slip luer or a locking luer). In other embodiments, the distal end portion of the introducer 1415 can include a lock similar to any of those described herein such as, for example, the lock 240 of the transfer device 210.

As shown in FIGS. 19 and 20, the proboscis 1442 of the lock 1440 extends from the lock 1440 in a distal direction (e.g., away from the introducer 1415). The proboscis 1442 can be configured such that the proboscis 1442 is inserted into the proximal coupler 1454 and/or a portion of the tubing 1451 that is in fluid communication with the side port 1476 of the access device 1470. Moreover, when the lock 1440 couples to the proximal coupler 1454, a lumen of the proboscis 1442 can be placed in fluid communication with the lumen 1453 of the tubing 1451. In some embodiments, the proboscis 1442 can be substantially similar in structure and/or function to the proboscis 242 described herein, and not described in further detail herein.

The catheter 1430 can be any suitable shape, size, and/or configuration. The catheter 1430 is at least temporarily disposed within an inner volume defined by the introducer 1415 and is coupled to the actuator 1420. The catheter 1430 can be selected to have a predetermined length suitable to traverse portions of the fluid transfer device 1410 (e.g., at least the introducer 1410, the proboscis 1442, etc.) and portions of the access device 1470 (e.g., the proximal coupler 1454, the tubing 1451, the side port 1476, the lumen 1475 of the access device 1470, a catheter 1472 of the access device 1470, etc.). In some embodiments, the catheter 1430 can have a length that is sufficient to advance the catheter 1430 through the transfer device 1410 and the access device 1470 to be positioned at a desired location in a vein of a patient (e.g., distal to a distal tip of the catheter 1472 of the access device 1470).

The introducer 1415 can define an inner volume within which at least a portion of the catheter 1430 and at least a portion of the actuator 1420 are movably disposed. As described in further detail herein, prior to use, the catheter 1430 can be in a first position, configuration, and/or state in which the catheter 1430 is disposed or substantially disposed within the inner volume of the introducer 1415. Such an arrangement can, for example, protect the catheter 1430 from being physically damaged prior to use and/or protect the catheter 1430 from being contaminated by a nonsterile environment. FIG. 19 shows the catheter 1430 in the first position, configuration, and/or state.

A first portion of the actuator 1420 (e.g., the portion disposed in the introducer 1415) is coupled to a proximal end portion of the catheter 1430. The first portion of the actuator 1420 can also be coupled to an outlet or secondary catheter 1445 such that the catheter 1430 and the outlet or secondary catheter 1445 are in fluid communication. As described in detail in the '247 patent, the outlet or secondary catheter 1445 is configured to extend through the opening and/or port defined by the proximal end portion of the introducer 1415. In this manner, a proximal end portion of the catheter 1430 and/or the outlet or secondary catheter 1445 can be coupled to a fluid reservoir, fluid source, syringe, and/or the like via a coupler 1446, which in turn, places the catheter 1430 in fluid communication therewith.

In use, the fluid transfer device 1410 can be manipulated to move the actuator 1420 relative to the introducer 1415, from a proximal position to a distal position. Moving the actuator 1420 relative to the introducer 1415, in turn, can move the catheter 1430 coupled to the first portion of the actuator 1420 between the first position and a second position. That is, by moving the actuator 1420 relative to the introducer 1415 the catheter 1430 can be transitioned to the second position, configuration, and/or state, as shown in FIG. 20, in which at least a portion of the catheter 1430 is distal to and outside of the introducer 1415. In some embodiments, the catheter 1430 can be moved (e.g., via movement of the actuator 1420) between the first position and the second position to transition the transfer device 1410 between the first configuration and/or state and the second configuration and/or state, respectively.

More specifically, at least a portion of the catheter 1430 is disposed within the inner volume of the introducer 1415 and/or the lock 1440 when the catheter 1430 is in the first position (FIG. 19) and at least a portion of the catheter 1430 extends beyond the introducer 1415 and the lock 1440 to place a distal end of the catheter 1430 in a position within the access device 1470 or a position distal to the access device 1470 when the catheter 1430 is in the second position (FIG. 20), as described in further detail herein. When the fluid transfer device 1410 is coupled to the proximal coupler 1454 of the access device 1470, the catheter 1430 of the fluid transfer device 1410 can be transitioned and/or advanced to its second state, configuration, and/or position. As such, at least a portion of the catheter 1430 can be advanced distal to the introducer 1415 and can extend through the proximal coupler 1454, the tubing 1451, the side port 1476, the hub 1471, and the catheter 1472 of the access device 1470.

As described above, the catheter 1430 can be of a predetermined length sufficient to extend through the above portions. For example, in some embodiments, the catheter 1430 can be advanced to its second state, configuration, and/or position such that a distal end portion of the catheter 1430 of the fluid transfer device 1410 is distal to a distal end portion of the catheter 1472 of the access device 1470 and thus, disposed in the vein of the patient. In other embodiments, the catheter 1430 of the fluid transfer device 1430 need not extend beyond the catheter 1472 of the access device 1470. For example, in some instances, the catheter 1430 can be placed in the second state, configuration, and/or position and the distal end portion of the catheter 1430 can remain within the catheter 1472 of the access device 1470 (e.g., proximal to a distal tip of the catheter 1472 of the access device).

While the proximal coupler 1454 of the tubing 1451 is particularly shown and described with reference to FIGS. 19-20, in other embodiments, the side port 1476 and/or a proximal portion of the tubing 1451 can be coupled to and/or can include any suitable lock, coupler, engagement member, seal, port, connector (e.g., a needle-free connector), etc. compatible with the lock 1440 of the fluid transfer device 1410. In some instances, a user may select the desired style of lock or coupler from any number of different styles or types of locks and/or couplers (e.g., a slip luer lock, a locking luer lock, a clip, a coupler, an extension set, an adapter such at the adapter 395, a blunt cannula adapter, a needle-free connector, and/or any other suitable device).

As shown in FIG. 20, once the lock 1440 has coupled the transfer device 1410 to the access device 1470, the transfer device 1410 can be transitioned from the first state to the second state to, for example, transfer a volume of bodily fluid from the patient. For example, the access device 1470 can be included in a closed system access device similar to the device 200 described above with reference to FIGS. 3 and 4. As described above, a user (e.g., a doctor, nurse, physician, surgeon, technician, phlebotomist, etc.) can manipulate such a closed system access device in a substantially similar to the closed systems access device 200 to perform venipuncture.

With the catheter 1472 in a desired position within the vein, a user can remove an insertion device (not shown) from the closed system access device, thereby leaving the catheter 1472 in the desired position within the vein and the hub 1471 of the access device 1470 disposed outside of the patient. The user can then manipulate the transfer device 1410 to couple the transfer device 1410 to the access device 1470 via the side port 1476. As described above, in some embodiments, the lock 1440 can be coupled to the proximal coupler 1454 of the tubing 1451 coupled to the side port 1476 to couple the transfer device 1410 thereto. After coupling the transfer device 1410 to the access device 1470, the user can manipulate the transfer device 1410 to transition it from the first configuration and/or state to the second configuration and/or state, in a manner substantially similar to that described to manipulate the transfer device 210 above. In this manner, any of the fluid transfer devices described herein may be used with and/or may be compatible with at least some commercially available access devices, PIVs, adapters, extension sets, and/or the like. Said another way, in some implementations, coupling the fluid transfer device 1410 to a side port of a closed system access device (e.g., either directly or indirectly via a tubing, coupler, port, connector, adapter, etc.) can allow the fluid transfer device 1410 to be used with at least some commercially available access devices, PIVs, adapters, extension sets, and/or the like.

Figure 21:
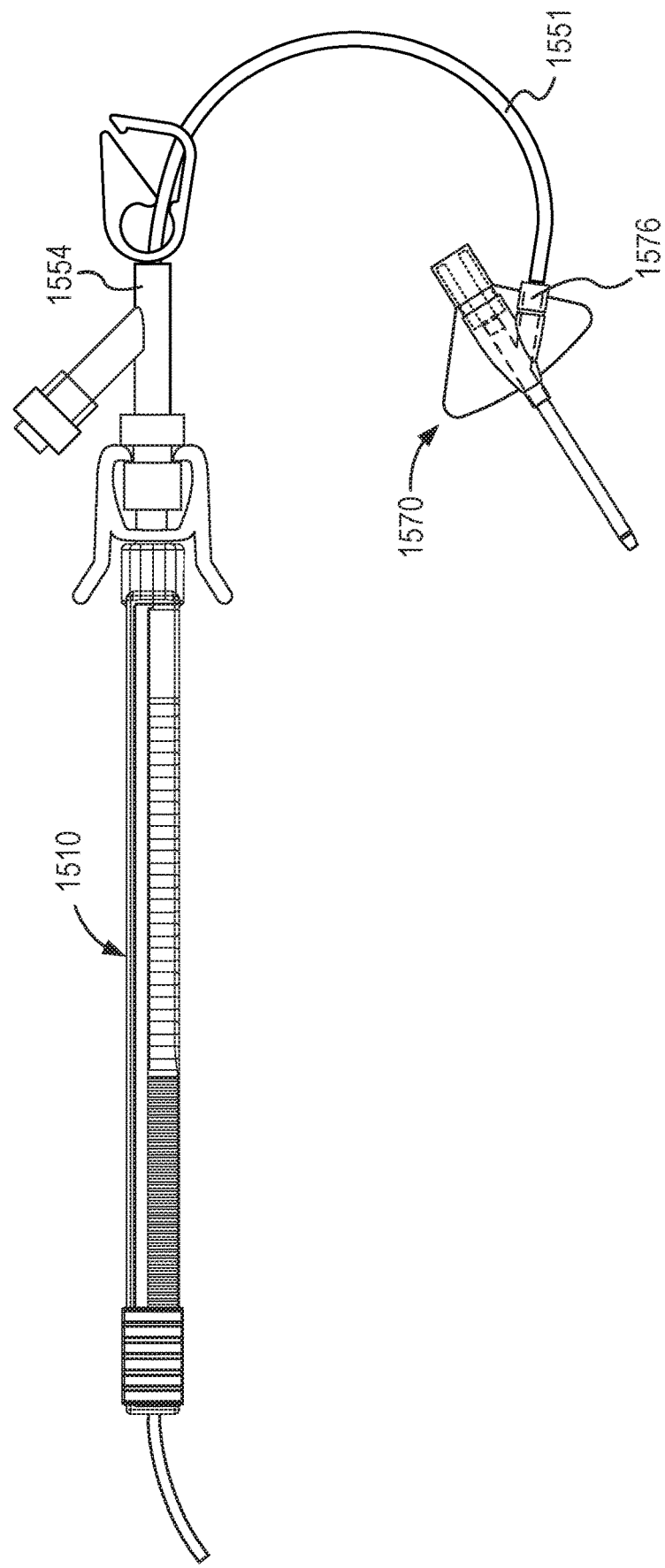
FIGS. 21 and 22 are each a top view illustration of a fluid transfer device coupled to a side port of a closed system access devices according to different embodiments.
Figure 22:
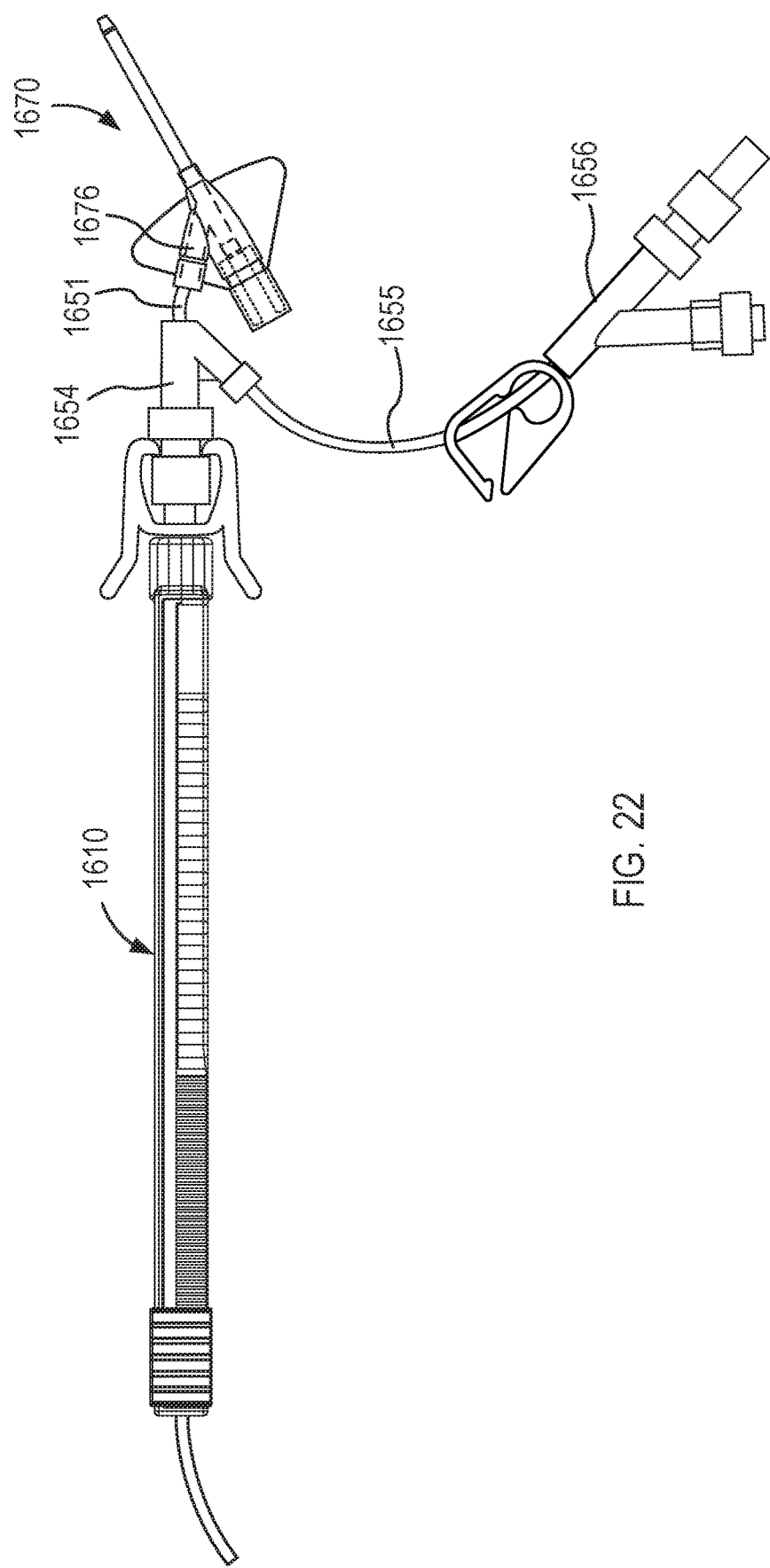

In some embodiments of a closed system access device, an access device can include a proximal portion of the tubing (e.g., a proximal coupler) that is in fluid communication with the side port and that is configured to allow the addition and/or use of one or more infusion lines, extension tubing, adapters, etc., as needed. FIGS. 21 and 22 are top view illustrations of a fluid transfer device 1510 and 1610, respectively, being at least indirectly to two different examples of a closed system access device 1570 and 1670, respectively.

As shown in FIG. 21, the access device 1570 includes the side port 1576 in fluid communication with a piece of tubing 1551 having a predetermined length. A proximal coupler 1554 is coupled to a proximal end portion of the tubing 1551. In the embodiment shown in FIG. 21, the proximal coupler 1554 is configured to be a bifurcated connector (e.g., a Y-connector or a T-connector). The proximal coupler 1554 can include at least one arm configured to be coupled to a distal portion of a fluid transfer device 1510 (e.g., a lock as described above with reference to the transfer device 210 and/or 1410). The proximal coupler 1554 can also include one or more additional arms that can be coupled to any suitable device (e.g., an infusion device, a fluid transfer device, an access device, and/or the like). In some embodiments, the proximal coupler 1554 can be manufactured as a monolithic or unitarily formed piece (e.g., formed from or formed by a single work-piece and/or a substantially contiguous material). In some other embodiments, the proximal coupler 1554 can be formed from combining individual pieces or parts. For example, in such embodiments, a user may select a desired style of lock or coupler from any number of different styles or types of locks and/or couplers (e.g., the lock 240, a slip luer lock, a locking luer lock, a clip, a coupler, an extension set, an adapter such at the adapter 395, a blunt cannula adapter, a needle-free connector, and/or any other suitable device) to form the proximal coupler 1554. More specifically, the proximal coupler 1554 can be configured such that the arms, branches, and/or ports thereof include any of the coupling devices, locks, seals, septums, fluid control devices, needle-free connectors, and/or the like described herein.

As shown in FIG. 22, the access device 1670 includes a side port 1676 in fluid communication with a piece of tubing 1651 having a proximal coupler 1654 coupled to and/or included at a proximal end portion of the tubing 1651. As shown in FIG. 22, the tubing 1651 can have a predetermined length different from the length of the tubing 1551 of the access device 1570. More specifically, the tubing 1551 coupled to the access device 1570 can be substantially longer than the tubing 1651 coupled to the access device 1670. In some embodiments, for example, the tubing 1651 need only be sufficiently long to allow the side port 1676 of the access device 1670 to be coupled to a proximal coupler 1654. As described above, the proximal coupler 1654 can be configured as a bifurcated connector (e.g., a Y-connector or a T-connector). The proximal coupler 1654 can include at least one arm configured to be coupled to a distal portion of the fluid transfer device 1610. In some embodiments, the proximal coupler 1654 can also include one or more additional arms that can be coupled to any suitable device, as described above with reference to the proximal coupler 1554.

More specifically, in the embodiment shown in FIG. 22, the proximal coupler 1654 can have a second arm configured to be coupled to tubing 1655. In some embodiments, the tubing 1655 can be configured to include or couple to a second coupler 1656. In some embodiments, the coupler 1656 can be a bifurcated connector similar to that described above with reference to the proximal couplers 1554 or 1654. In other embodiments, the tubing 1655 can be coupled to any suitable port, coupler, device, and/or the like. The transfer devices 1510 and/or 1610 coupled to the proximal couplers 1554 and/or 1654, respectively, can be configured to transition from a first configuration and/or state to a second configuration and/or state to advance a catheter through at least a portion of the access devices 1570 and/or 1670, respectively, as described above with reference to the transfer device 1410 shown in FIGS. 19 and 20.

Figure 23B:
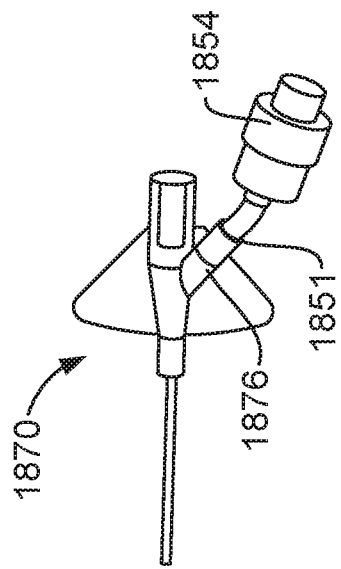
FIGS. 23A-23C are each a top view illustration of a closed system access device with a side port including proximal portions configured to be coupled to a fluid transfer device according to different embodiments.
Figure 23C:
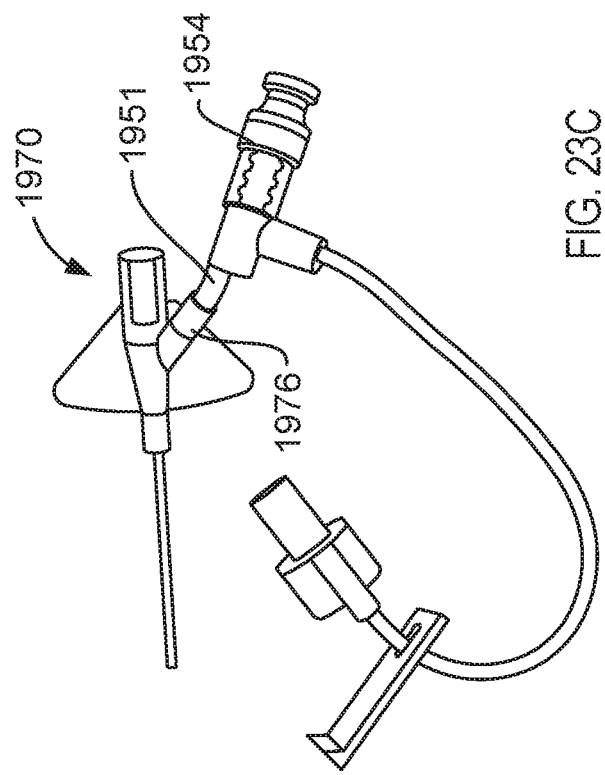
Figure 23A:
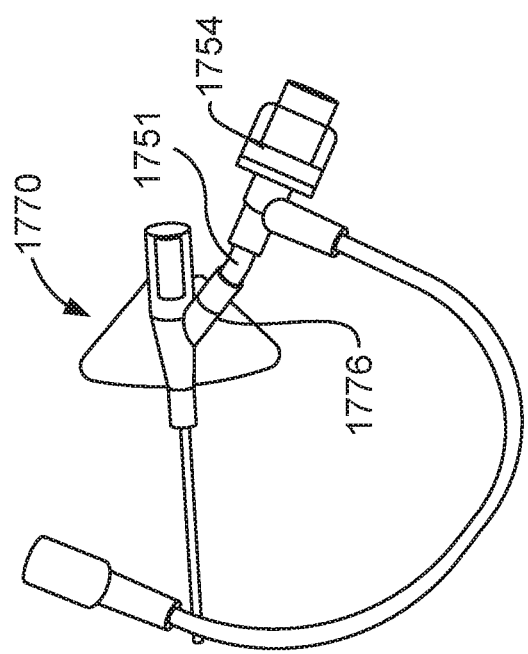

FIGS. 23A-23C are top view illustrations of various closed system access devices that can be used with and/or otherwise coupled to a fluid transfer device to transfer bodily fluid from a patient to one or more fluid collection devices, containers, reservoirs, etc. via a side port of the access devices. As shown in FIG. 23A, an access device 1770 can include a side port 1776 configured to include and/or couple to a tubing 1751. As described above with reference to the tubing 1551 and/or 1651, the tubing 1751 can have any suitable length. A proximal end portion of the tubing 1751 can include a proximal coupler 1754 that is configured as a bifurcated connector as described above with reference to FIGS. 21 and 22. More specifically, the proximal coupler 1754 can be configured as a T-shaped connector having at least a first arm or port and a second arm or port. As shown in FIG. 23A, the first arm or port of the proximal coupler 1754 includes a port, coupler, lock, adapter, needle-free connector, etc. configured to allow a fluid transfer device (e.g. fluid transfer devices 110, 210, and/or 310) to be coupled thereto. The second arm or port is coupled to and/or otherwise extends into a piece of tubing.

FIG. 23B illustrates an access device 1870 that includes a side port 1876, a piece of tubing 1851, and a proximal coupler 1854 included at or coupled to a proximal end portion of the tubing 1851. The proximal coupler 1854 is configured to be coupleable to a fluid transfer device (e.g. fluid transfer devices 110, 210, and/or 310) as described herein. More specifically, while the proximal couplers 1554, 1654, and/or 1764 have been shown and described as being bifurcated couplers having at least a first arm or port and a second arm or port, in the embodiment shown in FIG. 23B, the proximal coupler 1854 can be a single port coupler. In some embodiments, the port of the proximal coupler 1854 can include a fluid control device, a needle-free valve or connector, a seal, a lock, a septum, and/or the like. In other embodiments, the port of the proximal coupler 1854 can be a substantially open port (e.g., similar to the proximal coupler 1454 described above with reference to FIGS. 19 and 20).

FIG. 23C illustrates an access device 1970 with a side port 1976, a piece of tubing 1951, and a proximal coupler 1954 included at or coupled to a proximal end portion of the tubing 1951. The proximal coupler 1954 is shown to be configured as a bifurcating connector with one arm configured to be coupled to a fluid transfer device (e.g. fluid transfer devices 110, 210, and/or 310) and a second arm coupled to and/or otherwise extending into a piece of tubing. In some embodiments, the proximal coupler 1954 can be similar in at least form and/or function to the proximal coupler 1754 described above. More specifically, the proximal coupler 1754 shown in FIG. 23A can include a port having a first fluid control device such as a luer lock, split septum, needle-free connector, and/or the like. The proximal coupler 1954 shown in FIG. 23C, on the other hand, can have a port that includes a second fluid control device such as a needle free connector, valve, and/or the like.

Figure 24:
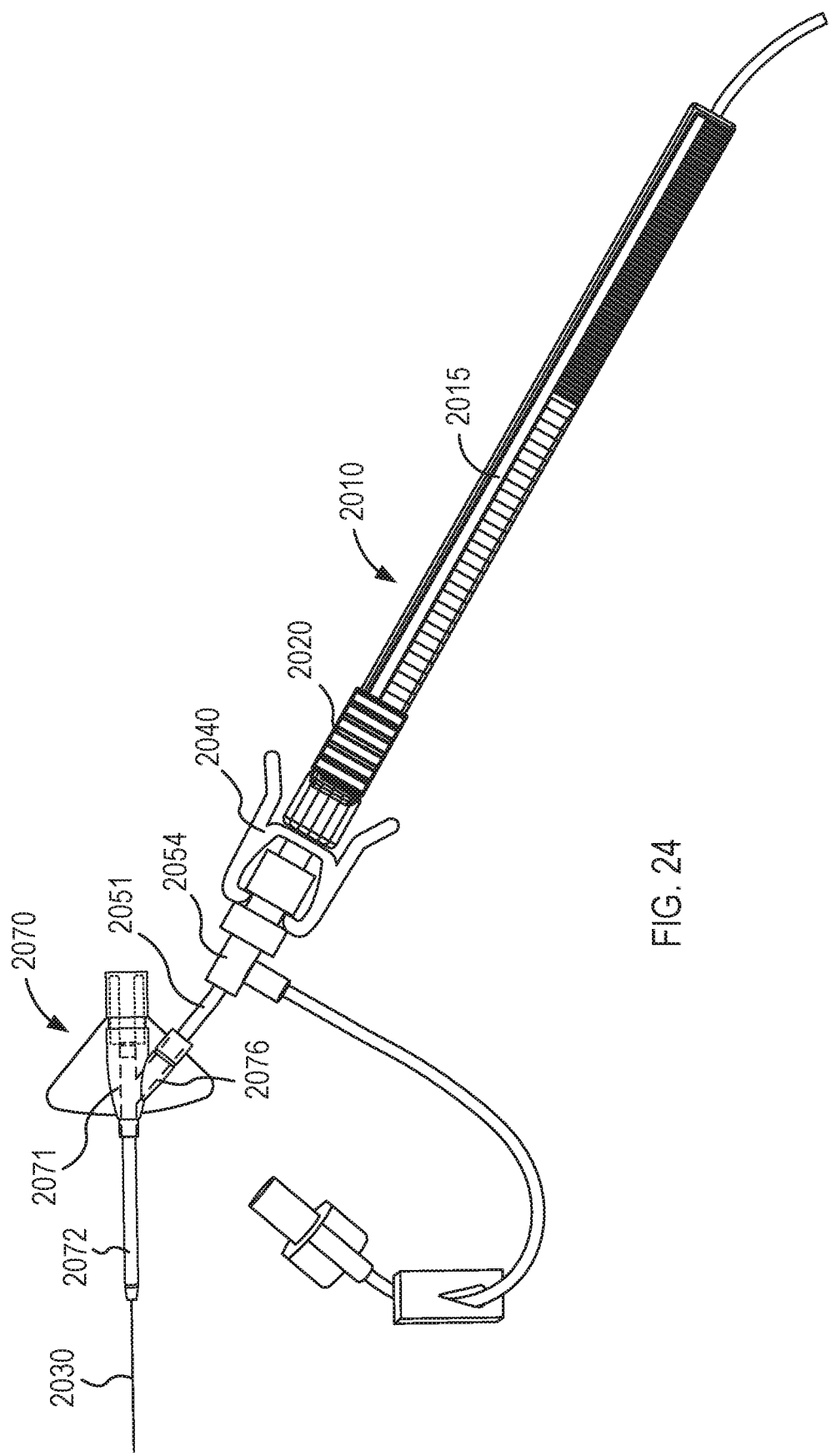
FIG. 24 is a top view illustration a fluid transfer device coupled to a side port of a closed system access device according to an embodiment and disposed in a second configuration.

In any of the embodiments shown in FIGS. 23A-23C, a fluid transfer device can be coupled to the proximal couplers 1754, 1854, and/or 1954 and can be manipulated to advance a catheter of the fluid transfer device through the proximal couplers 1754, 1854, and/or 1954, the tubing 1751, 1851, and/or 1951, and at least a portion of the access devices 1770, 1870, and/or 1970, as described above with reference to the fluid transfer device 1410 shown in FIGS. 19 and 20. For example, FIG. 24 illustrates fluid transfer device 21010 that is coupled to a closed system access device 2070 via a side port 2076 of the access device 2070. The access device 2070 can be substantially similar to any of the access devices 1470, 1570, 1670, 1770, 1870, and/or 1970 described about. For example, the access device 2070 includes a hub 2071, a side port 2076, and a catheter 2072. In addition, a piece of tubing 2051 is coupled to the side port 2076 and a proximal end portion of the tubing 2051 is coupled to and/or otherwise includes a proximal port 2054. The proximal port 2054 can be substantially similar to any of the proximal ports 1454, 1554, 1654, 17554, 1854, and/or 1954 described above.

The fluid transfer device 2010 includes an introducer 2015, an actuator 2020, a catheter 2030, and a lock 2040. As described above, the actuator 2020 is coupled to the catheter 2030 and is configured to move the catheter 2030 distally with respect to the introducer 2015. For example, the actuator 2020 can be moved from a first position (e.g., at or near a proximal end portion of the introducer 2015) to a second position (e.g., at or near a distal end portion of the introducer 2015, as shown in FIG. 24). Following the movement of the actuator 2020, the catheter 2030 can be moved from a first configuration (not shown in FIG. 24) of being disposed within the introducer 2015 and/or a portion of the lock 2040 and proximal to the access device 2070 to a second configuration (shown in FIG. 24) of being disposed and extending through the fluid transfer device 2010, the proximal coupler 2054, the tubing 2051, the side port 2076, the lumen of the access device 2070, and the catheter 2072. More specifically, in this example, the catheter 2030 is shown as being placed such that a distal end portion of the catheter 2030 of the transfer device 2010 is in a distal position relative to the distal end portion of the catheter 2072 of the access device 2070.

In some embodiments, as described above, a catheter can be advanced via a side port of an indwelling access device to be placed in a vein of a patient. The catheter can be sufficiently soft and flexible to allow bending without kinking and to be guided along the side port and/or inner surface of the access device to be extended distally near or past the catheter of the access device. The catheter can be also of a predetermined length sufficient to extend through the fluid transfer device, any tubing and connectors coupled to the side port of the access device, the lumen of the access device, and the catheter of the access device. The catheter can be selected to be sufficiently stiff to be advanced or moved by the movement of an actuator of the fluid transfer device while remaining sufficiently flexible to be advanced through one or more turns, bends, curves, and/or paths of the access device and/or any intervening device that is coupled to the access device.

In some embodiments, the closed system access devices can include access devices specifically adapted to introduce and/or move a catheter through the lumen of the access device via the side port, to overcome potential resistance or impediment or obstruction to the advancement of the catheter introduced via the side port of the access device. For example, in some embodiments the access device can be configured and/or formed with one or more structural features (e.g., guide structures) to aid unobstructed movement of the catheter from a first configuration and/or state in which the catheter is disposed or substantially disposed within the inner volume of the introducer of the fluid transfer device to a second position, configuration, and/or state in which at least a portion of the catheter is distal to and outside of the introducer.

Figure 25:
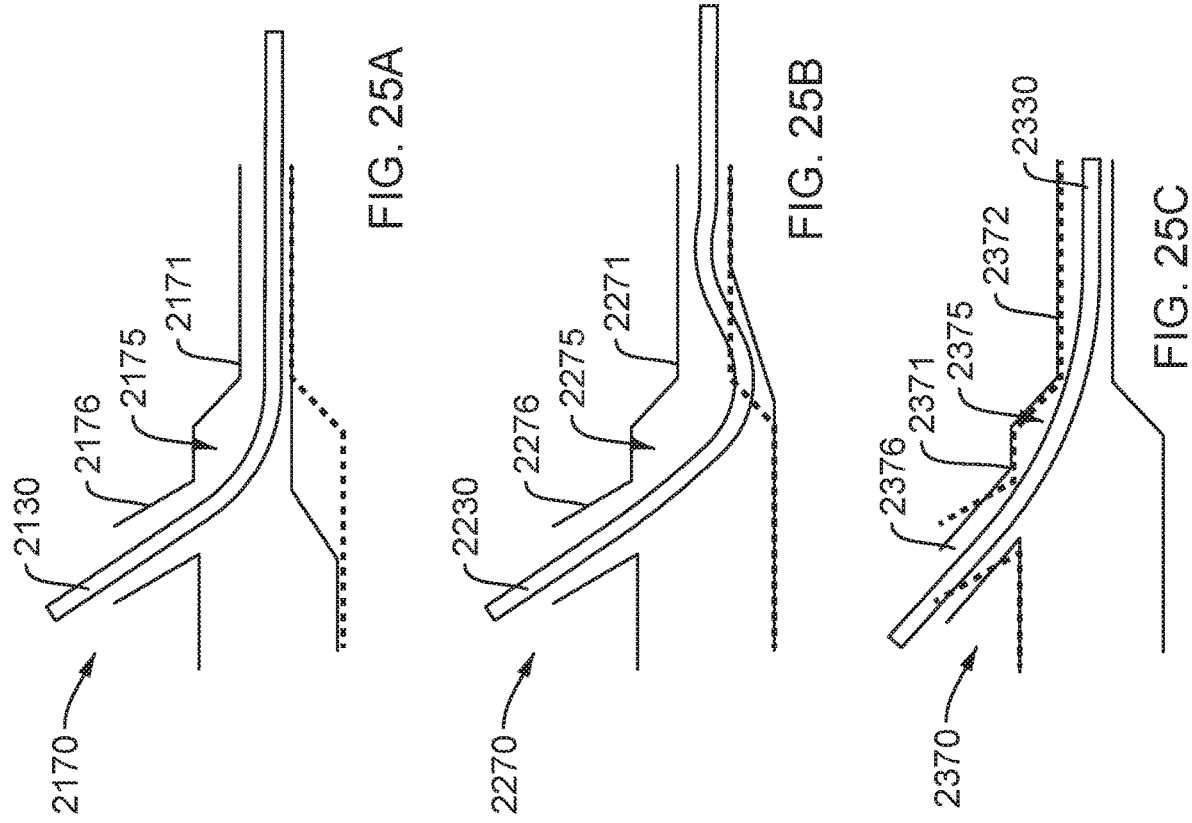
FIGS. 25A-25E are schematic illustrations of closed system access devices adapted to aid in the advancement a catheter through a portion of the closed system access device according to various embodiments.

FIGS. 25A-25E illustrate examples of access devices including one or more such features. For example, FIG. 25A shows an access device 2170 that includes a hub 2171 having an inner wall or surface that defines a lumen 2175. The hub 2171 further includes a side port 2176 that is in fluid communication with the lumen 2175 defined by the hub 2171. In some embodiments, the wall of the hub 2171 of the access device 2170 opposite the side port 2176 can be modified to form a straight wall portion devoid of an angled surface that may otherwise be present (e.g., shown in FIG. 25A by the solid lines compared to the unmodified angular surface shown in dashed lines).

As described in detail above, the access device 2170 can be configured for use with a fluid transfer device that is at least operably coupled to the side port 2176. The fluid transfer device, in turn, is configured to advance a catheter 2130 from the fluid transfer device and into and/or through the access device 2170. In some instances, by modifying the placement of the angled surface of the hub 2171, the catheter 2130 introduced via the side port 2176 can be slid along the modified wall portion (e.g., a now straight portion of the wall) toward a distal portion of the access device 2170 (e.g., the catheter of the access device 2170) without being impeded during advancement by impacting the angled surface otherwise in-line with the path of the catheter 2130. Accordingly, the inner wall of the hub 2171 can form a guide structure configured to guide the catheter 2130 toward the a distal portion of the access device 2170.

FIG. 25B shows an access device 2270 that includes a hub 2271 having an inner wall or surface that defines a lumen 2275. The hub 2271 further includes a side port 2276 that is in fluid communication with the lumen 2275 defined by the hub 2271. In some embodiments, the wall of the hub 2271 of the access device 2270 opposite the side port 2276 can be modified to form an angular wall portion with a relatively shallow angle when compared to an unmodified wall (e.g., shown in FIG. 25B by the solid lines compared to the unmodified angular surface shown in dashed lines).

As described in detail above, the access device 2270 can be configured for use with a fluid transfer device that is at least operably coupled to the side port 2276. The fluid transfer device, in turn, is configured to advance a catheter 2230 from the fluid transfer device and into and/or through the access device 2270. In some instances, by modifying the angle of the angled surface of the hub 2271 (e.g., decreasing the angle and/or making the angle shallower), the catheter 2230 introduced via the side port 2276 can be slid along the modified wall portion (e.g., now the portion of the wall having the shallow angle) toward a distal portion of the access device 2270 (e.g., the catheter of the access device 2270) without being impeded, blocked, and/or kinked during advancement. The shallow angle can be sufficiently shallow to guide the catheter 2230 towards the distal portion of the access device 2270 without requiring sharp turns along a path of advancement of the catheter 2230 that may otherwise lead to potential kinking of the catheter 2230. Accordingly, the inner wall of the hub 2271 having the relatively shallow angle can form a guide structure configured to guide the catheter 2230 toward the distal portion of the access device 2270.

FIG. 25C illustrates an access device 2370 that includes a hub 2371 having an inner wall or surface that defines a lumen 2375. The hub 2371 further includes a side port 2376 and a catheter 2372 that are each in fluid communication with the lumen 2375 defined by the hub 2371. In the embodiment shown in FIG. 25C, the side port 2376 is configured to be at a shallow obtuse angle with respect to the catheter 2372 of the access device 2370 (e.g., shown in FIG. 25C by the solid lines compared to an angle associated with the unmodified side port shown in dashed lines). The shallow obtuse angle of the side port 2376 can be suitably selected to reduce bending of a catheter 2330 when introduced via the side port 2376 and advanced towards the catheter 2372 of the access device 2370. In this manner, the side port 2376 (based at least in part on its angle relative to the catheter 2372 of the access device 2370) can form a guide structure configured to guide the catheter 2330 toward the distal portion of the access device 2370.

FIGS. 25D and 25E illustrate access devices 2470 and 2570, respectively, that include hubs modified to include guides (e.g., internal guide structures) used to guide the advancement of a catheter introduced via a side port. For example, FIG. 25D shows the access device 2470 that includes a hub 2471 having an inner wall or surface that defines a lumen 2475. The hub 2471 further includes a side port 2476 that is in fluid communication with the lumen 2475 defined by the hub 2471. The hub 2471 further includes a guide structure 2457 within and/or extending through the lumen 2475 defined by the hub 2471. The guide structure 2457 can be placed in a suitable position with reference to the side port 2476 such that the catheter 2430 introduced via the side port 2476 is guided (e.g., contacted, directed, and/or deflected) to suitably bend and advance toward the distal portion of the access device 2470. In the embodiment shown in FIG. 25D, the guide structure 2457 can be, for example, a circular internal guide structure.

FIG. 25E shows the access device 2570 that includes a hub 2571 having an inner wall or surface that defines a lumen 2575. The hub 2571 further includes a side port 2576 that is in fluid communication with the lumen 2575 defined by the hub 2571. In the embodiment shown in FIG. 25E, the hub 2571 includes a guide structure 2557 suitably placed within and/or extending through the lumen 2575 of the hub 2571 to guide the catheter 2530 being introduced through the side port 2576. In the embodiment shown in FIG. 25E, the guide structure 2557 can be, for example, a triangular internal guide structure.

In some embodiments, the internal guide structures 2457 and 2557 (e.g., the circular internal guide structure 2457 of the access device 2470 and the triangular internal guide structure 2557 of the access device 2570) can be included in the respective access devices 2470 and 2570, respectively, during manufacture (e.g., can be formed integrally or monolithically with the hub of the access devices). In such embodiments, the internal structures 2470 and/or 2570 can define an opening, hole, aperture, etc. that can allow an insertion member to be movably disposed in the access devices 2470 and/or 2570, respectively (e.g., an insertion device similar to the insertion device 290). In such embodiments, an axis defined by the opening, hole, aperture, etc. can be substantially coaxial with an axis defined by the central lumen of the hubs 2471 and/or 2571 and/or an axis defined by the lumen of the catheter of the hubs 2471 and/or 2571. While the guide structures 2457 and 2557 are shown as being circular and triangular, respectively, in other embodiments, an access device can include a guide structure having any suitable polygonal, elliptical, rounder, and/or irregular shape.

In some other embodiments, the internal structures 2470 and/or 2570 can be configured to be attached to and/or inserted into the access devices 2470 and/or 2570, respectively, by a user prior to use. In still other embodiments, the internal structures 2457 and/or 2557 can be attached to and/or inserted into the access devices 2470 and/or 2570, respectively, after placing a catheter of the access devices 2470 and/or 2570 within the vein of a patient and removing an insertion member configured to facilitate the placement of the catheter (e.g., as described above with reference to the access device 270). In such embodiments, the hubs 2471 and/or 2571 can include an actuator or the like that can be actuated (e.g., after placing the catheter of the hubs 2471 and/or 2571 and removing the insertion member) to place the internal guide structures 2457 and/or 2557 in a desired position. In some embodiments, such an actuator can be manually actuated (e.g., by a user) or automatically actuated (e.g., via a spring and/or the like).

While the access devices 2170, 2270, 2370, 2470, and/or 2570 are described above as having one or more features that is modified to facilitate the advancement of the catheters 2130, 2230, 2330, 2430, and/or 2530, respectively, in other embodiments, an access device need not be modified. For example, in some embodiments, a catheter can be preshaped, pre-stressed, bent, and/or otherwise predisposed to move and/or reconfigure in a manner that can allow entry of the catheter via the side port and advancement of the catheter toward a distal portion of the access device without any modifications of the access device to deflect or guide the catheter.

In some instances, a closed system device can be used by adding a fluid transfer device to an access device (e.g., an indwelling access device) or to an infusion tubing extending from an access device (e.g., a side port of the access device). In such instances, a user can place and/or couple a port at any desired position or location on a tubing and then can couple the fluid transfer device, via the newly placed port, to the access device. In such instances, the user can use one or more port placement devices configured to introduce and/or form ports in, for example, a length of tubing or the like that can be compatible for coupling with a fluid transfer device. In some embodiments, a port placement device can be used to attach or clip-on a separate attachable port to the tubing. The port placement devices can be used to place and/or form ports at or near the side port of the access device, to which any of the fluid transfer devices described herein can be coupled. Upon the placement of such ports a fluid transfer device can be coupled to the port and, in turn, the side port of the access device, thereby allowing the fluid transfer device to transfer of bodily fluids to or from a patient. The port placement devices can be used to introduce any suitable type of port to an existing tubing or extension line. Example types of ports can include a threaded coupler (e.g., similar to a Luer Lok™), a slidable collar, one or more engagement members, and/or any other suitable coupler.

Figure 26:
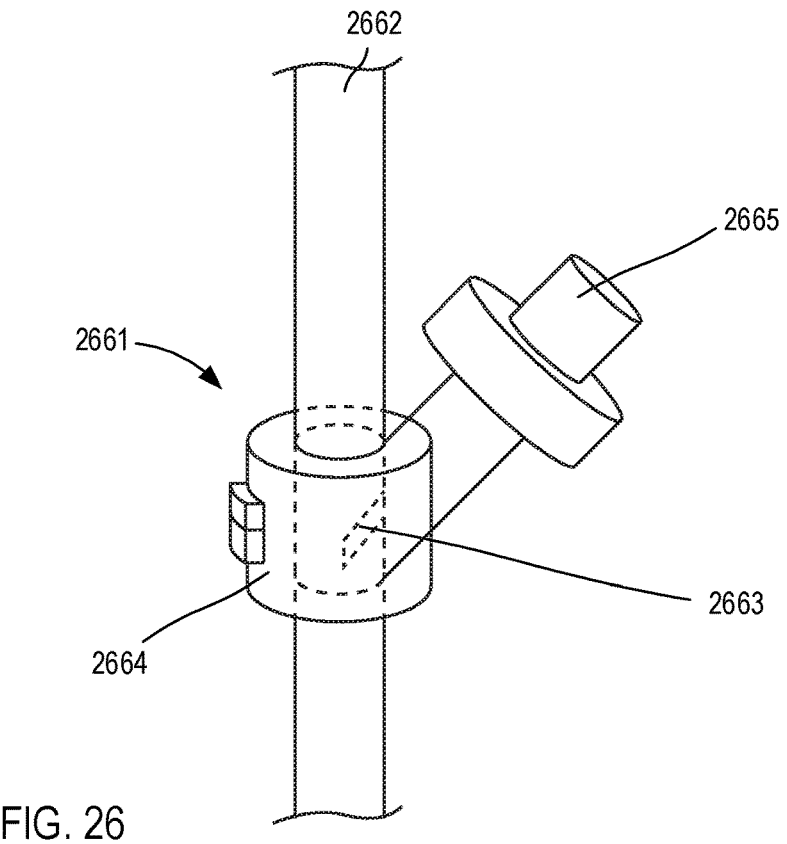
FIG. 26 is a schematic illustration of a port-placement device adapted to introduce and/or form a port on a tubing according to an embodiment.

FIG. 26 and FIGS. 27A-27C illustrate examples of port placement devices 2661 and 2761 configured to introduce ports 2665 and 2765, respectively, on, in, and/or to any desired location on one or more pieces of tubing 2662 and 2762, respectively. For example, the tubing 2662 and/or 2762 can be a piece of tubing extending from a side port of an indwelling access device (not shown in FIG. 26 and/or FIGS. 27A-27C). As shown in FIG. 26 the port placement device 2661 can include a shell 2664, a piercing member 2663 (e.g., a needle), and a port 2665. The port placement device 2661 can aid in the placement of a port 2665 on the tubing 2662 that is suitable for coupling to a fluid transfer device. In some embodiments, the port 2665 can be and/or can include, for example, a Luer Lok™ (e.g., a female luer), a split septum, a needle free connector, and/or any other suitable port. As such, a fluid transfer device can be coupled to the port 2665 and can be manipulated to advance a catheter of the fluid transfer device through the port 2665 and the tubing 2662, through the side port of the access device (not shown), and toward and/or beyond a catheter of the access device (not shown), as described in detail above.

Figure 27A:
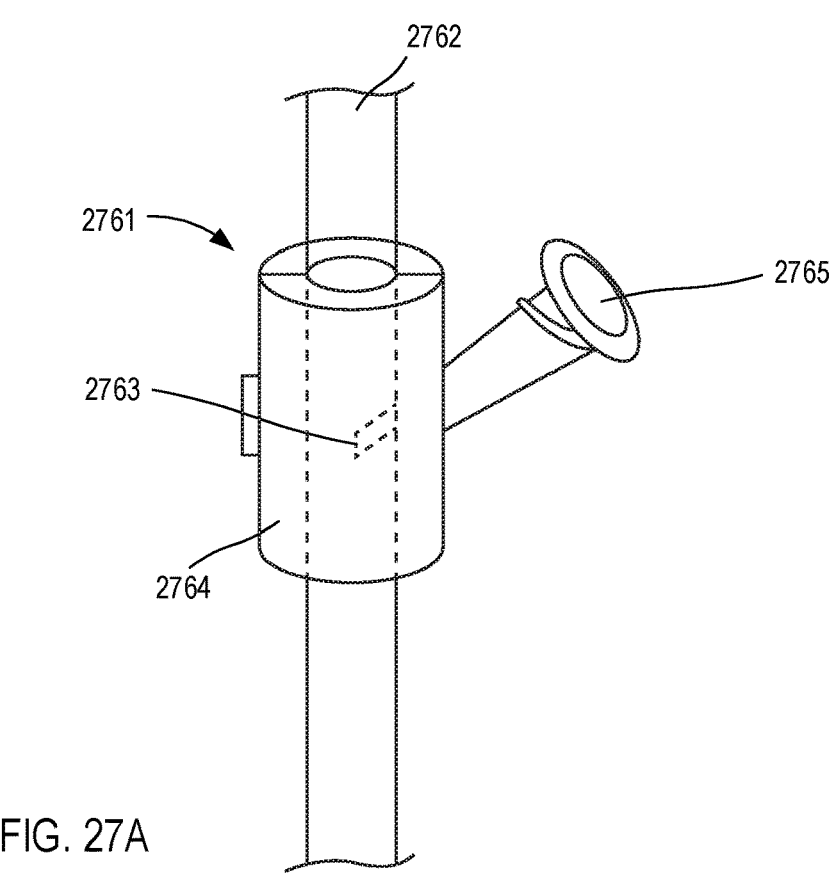
FIG. 27A is a schematic illustration of a port-placement device adapted to introduce and/or form a port on a tubing according to an embodiment.

As shown in FIG. 27A, the port placement device 2761 can include a shell 2764, a piercing member 2763, and a port 2765. The port 2765 can be any suitable port or coupler (e.g., a lock, a slip luer, a locking luer, a clip, a coupler, a split septum, an extension set, an adapter such as the adapter 395, a blunt cannula adapter, and/or any other suitable coupling device). As such, a fluid transfer device can be coupled to the port 2765 and can be manipulated to advance a catheter of the fluid transfer device through the port 2765 and the tubing 2762, through a side port of an access device to which the tubing 2762 is coupled (not shown), and toward and/or beyond a catheter of the access device (not shown), as described in detail above.

Figure 27C:
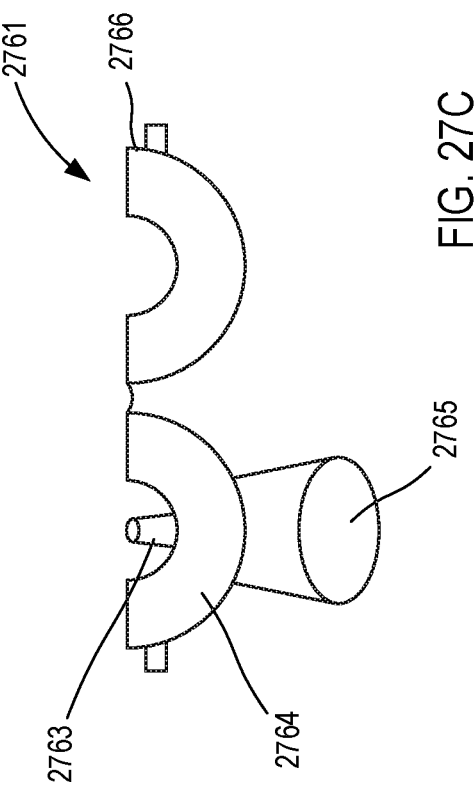
FIGS. 27B and 27C are a side view schematic illustration and a top view schematic illustration, respectively, of the port-placement device of FIG. 27A in an open configuration.
Figure 27B:
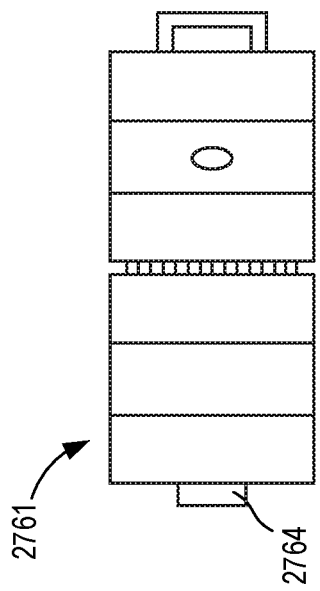

FIGS. 27B and 27C illustrate the port placement device 2761 in an open configuration. As described above, the port placement device 2761 can include the shell 2764 (e.g., a clamshell), with a locking or clasping mechanism 2766, and a piercing member 2763 (e.g., a needle). The clam shell 2764 can be configured to be transitioned from an open configuration (FIGS. 27B and 27C), in which the clasping mechanism 2766 is not engaged and the piercing member 2763 is not engaged with and/or inserted into the tubing 2762, to a closed configuration, in which the clasping mechanism 2766 is engaged and the piercing member 2763 is engaged with and/or inserted into a wall of the tubing 2762 to form a fluid communication between the lumen of the tubing 2762 and the port 2765 (FIG. 27A). The port placement device 2761 can be any suitable size and/or can have any suitable inner circumference to suitably match a tubing on which the port placement device 2761 is configured to place the port 2765, such that upon being transitioned to the closed configuration the port placement device 2761 locks the port 2765 at the location on the tubing 2762 and prevents or reduces relative movement between the tubing 2762 and the port 2765.

The piercing member of a port placement device can be configured in any suitable manner to engage with a wall of a piece of tubing without extending through the entire tubing. As such, a piercing member can pierce the wall of the tubing to form a fluid communication channel between the lumen of the tubing and the port of the port placement device. A piercing member can have any suitable angle of piercing and/or can have any suitable taper, length, tip configuration, and/or the like configured to aid in the piercing of the tubing to place and/or couple a desired port thereto.

Figure 28C:
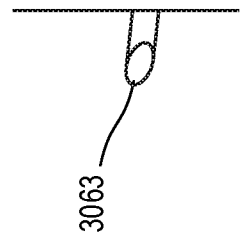
FIGS. 28A-28C are each a side view schematic illustration of a piercing member included in a port-placement device according to various embodiments.
Figure 28B:
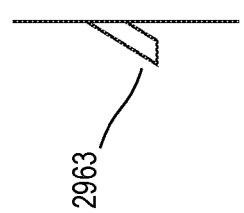
Figure 28A:
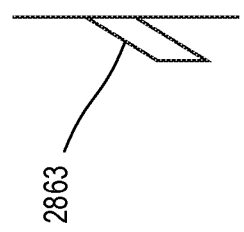

For example, FIGS. 28A-28C are side view illustrations of piercing members 2863, 2963, and 3063 included in port placements devices according to three different embodiments. The piercing member 2863 is shown in FIG. 28A to have an angle of incidence and a tapered tip or point of piercing, the taper being along the angle of incidence. The piercing member 2963 is shown in FIG. 28B to have an angle of incidence with no taper at the tip or point of piercing. Moreover, the piercing member 2963 can have a length that is longer than a length of the piercing member 2863. In addition, the piercing member 2963 can have a diameter that is smaller than a diameter of the piercing member 2863. In some instances, a length, diameter, and/or taper of a piercing member can be based at least in part on the tubing to which the port placement device is being coupled and/or can be based at least in part on the fluid transfer device configured to couple to the port being placed. The piercing member 3063 is shown is shown in FIG. 28C to have no angle of incidence with the piercing angle being, for example, normal or perpendicular to a surface of a tubing being pierced.

Any component or portion of a port placement devices described herein can be formed from any suitable material that can result in a desired hardness, durometer, and/or stiffness of one or more components thereof. For example, in some embodiments, at least the piercing member 2663, 2763, 2863, 2963, and/or 3063 can be formed from a substantially rigid material such as a metal or hard plastic. In other embodiments, a port placement device and/or a portion thereof can be formed of a relatively flexible material, which may result in increased ergonomics and/or a reduction in overall size of the device. For example, the clamshell portion can be formed from a flexible material to suitably mold and/or adhere to the surface of a tubing being pierced.

In use, a user can select a desired location or position on the tubing to place a port. On selecting the location, the user can place a port placement device, while in an open configuration, at the selected location and can transition the port placement device from its open configuration to a closed configuration. Transitioning the port placement device from the open configuration to the closed configuration can be such that the piercing member of the port placement device (e.g., the piercing members 2663, 2763, 2863, 2963, and/or 3063) is inserted into and/or otherwise placed in engagement with the tubing to form a through channel that can establish fluid communication between the lumen of the tubing and the lumen of the port included in the port placement device. In some embodiments, after transitioning the port placement device in the closed configuration, the user can engage a clasping or locking mechanism (e.g., the mechanism 2766 of the port placement device 2761) to lock the port placement device in the closed configuration. In some instances, a fluid transfer device can then be coupled to the port to transfer fluid to or from the patient via the access device. In other instances, any suitable tubing, adapter, coupler, port, fluid control device, and/or the like can be coupled to the port.

In some instances, the use of any of the port placement devices described herein to add ports at any desired location along a piece of tubing can provide users with increased flexibility to couple any suitable device to a side port of, for example, an indwelling access device at any point in the treatment of a patient. In some instances, the use of any of the port placement devices described herein also allows flexibility to use any suitable tubing, combination of tubing, and/or port(s) with access devices and/or fluid transfer devices without the risk of incompatibility and/or without the need for having addition extension lines and/or other complexities when not needed. In some instances, the use of any of the port placement devices described herein can also lead to increased flexibility and/or simplicity in inventory procurement and management at institutions administering healthcare (e.g., hospitals, clinics, urgent care facilities, etc.).

FIG. 29 is a flowchart illustrating a method 10 of using a fluid transfer device with a closed system access device according to an embodiment. The closed system access device can be substantially similar to any of the access devices described herein. For example, in some embodiments, the closed system access device can be similar to the access device 270 described above with reference to FIGS. 3-7. In some implementations, the closed system access device can be a closed system intravenous line. The fluid transfer device can be any of the fluid transfer devices described herein. For example, in some implementations, the fluid transfer device can be substantially similar to the fluid transfer device 210 described above with reference to FIGS. 3-7. In some implementations, the fluid transfer device can be similar to or substantially the same as any of the fluid transfer devices described in the '272 patent, the '247 patent, and/or the '344 patent incorporated by reference above. Accordingly, in some instances, the fluid transfer device can access a body of a patient via the closed system access device and used to transfer fluid to or from the body, as described below.

The method 10 includes coupling an introducer of the fluid transfer device to a proximal port of a hub of the closed system intravenous line after a catheter of the closed system intravenous line has been positioned within the body of the patient and an insertion member has been removed from the closed system intravenous line, at 11. The insertion member can be, for example, a rigid needle used during venipuncture to place the catheter of the closed system intravenous line within a vein of the patient. As described above with reference to, for example, the access device 270, the insertion member couples to the proximal port of the hub and extends through a seal within the proximal port. Once the insertion member is removed from the closed system intravenous line, the seal within the proximal port transitions to a closed state.

As a result of the coupling of the introducer to the proximal port of the hub, the seal included in the proximal port is transitioned from the closed state to an open state, at 12. The seal defines an opening when in the open state that is in fluid communication with a central lumen of the hub, as described in detail above with respect to specific embodiments. With the introducer coupled to the proximal port, an actuator of the fluid transfer device is transitioned from a first state to a second state, at 13. For example, in some embodiments, the actuator can be similar to or substantially the same as the actuator 220 described above with reference to FIGS. 5-7. The actuator can be movably coupled to the introducer and coupled to a catheter of the fluid transfer device such that moving the actuator relative to the introducer is operable to move the catheter relative to the introducer.

The method 10 further includes advancing the catheter of the fluid transfer device from a first position in which the catheter is disposed within the introducer to a second position in which the catheter extends through the seal such that a distal end surface of the catheter is distal to the catheter of the closed system intravenous line, at 14. For example, transitioning the actuator from the first state to the second state can advance the catheter from the first position to the second position. In some instances, when the catheter is in the second position, the catheter can extend through the opening defined by the seal when the seal is in the open state, through the central lumen of the hub, and through the catheter of the closed system intravenous line such that at least the distal end surface of the catheter of the fluid transfer device is disposed beyond a distal end surface of the catheter of the closed system intravenous line and within the vein of the patient. In some instances, when the catheter is in the second position, the fluid transfer device can be used to transfer fluid to or from the patient, as described in detail above.

While various embodiments have been described above, it should be understood that they have been presented by way of example only, and not limitation. For example, while particular fluid transfer devices and access devices are described herein, it should be understood that the concepts described herein are not intended to be limited to the physical embodiments presented. In some embodiments, a fluid transfer device may be similar to and/or the same as any of those described in the '272 patent, the '247 patent, and/or the '344 patent, incorporated by reference above. In some embodiments, a transfer device may include one or more portions that are similar to one or more portions or combination of portions of any of the devices described in the '272 patent, the '247 patent, and/or the '344 patent.

In other embodiments, a fluid transfer device may have any suitable shape, size, and/or configuration. In some embodiments, an access device may be similar to and/or the same as any suitable commercially available access device such as, for example, peripheral intravenous catheter devices (PIVs) and more particularly, to any suitable "closed system" PIVs. In other embodiments, a suitable access device (or PIV) may have any suitable shape, size, and/or configuration. Similarly, in some embodiments, an adapter or the like may be coupled between an access device (or PIV) and a fluid transfer device. In such embodiments, the adapter can be any suitable adapter (e.g., a single port adapter, a Y-adapter, a T-adapter, or the like), extension set, coupler, port, etc. In other embodiments, the adapter can be substantially similar in at least form and/or function to the adapter 395 described above with reference to FIG. 8. While some of the access devices are described as being at least partially inserted into a vein of a patient (e.g., the access devices are or are similar to a PIV), it should be understood that the access devices can be configured to provide access to any suitable portion of a human or non-human patient.

While the embodiments have been particularly shown and described, it will be understood that various changes in form and details may be made. For example, while the transfer device 200 is shown as including the lock 240, in other embodiments, the transfer device 200 can include any suitable lock 240, coupler, and/or coupling mechanism or means. In some embodiments, the transfer device 200 can be monolithically and/or integrally formed with a lock (e.g., the lock 240). In other embodiments, the transfer device 200 can be coupled (e.g., removably coupled) to a lock (e.g., the lock 240). In such embodiments, a user may select the desired style of lock or coupler from any number of different styles or types of locks and/or couplers (e.g., the lock 240, a slip luer lock, a locking luer lock, a clip, a coupler, an extension set, an adapter such at the adapter 395, a blunt cannula adapter, and/or any other suitable device). As such, the fluid transfer devices described herein may be used with and/or may be compatible with at least some commercially available access devices, PIVs, adapters, extension sets, and/or the like.

Where schematics and/or embodiments described above indicate certain components arranged in certain orientations or positions, the arrangement of components may be modified. Although various embodiments have been described as having particular features and/or combinations of components, other embodiments are possible having a combination of any features and/or components from any of embodiments described herein. For example, while the proximal ports 473, 573, 673, 773, 873, and 973 have been described above as specifically including the seals 474, 574, 674, 774, 874, and/or 974, respectively, in other embodiments, a proximal port can include one or more seals formed from and/or including any suitable combination of the seals 474, 574, 674, 774, 874, and/or 974 and/or any suitable combination of components and/or aspects thereof. Moreover, any of the seals 474, 574, 674, 774, 874, and/or 974 can be used with and/or can include an additional seal member such as a split septum, a needle-free valve, and/or any other suitable valve, seal, and/or connector.

The specific configurations of the various components can also be varied. For example, the size and specific shape of the various components can be different from the embodiments shown, while still providing the functions as described herein. More specifically, the size and shape of the various components can be specifically selected for a desired or intended usage. Thus, it should be understood that the size, shape, and/or arrangement of the embodiments and/or components thereof can be adapted for a given use unless the context explicitly states otherwise.

Any of the aspects and/or features of the embodiments shown and described herein can be modified to facilitate and/or affect the performance thereof. For example, in some instances, it may be desirable to position the fluid transfer device at a predetermined angle relative to a surface of the patient's skin. In such instances, any of the access devices described herein can be formed to place a port or coupler at a desired position such that the fluid transfer device is placed at the desired angle when coupled thereto. By way of another example, any of the components of the transfer devices and/or access devices can be formed from any suitable material that can result in a desired hardness, durometer, and/or stiffness of that component. For example, in some embodiments, at least the proboscis 242 of the lock 240 can be formed from a substantially rigid material such as a metal or hard plastic. In such embodiments, forming at least the proboscis 242 from the substantially rigid material can increase the structural support provided by the proboscis 242 to an access device (or at least a desired port thereof) when the proboscis 242 is at least partially disposed therein. Similarly, the proboscis 242 can provide support to and/or otherwise can guide the catheter 230 when the catheter 230 is moved therethrough. In other embodiments, an access device (e.g., a PIV or the like) and/or a portion thereof can be formed of a relatively flexible material, which may result in increased ergonomics and/or a reduction in overall size of the device.

While the proboscis 242 is shown and described above as having a particular size and/or shape, in other embodiments, a lock can include a proboscis that has any suitable length (e.g., longer or shorter than the proboscis 242), width (e.g., wider or narrower than the proboscis 242), and/or shape (e.g., curved, tapered, flared, etc.). In some embodiments, a proboscis can have a surface finish or feature such as one or more threads, flighting (e.g., an auger flighting), ribs, grooves, and/or the like. In some embodiments, the proboscis 242 can have a diameter and/or length that is associated with and/or at least partially based on one or more internal dimensions of an access device and/or at least a port thereof into which the proboscis is inserted. In some embodiments, the proboscis 242 can have a size, shape, and/or configuration that is associated with a seal, valve, and/or occlusion member disposed within the access device and otherwise blocking, sealing, and/or occluding the port to which the transfer device is coupled. Thus, the arrangement of the proboscis 242 can be such that when the transfer device 200 is coupled to an access device (e.g., the access device 270), the proboscis 242 transitions the seal (e.g., the seal 274) from a closed or sealed state to an open state configured to allow the catheter 230 of the transfer device 200 to be advanced into and/or through the lumen 275 of the access device.

Although not shown, any of the closed system access devices described herein can include and/or can be coupled to a flash chamber or the like configured to receive, for example, a first volume of blood (e.g., a pre-sample of blood) resulting from the initial venipuncture event. In some embodiments, a flash chamber can be disposed in, for example, the body 291 of the insertion device 290 to receive the first volume of blood. In such embodiments, the first volume of blood can flow through, for example, a one-way seal such as a sponge seal or the like and into the flash chamber. The arrangement of the seal can be such that once the seal is wetted (e.g., with blood), the flow of the first volume of blood stops.

Where methods and/or schematics described above indicate certain events and/or flow patterns occurring in certain order, the ordering of certain events and/or flow patterns may be modified. Additionally certain events may be performed concurrently in parallel processes when possible, as well as performed sequentially.

While the embodiments described herein can be used in a variety of settings (ER, in-patient, etc.), the following scenario of withdrawing a sample volume of blood from a patient via a "closed system" PIV is provided by way of example. In some instances, for example, a peripheral intravenous line and/or catheter (PIV) such as the PIV 170 and/or 270 described herein is inserted into a vein of a patient following standard guidelines and once the catheter is positioned within the vein, the insertion device (e.g., rigid needle, trocar, and/or the like) can be withdrawn from the PIV, thereby leaving the PIV catheter disposed in the vein. The PIV can remain within the vein for an extended period and can provide access to the vein for the transfer of fluids (e.g., saline, blood, drug compounds, etc.) to the patient. When it is time to draw blood, a user (e.g., nurse, physician, phlebotomist, and/or the like) can stop the transfer of fluid to the patient, if it is transferring fluid, for approximately 1-5 minutes to allow the fluid to disperse from the blood-drawing site. To draw the blood sample, the user attaches a transfer device (e.g., the transfer devices 100 and/or 200) to a port and/or suitable portion of the extension set and/or adapter. As described in detail herein, in some instances, the coupling of the transfer device to the PIV can be such that a seal or the like of the PIV is transitioned from a closed state to an open state to allow a portion of the transfer device to be advanced into and/or through the PIV. Once coupled, the user transitions the transfer device to from a first configuration (e.g., a storage configuration) to a second configuration, in which a portion of a catheter included in the transfer device extends through the peripheral IV and into the vein.

As described in detail in the '344 patent incorporated by reference above, an end of the catheter can be disposed at a predetermined and/or desired distance from an end or end portion of a catheter of a PIV when the transfer device is in the second configuration to place the catheter in fluid communication with a portion of the vein that receives an unobstructed and/or uninhibited flow of blood. For example, the end of the catheter can be in a distal position relative to the end portion of the PIV and at least one branch vessel, valve, and/or the like in fluid communication with the vein. Once the catheter is in the desired position, the user can attach one or more negative pressure collection containers, tubes, and/or syringes to the transfer device to extract a volume of blood.

In some instances, the volume of blood extracted from the patient can be a first volume of blood that can be discarded and/or at least temporarily stored apart from a subsequent sample volume of blood (e.g., typically a volume of about 1-3 milliliters (mL) but up to 8-10 mL of blood can be a "waste" or "pre-sample" volume). In some instance, the waste volume can include contaminants, non-dispersed residual fluids, and/or the like. After the collection of the waste volume, the user can couple one or more negative pressure containers (e.g., sample containers) and/or syringes to the transfer device to collect a desired blood sample volume. Once the sample volume is collected, the transfer device can be transitioned from the second configuration toward the first configuration and/or a third configuration (e.g., a "used" configuration). The transfer device can then be decoupled from the PIV, extension set, and/or adapter and safely discarded. In some instances, after collecting the sample volume but prior to transitioning the transfer device from the second configuration, the waste or pre-sample volume, for example, can be reinfused into the vein.

What is claimed is:

1. A system, comprising:
a catheter assembly, comprising:
a first catheter defining a first lumen, wherein the first catheter is configured to be disposed within a portion of a body of a patient;
a hub defining a central lumen, the hub comprising:
a proximal end portion having a first port, wherein the first port defines a seal configured to be transitioned from a closed state to an open state,
a distal end portion coupled to the first catheter such that the first lumen is in fluid communication with the central lumen, and
a second port positioned between the proximal end portion and the distal end portion in fluid communication with the central lumen; and
a second catheter having a proximal end portion and a distal end portion and defines a lumen therethrough;
an introducer configured to movably receive the catheter assembly, the introducer comprising a proximal end portion and a distal end portion, wherein the distal end portion of the introducer comprises a lock configured to couple the introducer to the hub and transition the seal of the hub from the closed state to the open state when the lock is coupled to the hub; and
an actuator at least partially disposed in the introducer and coupled to the proximal end portion of the second catheter, the actuator configured to move the second catheter between a first position, in which the second catheter is disposed within the introducer, and a second position, in which the second catheter extends through the seal of the hub such that a distal end surface of the second catheter is positioned distal to the hub when the introducer is coupled to the hub,
wherein the hub comprises a guide having a circular structure and configured to engage the second catheter inserted through the second port to guide the second catheter through the central lumen of the hub and into the lumen of the first catheter, and wherein the guide is disposed within the central lumen along an axis defined by the first catheter and an axis defined by the second port.

2. The system of claim 1, wherein the second catheter is configured to be at least partially disposed in the lock when the second catheter is in the first position.

3. The system of claim 1, wherein the lock comprises a proboscis that defines a lumen, the proboscis being configured to extend through the seal to place the lumen of the proboscis in fluid communication with the central lumen of the hub, an outer surface of the proboscis being engaged by a portion of the seal to collectively form a fluid tight seal therebetween.

4. The system of claim 1, wherein the lock comprises a proboscis, and the lock is configured to couple the introducer to the hub such that a portion of the proboscis is disposed within the seal to place the seal in the open state.

5. The system of claim 4, wherein the proboscis extends through the seal such that a distal end portion of the proboscis is disposed in the central lumen of the hub.

6. The system of claim 4, wherein the proboscis extends through a portion of the seal to place the seal in the open state, the seal defining an opening through which the second catheter extends when the second catheter is moved from the first position to the second position.

7. The system of claim 1, wherein the second port defines a lumen in fluid communication with the central lumen of the hub, and an axis defined by the lumen of the second port being disposed at an obtuse angle relative to an axis defined by the lumen of the first catheter.

8. The system of claim 7, wherein the hub comprises an inner wall that defines a portion of the central lumen, the inner wall is substantially parallel to the axis defined by the first catheter, and the axis defined by the lumen of the second port intersects the inner wall.

9. The system of claim 1, wherein the guide is disposed within the central lumen of the hub such that the axis defined by the first catheter extends through the guide and an axis defined by a lumen of the second port extends through the guide, and
the guide defines an opening extending through the guide, an axis defined by the opening of the guide being substantially coaxial with the axis defined by the first catheter.

10. A method, comprising:
coupling an introducer of a fluid transfer device to a proximal port of a hub of a closed system intravenous line after a catheter of the closed system intravenous line has been positioned within a body of a patient;

transitioning a seal included in the proximal port of the hub from a closed state to an open state as a result of coupling the introducer to the proximal port of the hub, the seal defining an opening that is in fluid communication with a central lumen of the hub when the seal is in the open state;

transitioning an actuator of the fluid transfer device from a first state to a second state; and advancing a catheter of the fluid transfer device from a first position in which the catheter of the fluid transfer device is disposed within the introducer to a second position in which the catheter of the fluid transfer device extends through the seal such that a distal end surface of the catheter of the fluid transfer device is distal to the catheter of the closed system intravenous line, wherein advancing the catheter of the fluid transfer device from the first position to the second position comprises contacting a circular guide of the hub with the catheter of the fluid transfer device, the circular guide being configured to guide the catheter of the fluid transfer device into a lumen of the catheter of the closed system intravenous line.

11. The method of claim 10, wherein the introducer comprises a lock, coupling the introducer to the proximal port of the hub includes coupling the lock to the proximal port such that a proboscis of the lock is at least partially inserted into the seal to transition the seal from the closed state to the open state.

12. The method of claim 10, wherein the introducer comprises a lock, coupling the introducer to the proximal port of the hub includes coupling the lock to the proximal port such that a proboscis of the lock extends through the seal to transition the seal from the closed state to the open state, and an outer surface of the proboscis is engaged by a portion of the seal such that a fluid tight seal is collectively formed therebetween.

13. The method of claim 10, wherein an axis defined by the opening in the seal when the seal is in the open state is coaxial with an axis defined by the central lumen.

14. The method of claim 10, wherein the opening in the seal, the central lumen of the hub, and the lumen of the catheter of the closed system intravenous line collectively define an axis of the closed system intravenous line.

15. The method of claim 14, wherein a lumen defined by the catheter of the fluid transfer device defines an axis that is substantially coaxial with the axis of the closed system intravenous line when the introducer of the fluid transfer device is coupled to the proximal port of the hub.

16. The method of claim 15, wherein the axis defined by the catheter of the fluid transfer device is substantially coaxial with the axis of the closed system intravenous line during the advancing of the catheter of the fluid transfer device from the first position to the second position.

* * * * *